US00RE48150E

(19) United States
(12) Reissued Patent
Corkey et al.

(10) Patent Number: US RE48,150 E
(45) Date of Reissued Patent: Aug. 11, 2020

(54) APOPTOSIS SIGNAL-REGULATING KINASE INHIBITORS

(71) Applicant: Gilead Sciences, Inc., Foster City, CA (US)

(72) Inventors: Britton Corkey, Redwood City, CA (US); Gregory Notte, San Mateo, CA (US); Jeff Zablocki, Los Altos, CA (US)

(73) Assignee: Gilead Sciences, Inc., Foster City, CA (US)

(21) Appl. No.: 15/397,344

(22) Filed: Jan. 3, 2017

Related U.S. Patent Documents

Reissue of:
(64) Patent No.: 8,927,582
Issued: Jan. 6, 2015
Appl. No.: 13/828,984
Filed: Mar. 14, 2013

U.S. Applications:
(62) Division of application No. 13/174,459, filed on Jun. 30, 2011, now Pat. No. 8,440,665.

(60) Provisional application No. 61/361,080, filed on Jul. 2, 2010.

(51) Int. Cl.
*C07D 409/14* (2006.01)

(52) U.S. Cl.
CPC ..... *C07D 409/14* (2013.01)

(58) Field of Classification Search
CPC ..... C07D 409/14
See application file for complete search history.

(56) References Cited

U.S. PATENT DOCUMENTS

| | | | | |
|---|---|---|---|---|
| 4,242,354 | A * | 12/1980 | Bolasco | C07D 333/38 514/448 |
| 7,078,064 | B2 * | 7/2006 | Zabrecky | A61K 31/352 424/725 |
| 8,440,665 | B2 * | 5/2013 | Corkey | C07D 409/14 514/236.2 |
| 9,051,313 | B2 * | 6/2015 | Notte | C07D 417/14 |
| 9,169,243 | B2 * | 10/2015 | Notte | A61K 31/5377 |
| 2007/0167386 | A1 | 7/2007 | Otsu et al. | |
| 2007/0237770 | A1 | 10/2007 | Lai et al. | |
| 2007/0276050 | A1 | 11/2007 | Koch et al. | |
| 2009/0318425 | A1 | 12/2009 | Chang et al. | |

FOREIGN PATENT DOCUMENTS

| | | | |
|---|---|---|---|
| EP | 1677113 | A1 | 7/2006 |
| WO | WO199834946 | A1 | 8/1998 |
| WO | WO2000056866 | A2 | 9/2000 |
| WO | WO2001068850 | A2 | 9/2001 |
| WO | WO2006036941 | A2 | 4/2006 |
| WO | WO-2008011557 | A2 | 1/2008 |
| WO | WO2008073919 | A2 | 6/2008 |
| WO | WO-2009027283 | A1 | 3/2009 |
| WO | WO2009123986 | A1 | 10/2009 |
| WO | WO2010045470 | A2 | 4/2010 |
| WO | WO2010056982 | A2 | 5/2010 |
| WO | WO2010111464 | A1 | 9/2010 |
| WO | WO2011041293 | A1 | 4/2011 |
| WO | WO2011097079 | A1 | 8/2011 |
| WO | WO2011097594 | A2 | 8/2011 |
| WO | WO2011119894 | A2 | 9/2011 |
| WO | WO2012115885 | A1 | 8/2012 |
| WO | WO2012170711 | A1 | 12/2012 |

OTHER PUBLICATIONS

Bataller et al., Liver Fibrosis, The Journal of Clinical Investigation, vol. 115, No. 2, 2005, pp. 209-218.

Ebrahimian et al., Cardiac hypertrophy is associated with altered thioredoxin and ASK-1 signaling in a mouse model of menopause, American Journal of Physiology (Oct. 31, 2008), 295(4), pp. h1481-h1488 In English, Additional Information: Pt. 2, CODEN: AJPHAP ISSN: 0002-9513.

Chen et al., Curcumin inhibits thrombin-stimulated connective tissue growth factor (CTGF/CCN2) production through c-Jun NH2-terminal kinase suppression in human gingival fibroblasts, Journal of Periodontology (Dec. 31, 2012), 83(12), pp. 1546-1553 In English, CODEN: JOPRAJ ISSN: 0022-3492.

Fan et al., Small Heat-Shock Protein Hsp20 Attenuates β-Agonist-Mediated Cardiac Remodeling Through Apoptosis Signal-Regulating Kinase 1, Circulation Research (Nov. 24, 2006), 99(11), pp. 1233-1242 In English, CODEN: CIRUAL ISSN: 0009-7330.

Gan et al., Role of FIP200 in cardiac and liver development and its regulation of TNFα and TSC-mTOR signaling pathways, Journal of Cell Biology (Oct. 9, 2006), 175(1), pp. 121-133 In English,CODEN: JCLBA3 ISSN: 0021-9525.

(Continued)

*Primary Examiner* — Alan D Diamond
(74) *Attorney, Agent, or Firm* — Sheppard Mullin Richter & Hampton LLP

(57) ABSTRACT

The present invention relates to compounds of Formula (I):

(I)

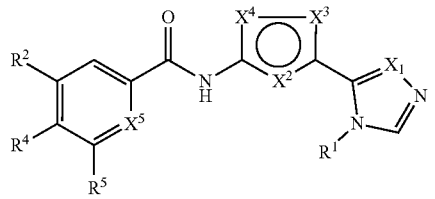

wherein $X^1$, $X^2$, $X^3$, $X^4$, $X^5$, $^R$, $R^1$, $R^2$ are as defined above. The compounds have apoptosis signal-regulating kinase ("ASK1") inhibitory activity, and are thus useful in the treatment of ASK1-mediated conditions, including autoimmune disorders, inflammatory diseases, cardiovascular diseases, diabetes, diabetic nephropathy, cardio-renal diseases, including kidney disease, fibrotic diseases, respiratory diseases, COPD, idiopathic pulmonary fibrosis, acute lung injury, acute and chronic liver diseases, and neurodegenerative diseases.

The invention also relates to pharmaceutical compositions comprising one or more of the compounds of Formula (I), and to methods of preparing the compounds of Formula (I).

9 Claims, No Drawings

(56) References Cited

OTHER PUBLICATIONS

Gilot et al., ASK(1) and you shall receive: a new link between antioxidants and cell death signalling, Hepatology (Philadelphia, PA, United States) (Jul. 31, 2003), 38(1), pp. 252-254 In English, CODEN: HPTLD9 ISSN: 0270-9139.
Gilot et al., Liver protection from apoptosis requires both blockage of initiator caspase activities and inhibition of ASK1/JNK pathway via glutathione S-transferase regulation, Journal of Biological Chemistry (Dec. 20, 2002), 277(51), pp. 49220-49229 In English, CODEN: JBCHA3 ISSN: 0021-9258.
Guo et al., Differential expression of the Toll-like receptor pathway and related genes of chicken bursa after experimental infection with infectious bursa disease virus, Archives of Virology (2012), 157(11), pp. 2189-2199 In English, CODEN: ARVIDF ISSN: 0304-8608.
Hikoso et al., Progression of Heart Failure Was Suppressed by Inhibition of Apoptosis Signal-Regulating Kinase 1 Via Transcoronary Gene Transfer, Journal of the American College of Cardiology (Jul. 31, 2007), 50(5), pp. 453-462 In English, CODEN: JACCDI ISSN: 0735-1097.
Hori et al., Oxidative stress and left ventricular remodelling after myocardial infarction, Cardiovascular Research (Feb. 15, 2009), 81(3), pp. 457-464 In English, CODEN: CVREAU ISSN: 0008-6363.
Hu et al., Class A scavenger receptor attenuates myocardial infarction-induced cardiomyocyte necrosis through suppressing M1 macrophage subset polarization, Basic Research in Cardiology (Nov. 30, 2011), 106(6), pp. 1311-1328 In English, CODEN: BRCAB7 ISSN: 0300-8428.
Izumiya et al., Apoptosis Signal-Regulating Kinase 1 Plays a Pivotal Role in Angiotensin II-Induced Cardiac Hypertrophy and Remodeling, Circulation Research (Oct. 31, 2003), 93(9), pp. 874-883 In English, CODEN: CIRUAL ISSN: 0009-7330.
Kataoka et al., Apoptosis signal-regulating kinase 1 deficiency eliminates cardiovascular injuries induced by high-salt diet, Journal of Hypertension (2010), vol. Date: 2011, 29(1), pp. 76-84 In English, CODEN: JOHYD3 ISSN: 0263-6352.
Kim et al., Inhibition of liver X receptor-α-dependent hepatic steatosis by isoliquiritigenin, a licorice antioxidant flavonoid, as mediated by JNK1 inhibition, Free Radical Biology & Medicine (Dec. 1, 2010), 49(11), pp. 1722-1734 In English, CODEN: FRBMEH ISSN: 0891-5849.
Kudo et al., Lipopolysaccharide triggered TNF-α-induced hepatocyte apoptosis in a murine non-alcoholic steatohepatitis model, Journal of Hepatology (Jul. 31, 2009), 51(1), pp. 168-175 In English, CODEN: JOHEEC ISSN: 0168-8278.
Lim et al., Cannabidiol causes activated hepatic stellate cell death through a mechanism of endoplasmic reticulum stress-induced apoptosis, Cell Death & Disease (Jun. 30, 2011), 2(June), pp. e170/1-e170/11, 11 In English, CODEN: CDDEA4 ISSN: 2041-4889, URL: http://www.nature.com/cddis/journal/v2/n6/pdf/cddis201152a.pdf.
Manapov et al., Translocation of p21Cip1/WAF1 from the nucleus to the cytoplasm correlates with pancreatic myofibroblast to fibroblast cell conversion, Gut (Jun. 30, 2005), 54(6), pp. 814-822 In English, CODEN: GUTTAK ISSN: 0017-5749.
Matkovich et al., Direct and Indirect Involvement of MicroRNA-499 in Clinical and Experimental Cardiomyopathy, Circulation Research (2012), 111(5), pp. 521-531 In English, CODEN: CIRUAL ISSN: 0009-7330.
Nakamura et al., Critical Role of Apoptosis Signal-Regulating Kinase 13 in Aldosterone/Salt-Induced Cardiac Inflammation and Fibrosis, Hypertension (Sep. 30, 2009), 54(3), pp. 544-551 In English, CODEN: HPRTDN ISSN: 0194-911X.
Nako et al., Novel mechanism of angiotensin II-induced cardiac injury in hypertensive rats: the critical role of ASK1 and VEGF, Hypertension Research (2012) 35(2), pp. 194-200 In English, CODEN: HRESE4 ISSN: 0916-9636.
Okiyama et al., Polyenephosphatidylcholine prevents alcoholic liver disease in PPARα-null mice through attenuation of increases in oxidative stress, Journal of Hepatology (Jun. 30, 2009), 50(6), pp. 1236-1246 In English, CODEN: JOHEEC ISSN: 0168-8278.
Oshida et al., Toxicological effect of emodin in mouse testicular gene expression profile, Journal of Applied Toxicology (2011), 31(8), pp. 790-800 In English, CODEN: JJATDK ISSN: 0260-437X.
Roy et al., Fra-2 mediates oxygen-sensitive induction of transforming growth factor β in cardiac fibroblasts, Cardiovascular Research (Sep. 1, 2010), 87(4), pp. 647-655 In English, CODEN: CVREAU ISSN: 0008-6363.
Rui et al., JNK-dependent AP-1 activation is required for aristolochic acid-induced TGF-β1 synthesis in human renal proximal epithelial cells, American Journal of Physiology (Jun. 30, 2012), 302(6), pp. f1569-f1575 in English Additional Information: Pt. 2, CODEN: AJPHAP ISSN: 0002-9513.
Sedeek et al., Critical role of Nox4-based NADPH oxidase in glucose-induced oxidative stress in the kidney: implications in type 2 diabetic nephropathy, American Journal of Physiology (Dec. 31, 2010), 299(6), pp. f1348-f1358 In English, Additional Information: Pt. 2, CODEN: AJPHAP ISSN: 0002-9513.
Sharma et al., Cdc42 and Rac1 are major contributors to the saturated fatty acid-stimulated JNK pathway in hepatocytes, Journal of Hepatology (Jan. 31, 2012), 56(1), pp. 192-198 in English, CODEN: JOHEEC ISSN: 0168-8278.
Taki et al., Apoptosis signal-regulating kinase 1 is crucial for oxidative stress-induced but not for osmotic stress-induced hepatocyte cell death, Life Sciences (Dec. 19, 2008), 83(25-26), pp. 859-864 In English, CODEN: LIFSAK ISSN: 0024-3205.
Taniike et al., Apoptosis Signal-Regulating Kinase 1/p38 Signaling Pathway Negatively Regulates Physiological Hypertrophy, Circulation (Jan. 29, 2008), 117(4), pp. 545-552 In English, CODEN: CIRCAZ ISSN: 0009-7322.
Thandavarayan et al., 14-3-3 protein regulates Ask1 signaling and protects against diabetic cardiomyopathy, Biochemical Pharmacology (May 1, 2008), 75(9), pp. 1797-1806 In English, CODEN: BCPCA6 ISSN: 0006-2952.
Toldo et al., Inhibition of apoptosis signal-regulating kinase 1 reduces myocardial ischemia-reperfusion injury in the mouse, Journal of the American Heart Association (Oct. 31, 2012), 1(5), pp. 002360/1-002360/8 In English, CODEN: JAHABZ ISSN: 2047-9980.
Tsujimoto et al., The Antioxidant Edaravone Attenuates Pressure Overload-Induced Left Ventricular Hypertrophy, Hypertension (May 31, 2005), 45(5), pp. 921-926 In English, CODEN: HPRTDN ISSN: 0194-911X.
Xue et al., Elevated myocardial Na+/H+ exchanger isoform 1 activity elicits gene expression that leads to cardiac hypertrophy, Physiological Genomics (Aug. 31, 2010), 42(3), pp. 374-383 In English, CODEN: PHGEFP ISSN: 1094-8341, URL: http://physiolgenomics/physiology.org/cgi/reprint/42/3/374.
Yamaguchi et al., Cardiac-specific disruption of the c-raf-1 gene induces cardiac dysfunction and apoptosis, Journal of Clinical Investigation (Oct. 31, 2004), 114(7), pp. 937-943 In English, CODEN: JCINAO ISSN: 0021-9738.
Yamamoto et al., Olmesartan Prevents Cardiovascular Injury and Hepatic Steatosis in Obesity and Diabetes, Accompanied by Apoptosis Signal Regulating Kinase-1 Inhibition, Hypertension (Sep. 30, 2008), 52(3), pp. 573-580 In English, CODEN: HPRTDN ISSN: 0194-911X.
Yamashita et al., Apoptosis signal-regulating kinase-1 is involved in vascular endothelial and cardiac remodeling caused by nitric oxide deficiency, Hypertension (Sep. 30, 2007), 50(3), pp. 519-524 In English, CODEN: HPRTDN ISSN: 0194-911X.
Yang et al., TLR4 activity is required in the resolution of pulmonary inflammation and fibrosis after acute and chronic lung injury, American Journal of Pathology (Jan. 31, 2012), 180(1), pp. 275-292 In English, CODEN: AJPAA4 ISSN: 0002-9440.
Ye et al., Dermatophagoides pteronyssinus 2 regulates nerve growth factor release to induce airway inflammation via a reactive oxygen species-dependent pathway, American Journal of Physiology (Feb.

(56) References Cited

OTHER PUBLICATIONS 28, 2011), 300(2), pp. I216-I224 In English, Additional Information: Pt. 1,CODEN: AJPHAP ISSN: 0002-9513.
Zhang et al., Tumor necrosis factor-α accelerates apoptosis of steatitic hepatocytes from a murine model of non-alcoholic fatty liver disease, Biochemical and Biophysical Research Communications (Jan. 22, 2010), 391(4), pp. 1731-1736 In English, CODEN: BBRCA9 ISSN: 0006-291X.
Zuo et al., Oligomerized grape seed proanthocyanidins ameliorates isoproterenol-induced cardiac remodeling in rats: role of oxidative stress, Phytotherapy Research (May 31, 2011), 25(5), pp. 732-739 In English, CODEN: PHYREH ISSN: 0951-418X.
http://www.intelihealth.com/IH/intlh/WSIHW000/8303/9117/195703.html?d=dmtHealthAZ, 2007.*
http://www.alzheimersscreen.com/Prevention.htm, 2005.*
International Search Report for PCT/US2011/042694, international filing date Jun. 30, 2011, mailed Aug. 22, 2011.
International Preliminary Report on Patentability for PCT/US2011/042694 dated Jan. 17, 2013.
Examination Report for AU201127282, mailed Oct. 31, 2013.
First Examination Report for NZ604831, mailed Oct. 4, 2013.
Search Report for CN201180033172.3 (English translation), mailed May 27, 2014.
Office Action for EA201291273/28 (English translation), mailed Aug. 11, 2014.
Office Action for MX/a/2012/015105 (English translation), mailed Mar. 12, 2014.

* cited by examiner

APOPTOSIS SIGNAL-REGULATING KINASE INHIBITORS

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

CROSS-REFERENCE TO RELATED APPLICATIONS

This application is a Divisional of U.S. patent application Ser. No. 13/174,459, filed Jun. 30, 2011, which claims the benefit under 35 U.S.C. §119(e) to U.S. Provisional Patent Application Ser. No. 61/361,080, filed Jul. 2, 2010, the entirety of which is incorporated herein by reference.

FIELD OF THE INVENTION

The present invention relates to novel compounds having enzyme inhibitory activity, and to their use in the treatment of ASK1-mediated conditions, including autoimmune disorders, inflammatory diseases, including chronic kidney disease, cardiovascular diseases and neurodegenerative diseases. The invention also relates to methods for their preparation, and to pharmaceutical compositions containing such compounds.

BACKGROUND

Mitogen-activated protein kinase (MAPK) signaling cascades couple diverse extracellular and intracellular queues to appropriate cellular stress responses, including cell growth, differentiation, inflammation, and apoptosis (Kumar, S., Boehm, J., and Lee., J. C. (2003) Nat. Rev. Drug Dis. 2:717-726; Pimienta, G., and Pascual, J. (2007) Cell Cycle, 6: 2826-2632). MAPKs exist in three groups, MAP3Ks, MAP2Ks, and MAPKs, which are sequentially activated. MAPK3s directly respond to environmental signals and phosphorylate MAP2Ks, which in turn phosphorylate specific MAPKs. MAPKs then mediated the appropriate cellular response by phosphorylating cellular substrates, including transcription factors that regulate gene expression.

Apoptosis signal-regulating kinase 1 (ASK1) is a member of the mitogen-activated protein kinase kinase kinase ("MAP3K") family that activates the c-Jun N-terminal protein kinase ("JNK") and p38 MAP kinase (Ichijo, H., Nishida, E., Irie, K., Dijke, P. T., Saitoh, M., Moriguchi, T., Matsumoto, K., Miyazono, K., and Gotoh, Y. (1997) Science, 275, 90-94). ASK1 is activated by a variety of stimuli including oxidative stress, reactive oxygen species (ROS), LPS, TNF-α, FasL, ER stress, and increased intracellular calcium concentrations (Hattori, K., Naguro, I., Runchel, C., and Ichijo, H. (2009) Cell Comm. Signal. 7:1-10; Takeda, K., Noguchi, T., Naguro, I., and Ichijo, H. (2007) Annu. Rev. Pharmacol. Toxicol. 48: 1-8.27; Nagai, H., Noguchi, T., Takeda, K., and Ichijo, I. (2007) J. Biochem. Mol. Biol. 40:1-6). ASK1 undergoes activation via autophosphorylation at Thr838 in response to these signals and in turn phosphorylates MAP2Ks, such as MKK3/6 and MKK4/7, which then phos- phorylate and activates p38 and JNK MAPKs, respectively. ASK2 is a related MAP3K that shares 45% sequence homology with ASK1 (Wang, X. S., Diener, K., Tan, T-H., and Yao, Z. (1998) Biochem. Biophys. Res. Commun. 253, 33-37. Although ASK2 tissue distribution is restricted, in some cell types ASK1 and ASK2 have been reported to interact and function together in a protein complex (Takeda, K., Shimozono, R., Noguchi, T., Umeda, T., Morimoto, Y, Naguro, I., Tobiume, K., Saitoh, M., Matsuzawa, A., and Ichijo, H. (2007) J. Biol. Chem. 282: 7522-7531; Iriyamao, T., et al. (2009) Embo J. 28: 843-853) In non stressed conditions, ASK1 is kept in an inactive state through binding to its repressor Thioredoxin (Trx) (Saitoh, M., Nishitoh, H., Fuji, M., Takeda, K., Tobiume, K., Sawada, Y., Kawabata, M., Miyazono, K., and Ichijo, H. (1998) Embo J. 17:2596-2606), and through association withAKT (Zhang, L., Chen, J. and Fu, H. (1999) Proc. Natl. Acad. Sci. U.S.A 96:8511-8515).

Phosphorylation of ASK1 protein can lead to apoptosis or other cellular responses depending on the cell type. ASK1 activation and signaling have been reported to play an important role in a broad range of diseases including neurodegenerative, cardiovascular, inflammatory, autoimmunity, and metabolic disorders. In addition, ASK1 has been implicated in mediating organ damage following ischemia and reperfusion of the heart, brain, and kidney (Watanabe et al. (2005) BBRC 333, 562-567; Zhang et al., (2003) Life Sci 74-37-43; Terada et al. (2007) BBRC 364: 1043-49). Emerging evidence suggests that ASK2, either alone or in a complex with ASK1, may play important roles in human diseases as well. Therefore, therapeutic agents that function as inhibitors of ASK1 and ASK2 signaling complexes have the potential to remedy or improve the lives of patients suffering from such conditions.

U.S. Publication No. 2007/0276050 describes methods for identifying ASK1 inhibitors useful for preventing and/or treating cardiovascular disease and methods for preventing and/or treating cardiovascular disease in an animal. The methods comprise administering to the animal an ASK1 inhibitor and, optionally, a hypertensive compound.

U.S. Publication No. 2007/0167386 reports a drug for at least one of prevention and treatment of cardiac failure containing a compound that inhibits a functional expression of ASK1 protein in a cardiomyocyte, and a method for screening the drug.

WO2009027283 discloses triazolopyridine compounds, methods for preparation thereof and methods for treating autoimmune disorders, inflammatory diseases, cardiovascular diseases and neurodegenerative diseases.

SUMMARY OF THE INVENTION

Accordingly, the present invention provides novel compounds that function as ASK1 inhibitors. In a first aspect, the invention relates to compounds of Formula (I):

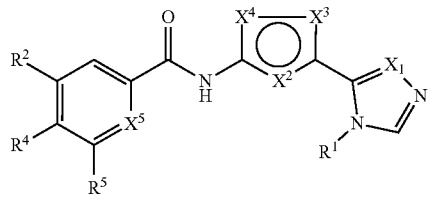

(I)

wherein:

$R^1$ is alkyl of 1-6 carbon atoms, alkenyl of 1-6 carbon atoms, alkynyl of 1-6 carbon atoms, cycloalkyl of 3-6 carbon atoms, aryl, heteroaryl, or heterocyclyl, all of which are optionally substituted with 1, 2, 3, or 4 substituents selected from halo, hydroxyl, oxo, alkyl, cycloalkyl, heterocyclyl, aryl, aryloxy, —$NO_2$, $R^6$, —C(O)—$R^6$, —OC(O)—$R^6$—C(O)—O—$R^6$, —C(O)—N($R^6$)($R^7$), —OC(O)—N($R^6$)($R^7$), —S—$R^6$, —S(═O)—$R^6$, —S(═O)$_2$$R^6$, —S(═O)$_2$—N($R^6$)($R^7$), —S(═O)$_2$—O—$R^6$, —N($R^6$)($R^7$), —N($R^6$)—C(O)—$R^7$, —N($R^6$)—C(O)—O—$R^7$, —N($R^6$)—C(O)—N($R^6$)($R^7$), —N($R^6$)—S(═O)$_2$—$R^6$, —CN, and —O—$R^6$, wherein alkyl, cycloalkyl, heterocyclyl, aryl, and aryloxy are optionally substituted by 1, 2, or 3 substituents selected from alkyl, cycloalkyl, alkoxy, hydroxyl, and halo;

wherein $R^6$ and $R^7$ are independently selected from the group consisting of hydrogen, $C_1$-$C_{15}$ alkyl, cycloalkyl, heterocyclyl, aryl, and heteroaryl, all of which are optionally substituted with 1-3 substituents selected from halo, alkyl, mono- or dialkylamino, alkyl or aryl or heteroaryl amide, —CN, lower alkoxy, —$CF_3$, aryl, and heteroaryl; or $R^6$ and $R^7$ when taken together with the nitrogen to which they are attached form a heterocycle;

$R^2$ is aryl, heteroaryl, or heterocyclyl, all of which are optionally substituted with one or more substituents selected from alkyl, alkoxy, cycloalkyl, cycloalkylalkyl, aryl, arylalkyl, heteroaryl, heteroarylalkyl, heterocyclyl, heterocyclylalkyl, halo, oxo, —$NO_2$, haloalkyl, haloalkoxy, —CN, —O—$R^6$, —O—C(O)—$R^6$, —O—C(O)—N($R^6$)($R^7$), —S—$R^6$, —N($R^6$)($R^7$), —S(═O)—$R^6$, —S(═O)$_2$$R^6$, —S(═O)$_2$—N($R^6$)($R^7$), —S(═O)$_2$—O—$R^6$, —N($R^6$)—C(O)—$R^7$, —N($R^6$)—C(O)—O—$R^7$, —N($R^6$)—C(O)—N($R^6$)($R^7$), —C(O)—$R^6$, —C(O)—O—$R^6$, —C(O)—N($R^6$)($R^7$), and —N($R^6$)—S(═O)$_2$—$R^7$, wherein the alkyl, alkoxy, cycloalkyl, aryl, heteroaryl or heterocyclyl is further optionally substituted with one or more substituents selected from halo, oxo, —$NO_2$, alkyl, haloalkyl, haloalkoxy, —N($R^6$)($R^7$), —C(O)—$R^6$, —C(O)—O—$R^6$, —C(O)—N($R^6$)($R^7$), —CN, —O—$R^6$, cycloalkyl, aryl, heteroaryl and heterocyclyl;

with the proviso that the heteroaryl or heterocyclyl moiety includes at least one ring nitrogen atom;

$R^4$ and $R^5$ are independently hydrogen, halo, cyano, alkyl of 1-6 carbon atoms, alkoxy of 1-6 carbon atoms, or cycloalkyl of 3-6 carbon atoms, in which alkyl, alkoxy, and cycloalkyl are optionally substituted by halo or cycloalkyl of 3-8 carbon atoms;

$X^1$ and $X^5$ are independently C($R^3$) or N, in which each $R^3$ is independently hydrogen, halo, alkyl of 1-6 carbon atoms, alkoxy of 1-6 carbon atoms or cycloalkyl of 3-8 carbon atoms, wherein the alkyl or cycloalkyl is further optionally substituted with one or more substituents selected from halo, oxo, —$CF_3$, —O—$CF_3$, —N($R^6$)($R^7$), —C(O)—$R^6$, —C(O)—O—$R^7$, —C(O)—N($R^6$)($R^7$), —CN, —O—$R^6$;

$X^2$, $X^3$ and $X^4$ are independently C($R^3$), N, O, or S;

with the proviso that at least one of $X^2$, $X^3$, and $X^4$ is C($R^3$); and only one of $X^2$, $X^3$, and $X^4$ is O or S;

and the pharmaceutically acceptable salts thereof.

In a second aspect, the invention relates to a method of using the compounds of Formula (I) in the treatment of a disease or condition in a mammal that is amenable to treatment by an ASK1 inhibitor. Such diseases include autoimmune disorders, inflammatory diseases, cardiovascular diseases (including diabetes, diabetic nephropathy, and other complications of diabetes), cardio-renal diseases, including kidney disease, fibrotic diseases, respiratory diseases (including COPD, idiopathic pulmonary fibrosis (IPF), and acute lung injury), acute and chronic liver diseases, and neurodegenerative diseases.

In a third aspect, the invention relates to pharmaceutical formulations comprising a therapeutically effective amount of a compound of Formula (I) and at least one pharmaceutically acceptable excipient.

In a fourth aspect, the invention relates to methods of preparing the compounds of Formula (I).

Non-limiting examples of $R^2$ are shown below:

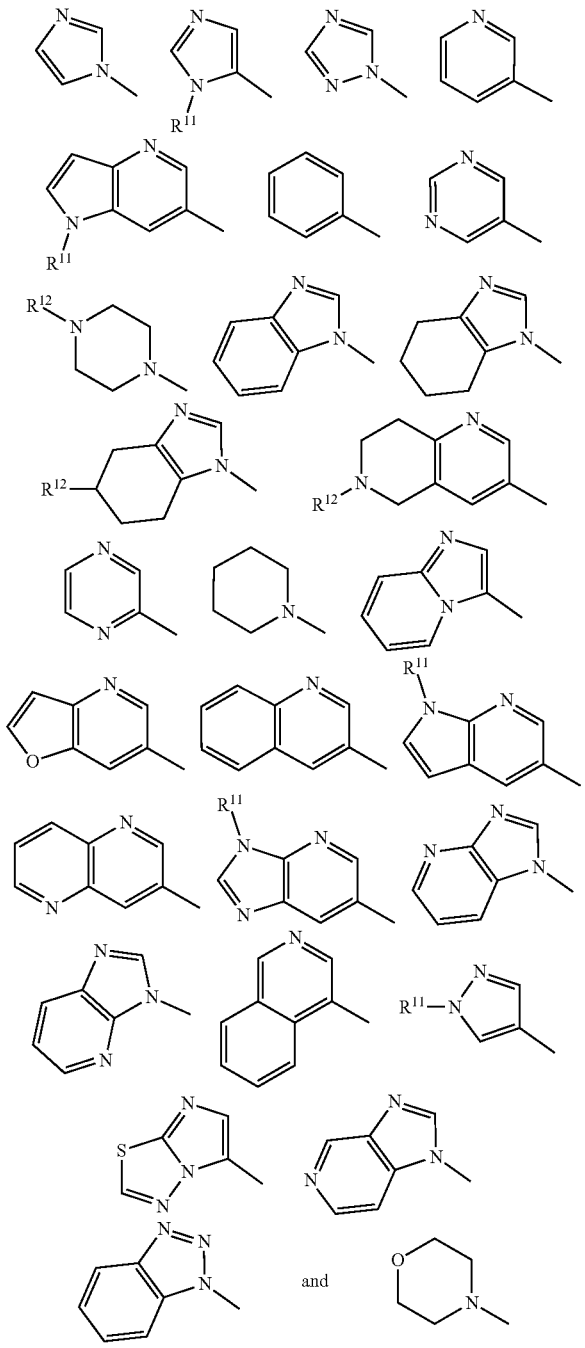

in which:

$R^{11}$ is hydrogen, alkyl, or cycloalkyl, wherein alkyl and cycloalkyl are optionally substituted by hydroxyl or halo;

$R^{12}$ is hydrogen, alkyl, cycloalkyl, —S(=O)—$R^6$ or —S(=O)$_2$$R^6$, wherein alkyl and cycloalkyl are optionally substituted by hydroxyl or halo.

One embodiment of the invention includes those compounds of Formula (I) in which $X^1$ is N. Within this embodiment are compounds of Formula (I) in which $R^1$ is optionally substituted alkyl having 1, 2, 3, 4, 5, or 6 carbon atoms or optionally substituted cycloalkyl having 3, 4, 5, or 6 carbon atoms and $X^5$ is C($R^3$), in which $R^3$ is hydrogen, halo, alkyl of 1, 2, 3, 4, 5, or 6 carbon atoms, or alkoxy of 1, 2, 3, 4, 5, or 6 carbon atoms. Within this group are compounds of Formula (I) in which $R^2$ is optionally substituted heteroaryl, especially where $R^2$ is imidazolyl or pyridyl, both of which are optionally substituted by 1, 2, or 3 substituents chosen from halo, alkyl of 1, 2, 3 or 4 carbon atoms, alkoxy of 1, 2, 3 or 4 carbon atoms, and cycloalkyl of 3, 4, 5, 6 carbon atoms, and $X^2$ is C($R^3$) or N, and $X^3$ and $X^4$ are C($R^3$) or S.

Within this subgroup are compounds of Formula (I) in which R is hydrogen or methoxy and $R^1$ is cycloalkyl having 3, 4, 5, 6, 7 or 8 carbon atoms, $X^3$ is S, $X^4$ is C(H), and $X^5$ is C($R^3$), in which $R^3$ is hydrogen or methoxy.

Another embodiment of the invention includes those compounds of Formula (I) in which $R^1$ is optionally substituted alkyl having 1, 2, 3, 4, 5, or 6 carbon atoms, or optionally substituted cycloalkyl having 3, 4, 5, or 6 carbon atoms and $X^5$ is N. Within this embodiment are compounds of Formula (I) in which $R^2$ is phenyl or heteroaryl, both of which are optionally substituted by 1, 2, or 3 substituents chosen from halo, alkyl of 1, 2, 3 or 4 carbon atoms, alkoxy of 1, 2, 3 or 4 carbon atoms, and cycloalkyl of 3, 4, 5 or 6 carbon atoms, particularly where $X^2$ is C($R^3$) or N, and $X^3$ and $X^4$ are C($R^3$) or S.

Within this group is a subgroup that includes compounds of Formula (I) in which $R^1$ is alkyl optionally substituted by 1, 2 or 3 substituents chosen from hydroxyl, halo, cycloalkyl of 3, 4, 5 or 6 carbon atoms, and phenyl, $X^2$ is CH, $X^3$ is S, and $X^4$ is CH.

Another subgroup includes compounds of Formula (I) in which $R^1$ is cycloalkyl optionally substituted by 1, 2 or 3 substituents chosen from hydroxyl, halo, cycloalkyl of 3-6 carbon atoms, and phenyl, $X^2$ is N, $X^3$ is S, and $X^4$ is CH.

Another subgroup includes compounds of Formula (I) in which $R^1$ is cycloalkyl optionally substituted by 1, 2 or 3 substituents chosen from hydroxyl, halo, cycloalkyl of 3-6 carbon atoms, and phenyl, $X^2$ is N, $X^3$ is CH, and $X^4$ is S.

The compounds of the invention include, but are not limited to, those compounds named below:

N-(5-(4-cyclopropyl-4H-1,2,4-triazol-3-yl)thiophen-3-yl)-4-phenylpicolinamide;

4-(4-cyclopropyl-1H-imidazol-1-yl)-N-(5-(4-cyclopropyl-4H-1,2,4-triazol-3-yl)thiophen-3-yl)picolinamide;

N-(5-(4-cyclopropyl-4H-1,2,4-triazol-3-yl)thiophen-3-yl)-3,4'-bipyridine-2'-carboxamide;

6-cyclopropyl-N-(5-(4-cyclopropyl-4H-1,2,4-triazol-3-yl) thiophen-3-yl)-3,4'-bipyridine-2'-carboxamide;

(S)-4-(4-cyclopropyl-1H-imidazol-1-yl)-N-(5-(4-(3-methylbutan-2-yl)-4H-1,2,4-triazol-3-yl)thiophen-3-yl)picolinamide;

(S)-4-(4-cyclopropyl-1H-imidazol-1-yl)-N-(5-(4-(1,1,1-trifluoropropan-2-yl)-4H-1,2,4-triazol-3-yl)thiophen-3-yl) picolinamide;

(S)-4-(4-cyclopropyl-1H-imidazol-1-yl)-N-(5-(4-(1-phenylethyl)-4H-1,2,4-triazol-3-yl)thiophen-3-yl)picolinamide;

4-(4-cyclopropyl-1H-imidazol-1-yl)-N-(5-(4-(3-hydroxybutan-2-yl)-4H-1,2,4-triazol-3-yl)thiophen-3-yl)picolinamide;

4-(4-cyclopropyl-1H-imidazol-1-yl)-N-(5-(4-(4,4,4-trifluoro-3-hydroxybutan-2-yl)-4H-1,2,4-triazol-3-yl)thiophen-3-yl)picolinamide;

6-cyclopropyl-N-(2-(4-cyclopropyl-4H-1,2,4-triazol-3-yl) thiazol-4-yl)-3,4'-bipyridine-2'-carboxamide;

N-(2-(4-cyclopropyl-4H-1,2,4-triazol-3-yl)thiazol-4-yl)-3,4'-bipyridine-2'-carboxamide;

4-(1H-benzo[d]imidazol-1-yl)-N-(4-(4-cyclopropyl-4H-1,2,4-thiazol-3-yl)thiazol-2-yl)picolinamide;

N-(4-(4-cyclopropyl-4H-1,2,4-triazol-3-yl)thiazol-2-yl)-3,4'-bipyridine-2'-carboxamide;

N-(4-(4-cyclopropyl-4H-1,2,4-triazol-3-yl)thiazol-2-yl)-6-methoxy-3,4'-bipyridine-2'-carboxamide;

3-(4-cyclopropyl-1H-imidazol-1-yl)-N-(2-(4-cyclopropyl-4H-1,2,4-triazol-3-yl)thiazol-4-yl)benzamide;

4-(4-cyclopropyl-1H-imidazol-1-yl)-N-(2-(4-cyclopropyl-4H-1,2,4-triazol-3-yl)thiazol-4-yl)picolinamide;

N-(5-(4-cyclopropyl-4H-1,2,4-triazol-3-yl)thiophen-3-yl)-4-(4-cyclopropyl-5-methyl-1H-imidazol-1-yl)picolinamide;

N-(5-(4-cyclopropyl-4H-1,2,4-triazol-3-yl)thiophen-3-yl)-4-(4-(pyridin-2-yl)-1H-imidazol-1-yl)picolinamide;

N-(5-(4-cyclopropyl-4H-1,2,4-triazol-3-yl)thiophen-3-yl)-4-(4-(pyridin-3-yl)-1H-imidazol-1-yl)picolinamide;

N-(5-(4-cyclopropyl-4H-1,2,4-triazol-3-yl)thiophen-3-yl)-5-(6-cyclopropylpyridin-3-yl)-2-methoxybenzamide;

N-(5-(4-cyclopropyl-4H-1,2,4-triazol-3-yl)thiophen-3-yl)-5-(6-cyclopropylpyridin-3-yl)-2,4-dimethoxybenzamide;

5-(4-cyclopropyl-1H-imidazol-1-yl)-N-(5-(4-cyclopropyl-4H-1,2,4-triazol-3-yl)thiophen-3-yl)-2-methoxybenzamide;

5-(4-cyclopropyl-1H-imidazol-1-yl)-N-(2-(4-cyclopropyl-4H-1,2,4-triazol-3-yl)thiazol-4-yl)-2-methoxybenz amide;

4-(4-bromo-1H-imidazol-1-yl)-N-(5-(4-cyclopropyl-4H-1,2,4-triazol-3-yl)thiophen-3-yl)picolinamide;

4-(4-cyclopropyl-1H-imidazol-1-yl)-N-(2-(4-isopropyl-4H-1,2,4-triazol-3-yl)thiazol-4-yl)picolinamide;

5-(4-cyclopropyl-1H-imidazol-1-yl)-N-(5-(4-cyclopropyl-4H-1,2,4-triazol-3-yl)thiophen-3-yl)-2-fluorobenzamide;

(S)-4-(4-cyclopropyl-1H-imidazol-1-yl)-N-(2-(4-(3-methylbutan-2-yl)-4H-1,2,4-triazol-3-yl)thiazol-4-yl)picolinamide;

5-(4-cyclopropyl-1H-imidazol-1-yl)-N-(2-(4-cyclopropyl-4H-1,2,4-triazol-3-yl)thiazol-4-yl)-2-fluorobenzamide;

(R)-4-(4-cyclopropyl-1H-imidazol-1-yl)-N-(5-(4-(2,2-dimethylcyclopropyl)-4H-1,2,4-triazol-3-yl)thiophen-3-yl) picolinamide;

(S)-4-(4-cyclopropyl-1H-imidazol-1-yl)-N-(5-(4-(2,2-dimethylcyclopropyl)-4H-1,2,4-triazol-3-yl)thiophen-3-yl) picolinamide;

4-(4-cyclopropyl-1H-imidazol-1-yl)-N-(2-(4-cyclopropyl-4H-1,2,4-triazol-3-yl)thiazol-4-yl)-5-methylpicolinamide;

4-(4-cyclopropyl-1H-imidazol-1-yl)-N-(5-(4-cyclopropyl-4H-1,2,4-triazol-3-yl)thiophen-3-yl)-5-methylpicolinamide;

(S)-4-(4-cyclopropyl-1H-imidazol-1-yl)-N-(2-(4-(1,1,1-trifluoropropan-2-yl)-4H-1,2,4-triazol-3-yl)thiazol-4-yl)picolinamide;

4-(4-tert-butyl-1H-imidazol-1-yl)-N-(5-(4-cyclopropyl-4H-1,2,4-triazol-3-yl)thiophen-3-yl)picolinamide (S)-4-(4-cyclopropyl-1H-imidazol-1-yl)-5-methyl-N-(2-(4-(1,1,1-trifluoropropan-2-yl)-4H-1,2,4-triazol-3-yl)thiazol-4-yl)picolinamide;

(S)-4-(4-tert-butyl-1H-imidazol-1-yl)-5-methyl-N-(2-(4-(1,1,1-trifluoropropan-2-yl)-4H-1,2,4-triazol-3-yl)thiazol-4-yl)picolinamide;

3-(4-cyclopropyl-1H-imidazol-1-yl)-N-(5-(4-cyclopropyl-4H-1,2,4-triazol-3-yl)thiophen-3-yl)benzamide;

5-(4-cyclopropyl-1H-imidazol-1-yl)-N-(5-(4-cyclopropyl-4H-1,2,4-triazol-3-yl)thiophen-3-yl)-2-methoxybenzamide;

5-(4-cyclopropyl-1H-imidazol-1-yl)-N-(5-(4-cyclopropyl-4H-1,2,4-triazol-3-yl)thiophen-3-yl)-2,4-dimethoxybenzamide;

5-(4-cyclopropyl-1H-imidazol-1-yl)-N-(5-(4-cyclopropyl-4H-1,2,4-triazol-3-yl)thiophen-3-yl)-2-fluorobenzamide;

5-(4-cyclopropyl-1H-imidazol-1-yl)-N-(5-(4-cyclopropyl-4H-1,2,4-triazol-3-yl)thiophen-3-yl)-2-fluoro-4-methoxybenzamide;

N-(5-(4-cyclopropyl-4H-1,2,4-triazol-3-yl)thiophen-3-yl)-5-(6-cyclopropylpyridin-3-yl)-2-methoxybenzamide;

N-(5-(4-cyclopropyl-4H-1,2,4-triazol-3-yl)thiophen-3-yl)-5-(6-cyclopropylpyridin-3-yl)-2,4-dimethoxybenzamide;

N-(5-(4-cyclopropyl-4H-1,2,4-triazol-3-yl)thiophen-3-yl)-5-(6-cyclopropylpyridin-3-yl)-2-fluorobenzamide;

5-(4-cyclopropyl-1H-imidazol-1-yl)-N-(2-(4-cyclopropyl-4H-1,2,4-triazol-3-yl)thiazol-4-yl)-2-methoxybenzamide;

5-(4-cyclopropyl-1H-imidazol-1-yl)-N-(2-(4-cyclopropyl-4H-1,2,4-triazol-3-yl)thiazol-4-yl)-2,4-dimethoxybenzamide;

5-(4-cyclopropyl-1H-imidazol-1-yl)-N-(2-(4-cyclopropyl-4H-1,2,4-triazol-3-yl)thiazol-4-yl)-2-fluorobenzamide;

5-(4-cyclopropyl-1H-imidazol-1-yl)-N-(2-(4-cyclopropyl-4H-1,2,4-triazol-3-yl)thiazol-4-yl)-2-fluoro-4-methoxybenzamide;

N-(2-(4-cyclopropyl-4H-1,2,4-triazol-3-yl)thiazol-4-yl)-5-(6-cyclopropylpyridin-3-yl)-2-methoxybenzamide;

N-(2-(4-cyclopropyl-4H-1,2,4-triazol-3-yl)thiazol-4-yl)-5-(6-cyclopropylpyridin-3-yl)-2,4-dimethoxybenzamide;

N-(2-(4-cyclopropyl-4H-1,2,4-triazol-3-yl)thiazol-4-yl)-5-(6-cyclopropylpyridin-3-yl)-2-fluorobenzamide; and N-(2-(4-cyclopropyl-4H-1,2,4-triazol-3-yl)thiazol-4-yl)-5-(6-cyclopropylpyridin-3-yl)-2-fluoro-4-methoxybenzamide.

DETAILED DESCRIPTION OF THE INVENTION

Definitions and General Parameters

As used in the present specification, the following words and phrases are generally intended to have the meanings as set forth below, except to the extent that the context in which they are used indicates otherwise.

The term "alkyl" refers to a monoradical branched or unbranched saturated hydrocarbon chain having from 1 to 20 carbon atoms. This term is exemplified by groups such as methyl, ethyl, n-propyl, iso-propyl, n-butyl, iso-butyl, t-butyl, n-hexyl, n-decyl, tetradecyl, and the like.

The term "substituted alkyl" refers to:

1) an alkyl group as defined above, having 1, 2, 3, 4 or 5 substituents, (typically 1, 2, or 3 substituents) selected from the group consisting of alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO-alkyl, —SO-aryl, —SO-heteroaryl, —$SO_2$-alkyl, $SO_2$-aryl and —$SO_2$-heteroaryl. Unless otherwise constrained by the definition, all substituents may optionally be further substituted by 1, 2, or 3 substituents chosen from alkyl, carboxy, carboxyalkyl, aminocarbonyl, hydroxy, alkoxy, halogen, $CF_3$, amino, substituted amino, cyano, and —$S(O)_nR$, where R is alkyl, aryl, or heteroaryl and n is 0, 1 or 2; or 2) an alkyl group as defined above that is interrupted by 1-10 atoms (e.g. 1, 2, 3, 4, or 5 atoms) independently chosen from oxygen, sulfur and NRa—, where Ra is chosen from hydrogen, alkyl, cycloalkyl, alkenyl, cycloalkenyl, alkynyl, aryl, heteroaryl and heterocyclyl. All substituents may be optionally further substituted by alkyl, alkoxy, halogen, $CF_3$, amino, substituted amino, cyano, or —$S(O)_nR$, in which R is alkyl, aryl, or heteroaryl and n is 0, 1 or 2; or 3) an alkyl group as defined above that has both 1, 2, 3, 4 or 5 substituents as defined above and is also interrupted by 1-10 atoms (e.g. 1, 2, 3, 4, or 5 atoms) as defined above.

The term "lower alkyl" refers to a monoradical branched or unbranched saturated hydrocarbon chain having 1, 2, 3, 4, 5, or 6 carbon atoms. This term is exemplified by groups such as methyl, ethyl, n-propyl, iso-propyl, n-butyl, iso-butyl, t-butyl, n-hexyl, and the like.

The term "substituted lower alkyl" refers to lower alkyl as defined above having 1 to 5 substituents (typically 1, 2, or 3 substituents), as defined for substituted alkyl, or a lower alkyl group as defined above that is interrupted by 1, 2, 3, 4, or 5 atoms as defined for substituted alkyl, or a lower alkyl group as defined above that has both 1, 2, 3, 4 or 5 substituents as defined above and is also interrupted by 1, 2, 3, 4, or 5 atoms as defined above.

The term "alkylene" refers to a diradical of a branched or unbranched saturated hydrocarbon chain, typically having from 1 to 20 carbon atoms (e.g. 1-10 carbon atoms, or 1, 2, 3, 4, 5 or 6 carbon atoms). This term is exemplified by groups such as methylene (—$CH_2$—), ethylene (—$CH_2CH_2$—), the propylene isomers (e.g., —$CH_2CH_2CH_2$-and-$CH(CH_3)CH_2$—), and the like.

The term "lower alkylene" refers to a diradical of a branched or unbranched saturated hydrocarbon chain, typically having 1, 2, 3, 4, 5, or 6 carbon atoms.

The term "substituted alkylene" refers to:

(1) an alkylene group as defined above having 1, 2, 3, 4, or 5 substituents (typically 1, 2, or 3 substituents) selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO-alkyl, —SO-aryl, —SO-heteroaryl, —$SO_2$-alkyl, $SO_2$-aryl and —$SO_2$-heteroaryl. Unless otherwise constrained by the definition, all substituents may optionally be further substituted by 1, 2, or 3 substituents chosen from alkyl, carboxy, carboxyalkyl, aminocarbonyl, hydroxy, alkoxy, halogen, $CF_3$, amino, substituted amino, cyano, and —$S(O)_nR$, where R is alkyl, aryl, or heteroaryl and n is 0, 1 or 2; or (2) an alkylene group as defined above that is interrupted by 1-10 groups (e.g. 1, 2, 3, 4, or 5 groups) independently chosen from —O—, —S—, sulfonyl, —C(O)—, —C(O)O—, —C(O)N—, and —NRa—, where Ra is chosen from hydrogen, optionally substituted alkyl, cycloalkyl, cycloalkenyl, aryl, heteroaryl and heterocyclyl; or (3) an alkylene group as defined above that has both 1, 2, 3, 4 or 5 substituents as defined above and is also interrupted by 1-10 groups as defined above. Examples of substituted alkylenes are chloromethylene (—CH(Cl)—), aminoethylene (—CH($NH_2$)$CH_2$—), methylaminoethylene (—CH(NHMe)$CH_2$—), 2-carboxypropylene isomers (—$CH_2$CH($CO_2$H)$CH_2$—), ethoxyethyl (—$CH_2CH_2$O—$CH_2CH_2$—), ethylmethylaminoethyl (—$CH_2CH_2$—N($CH_3$)—$CH_2CH_2$—), 1-ethoxy-2-(2-ethoxy-ethoxy)ethane (—$CH_2CH_2$O—$CH_2CH_2$—O$CH_2CH_2$—O$CH_2CH_2$—), and the like.

The term "aralkyl" or "arylalkyl" refers to an aryl group covalently linked to an alkylene group, where aryl and alkylene are defined herein. "Optionally substituted aralkyl" refers to an optionally substituted aryl group covalently linked to an optionally substituted alkylene group. Such aralkyl groups are exemplified by benzyl, phenylethyl, 3-(4-methoxyphenyl)propyl, and the like.

The term "alkoxy" refers to the group R—O—, where R is optionally substituted alkyl or optionally substituted cycloalkyl, or R is a group —Y—Z, in whichY is optionally substituted alkylene and Z is optionally substituted alkenyl, optionally substituted alkynyl; or optionally substituted cycloalkenyl, where alkyl, alkenyl, alkynyl, cycloalkyl and cycloalkenyl are as defined herein. Typical alkoxy groups are alkyl-O— and include, by way of example, methoxy, ethoxy, n-propoxy, iso-propoxy, n-butoxy, tert-butoxy, sec-butoxy, n-pentoxy, n-hexyloxy, 1,2-dimethylbutoxy, and the like.

The term "lower alkoxy" refers to the group R—O— in which R is optionally substituted lower alkyl as defined above. This term is exemplified by groups such as methoxy, ethoxy, n-propoxy, iso-propoxy, n-butoxy, iso-butoxy, t-butoxy, n-hexyloxy, and the like.

The term "alkylthio" refers to the group R—S—, where R is as defined for alkoxy.

The term "alkenyl" refers to a monoradical of a branched or unbranched unsaturated hydrocarbon group typically having from 2 to 20 carbon atoms (more typically from 2 to 10 carbon atoms, e.g. 2 to 6 carbon atoms) and having from 1 to 6 carbon-carbon double bonds, e.g. 1, 2, or 3 carbon-carbon double bonds. Typical alkenyl groups include ethenyl (or vinyl, i.e. —CH═$CH_2$), 1-propylene (or allyl, —$CH_2$CH═$CH_2$), isopropylene (—C($CH_3$)═$CH_2$), bicyclo[2.2.1]heptene, and the like. In the event that alkenyl is attached to nitrogen, the double bond cannot be alpha to the nitrogen.

The term "lower alkenyl" refers to alkenyl as defined above having from 2 to 6 carbon atoms.

The term "substituted alkenyl" refers to an alkenyl group as defined above having 1, 2, 3, 4 or 5 substituents (typically 1, 2, or 3 substituents), selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO-alkyl, —SO-aryl, —SO-heteroaryl, —$SO_2$-alkyl, $SO_2$-aryl and —$SO_2$-heteroaryl. Unless otherwise constrained by the definition, all substituents may optionally be further substituted by 1, 2, or 3 substituents chosen from alkyl, carboxy, carboxyalkyl, aminocarbonyl, hydroxy, alkoxy, halogen, $CF_3$, amino, substituted amino, cyano, and —S(O)$_n$R, where R is alkyl, aryl, or heteroaryl and n is 0, 1 or 2.

The term "alkynyl" refers to a monoradical of an unsaturated hydrocarbon, typically having from 2 to 20 carbon atoms (more typically from 2 to 6 carbon atoms) and having e.g. 1, 2, or 3 carbon-carbon triple bonds. Typical alkynyl groups include ethynyl (—C≡CH), propargyl (or propynyl, —C≡CCH3), and the like. In the event that alkynyl is attached to nitrogen, the triple bond cannot be alpha to the nitrogen.

The term "substituted alkynyl" refers to an alkynyl group as defined above having 1, 2, 3, 4 or 5 substituents (typically 1, 2, or 3 substituents), selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO-alkyl, —SO-aryl, —SO-heteroaryl, —$SO_2$-alkyl, $SO_2$-aryl and —$SO_2$-heteroaryl. Unless otherwise constrained by the definition, all substituents may optionally be further substituted by 1, 2, or 3 substituents chosen from alkyl, carboxy, carboxyalkyl, aminocarbonyl, hydroxy, alkoxy, halogen, $CF_3$, amino, substituted amino, cyano, and —S(O)$_n$R, where R is alkyl, aryl, or heteroaryl and n is 0, 1 or 2.

The term "aminocarbonyl" refers to the group —C(O)NRR where each R is independently hydrogen, alkyl, cycloalkyl, aryl, heteroaryl, heterocyclyl or where both R groups are joined to form a heterocyclic group (e.g., morpholino). Unless otherwise constrained by the definition, all substituents may optionally be further substituted by 1, 2, or 3 substituents chosen from alkyl, carboxy, carboxyalkyl, aminocarbonyl, hydroxy, alkoxy, halogen, $CF_3$, amino, substituted amino, cyano, and —S(O)$_n$R, where R is alkyl, aryl, or heteroaryl and n is 0, 1 or 2.

The term "ester" or "carboxyester" refers to the group —C(O)OR, where R is alkyl, cycloalkyl, aryl, heteroaryl, or heterocyclyl, which may be optionally further substituted by alkyl, alkoxy, halogen, $CF_3$, amino, substituted amino, cyano, or —S(O)$_n$Ra, in which Ra is alkyl, aryl, or heteroaryl and n is 0, 1 or 2.

The term "acylamino" refers to the group —NRC(O)R where each R is independently hydrogen, alkyl, aryl, heteroaryl, or heterocyclyl. All substituents may be optionally further substituted by alkyl, alkoxy, halogen, $CF_3$, amino, substituted amino, cyano, or —S(O)$_n$R, in which R is alkyl, aryl, or heteroaryl and n is 0, 1 or 2.

The term "acyloxy" refers to the groups —OC(O)-alkyl, —OC(O)-cycloalkyl, —OC(O)-aryl, —OC(O)-heteroaryl, and —OC(O)-heterocyclyl. Unless otherwise constrained by the definition, all substituents may optionally be further substituted by 1, 2, or 3 substituents chosen from alkyl, carboxy, carboxyalkyl, aminocarbonyl, hydroxy, alkoxy, halogen, $CF_3$, amino, substituted amino, cyano, and —S(O)$_n$R, where R is alkyl, aryl, or heteroaryl and n is 0, 1 or 2.

The term "aryl" refers to an aromatic carbocyclic group of 6 to 20 carbon atoms having a single ring (e.g., phenyl) or multiple rings (e.g., biphenyl), or multiple condensed (fused) rings (e.g., naphthyl, fluorenyl, and anthryl). Typical aryls include phenyl, fluorenyl, naphthyl, anthryl, 1,2,3,4-tetrahydronaphthalene, and the like.

Unless otherwise constrained by the definition for the aryl substituent, such aryl groups can optionally be substituted with 1, 2, 3, 4 or 5 substituents (typically 1, 2, or 3 substituents), selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO-alkyl, —SO-aryl, —SO-heteroaryl, —$SO_2$-alkyl, $SO_2$-aryl and —$SO_2$-heteroaryl. Unless otherwise constrained by the definition, all substituents may optionally be further substituted by 1, 2, or 3 substituents chosen from alkyl, carboxy, carboxyalkyl, aminocarbonyl, hydroxy, alkoxy, halogen, $CF_3$, amino, substituted amino, cyano, and —$S(O)_nR$, where R is alkyl, aryl, or heteroaryl and n is 0, 1 or 2.

The term "aryloxy" refers to the group aryl-O— wherein the aryl group is as defined above, and includes optionally substituted aryl groups as also defined above. The term "arylthio" refers to the group R—S—, where R is as defined for aryl.

The term "amino" refers to the group —$NH_2$.

The term "substituted amino" refers to the group —NRR where each R is independently selected from the group consisting of hydrogen, alkyl, cycloalkyl, aryl, heteroaryl and heterocyclyl provided that both R groups are not hydrogen, or a group —Y—Z, in which Y is optionally substituted alkylene and Z is alkenyl, cycloalkenyl, or alkynyl. Unless otherwise constrained by the definition, all substituents may optionally be further substituted by 1, 2, or 3 substituents chosen from alkyl, carboxy, carboxyalkyl, aminocarbonyl, hydroxy, alkoxy, halogen, $CF_3$, amino, substituted amino, cyano, and —$S(O)_nR$, where R is alkyl, aryl, or heteroaryl and n is 0, 1 or 2.

The term "carboxyalkyl" refers to the groups —C(O)O-alkyl, —C(O)O-cycloalkyl, where alkyl and cycloalkyl are as defined herein, and may be optionally further substituted by alkyl, alkenyl, alkynyl, alkoxy, halogen, $CF_3$, amino, substituted amino, cyano, or —$S(O)_nR$, in which R is alkyl, aryl, or heteroaryl and n is 0, 1 or 2.

The term "cycloalkyl" refers to cyclic alkyl groups of from 3 to 20 carbon atoms having a single cyclic ring or multiple condensed or bridged rings. Such cycloalkyl groups include, by way of example, single ring structures such as cyclopropyl, cyclobutyl, cyclopentyl, cyclooctyl, and the like, or multiple ring structures such as adamantanyl, and bicyclo[2.2.1]heptane, or cyclic alkyl groups to which is fused an aryl group, for example indan, and the like.

The term "substituted cycloalkyl" refers to cycloalkyl groups having 1, 2, 3, 4 or 5 substituents (typically 1, 2, or 3 substituents), selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO-alkyl, —SO-aryl, —SO-heteroaryl, —$SO_2$-alkyl, $SO_2$-aryl and —$SO_2$-heteroaryl. The term "substituted cycloalkyl" also includes cycloalkyl groups wherein one or more of the annular carbon atoms of the cycloalkyl group is a carbonyl group (i.e. an oxygen atom is oxo to the ring). Unless otherwise constrained by the definition, all substituents may optionally be further substituted by 1, 2, or 3 substituents chosen from alkyl, carboxy, carboxyalkyl, aminocarbonyl, hydroxy, alkoxy, halogen, $CF_3$, amino, substituted amino, cyano, and —$S(O)_nR$, where R is alkyl, aryl, or heteroaryl and n is 0, 1 or 2.

The term "halogen" or "halo" refers to fluoro, bromo, chloro, and iodo.

The term "haloalkyl" refers to alkyl of 1-6 carbon atoms substituted by 1, 2, 3, 4, 5, or 6 halo atoms.

The term "acyl" denotes a group —C(O)R, in which R is hydrogen, optionally substituted alkyl, optionally substituted cycloalkyl, optionally substituted heterocyclyl, optionally substituted aryl, and optionally substituted heteroaryl.

The term "heteroaryl" refers to a group comprising 1 to 15 carbon atoms and 1 to 4 heteroatoms selected from oxygen, nitrogen, and sulfur within at least one ring.

The term "heteroaryl" is generic to the terms "aromatic heteroaryl" and "partially saturated heteroaryl".

The term "aromatic heteroaryl" refers to a heteroaryl in which at least one ring is aromatic. Examples of aromatic heteroaryls include pyridyl, thienyl, furanyl, pyrimidyl, imidazolyl, imidazopyridyl, pyranyl, pyrazolyl, pyrzolopyridyl, thiazolyl, thiadiazolyl, isothiazolyl, oxazolyl, isoxazoyl, pyrrolyl, pyridazinyl, pyrazinyl, quinolinyl, isoquinolinyl, benzofuranyl, dibenzofuranyl, dibenzothiophenyl, benzothienyl, indolyl, benzothiazolyl, benzooxazolyl, benzimidazolyl, isoindolyl, benzotriazolyl, purinyl, thianaphthenyl and pyrazinyl.

The term "partially saturated heteroaryl" refers to a heteroaryl having a structure equivalent to an underlying arouratic heteroaryl which has had one or more double bonds in an aromatic ring of the underlying aromatic heteroaryl saturated. Examples of partially saturated heteroaryls include dihydropyrrole, dihydropyridine, 4,5,6,7-tetrahydro-1H-imidazo[4,5-c]pyridine, and the like.

Unless otherwise constrained by the definition for the heteroaryl substituent, such heteroaryl groups can be optionally substituted with 1 to 5 substituents (typically 1, 2, or 3 substituents) selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl (an alkyl ester), arylthio, heteroaryl, heteroarylthio, heterocyclylthio, thiol, alkylthio, aryl, aryloxy, aralkyl, heteroaryl, aminosulfonyl, aminocarbonylamino, heteroaryloxy, heterocyclyl, heterocyclooxy, hydroxyamino, alkoxyamino, nitro, —SO-alkyl, —SO-aryl, —SO-heteroaryl, —$SO_2$-alkyl, $SO_2$-aryl and —$SO_2$-heteroaryl. Unless otherwise constrained by the definition, all substituents may optionally be further substituted by 1, 2, or 3 substituents chosen from alkyl, carboxy, carboxyalkyl, aminocarbonyl, hydroxy, alkoxy, halogen, $CF_3$, amino, substituted amino, cyano, and —$S(O)_nR$, where R is alkyl, aryl, or heteroaryl and n is 0, 1 or 2. Such heteroaryl groups can have a single ring (e.g., pyridyl or furyl) or multiple condensed rings (e.g., indolizinyl, benzothiazole, or benzothienyl). Examples of nitrogen heterocyclyls and heteroaryls include, but are not limited to, pyrrole, imidazole, pyrazole, pyridine, pyrazine, pyrimidine, pyridazine, indolizine, isoindole, indole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, and the like as well as N-alkoxy-nitrogen containing heteroaryl compounds.

The term "heteroaryloxy" refers to the group heteroaryl-O—.

The teem "heterocyclyl" refers to a monoradical saturated or partially unsaturated group having a single ring or multiple condensed or bridged rings, having from 1 to 40 carbon atoms and from 1 to 10 hetero atoms, preferably 1, 2, 3 or 4 heteroatoms, selected from nitrogen, sulfur, phosphorus, and/or oxygen within the ring. Heterocyclic groups can have a single ring or multiple condensed rings, and include tetrahydrofuranyl, morpholino, piperidinyl, piperazino, dihydropyridino, 4,5,6,7-tetrahydro-1H-benzo[d]imidazole, benzo[d]imidazole, 4,5,6,7-tetrahydro-1H-imidazo[4,5-c] pyridine, and the like.

Unless otherwise constrained by the definition for the heterocyclic substituent, such heterocyclic groups can be optionally substituted with 1, 2, 3, 4 or 5, and preferably 1, 2 or 3 substituents, selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO-alkyl, —SO-aryl, —SO-heteroaryl, —$SO_2$-alkyl, $SO_2$-aryl and —$SO_2$-heteroaryl. Unless otherwise constrained by the definition, all substituents may optionally be further substituted by 1-3 substituents chosen from alkyl, carboxy, carboxyalkyl, aminocarbonyl, hydroxy, alkoxy, halogen, $CF_3$, amino, substituted amino, cyano, and —$S(O)_nR$, where R is alkyl, aryl, or heteroaryl and n is 0, 1 or 2.

The term "thiol" refers to the group —SH.

The term "substituted alkylthio" refers to the group —S-substituted alkyl.

The term "heteroarylthiol" refers to the group —S-heteroaryl wherein the heteroaryl group is as defined above including optionally substituted heteroaryl groups as also defined above.

The term "sulfoxide" refers to a group —S(O)R, in which R is alkyl, aryl, or heteroaryl. "Substituted sulfoxide" refers to a group —S(O)R, in which R is substituted alkyl, substituted aryl, or substituted heteroaryl, as defined herein.

The term "sulfone" refers to a group —$S(O)_2R$, in which R is alkyl, aryl, or heteroaryl. "Substituted sulfone" refers to a group —$S(O)_2R$, in which R is substituted alkyl, substituted aryl, or substituted heteroaryl, as defined herein.

The term "keto" refers to a group —C(O)—. The term "thiocarbonyl" refers to a group —C(S)—. The term "carboxy" refers to a group —C(O)—OH. The term "oxo" refers to =O.

"Optional" or "optionally" means that the subsequently described event or circumstance may or may not occur, and that the description includes instances where said event or circumstance occurs and instances in which it does not.

A "substituted" group includes embodiments in which a monoradical substituent is bound to a single atom of the substituted group (e.g. forming a branch), and also includes embodiments in which the substituent may be a diradical bridging group bound to two adjacent atoms of the substituted group, thereby forming a fused ring on the substituted group.

A compound of a given Formula (e.g. the "compound of Formula (I)") is intended to encompass the compounds of the invention as disclosed, and the pharmaceutically acceptable salts, pharmaceutically acceptable esters, hydrates, polymorphs, and prodrugs of such compounds. Additionally, the compounds of the invention may possess one or more asymmetric centers, and can be produced as a racemic mixture or as individual enantiomers or diastereoisomers. The number of stereoisomers present in any given compound of a given Formula depends upon the number of asymmetric centers present (there are 2n stereoisomers possible where n is the number of asymmetric centers). The individual stereoisomers may be obtained by resolving a racemic or non-racemic mixture of an intermediate at some appropriate stage of the synthesis, or by resolution of the compound by conventional means. The individual stereoisomers (including individual enantiomers and diastereoisomers) as well as racemic and non-racemic mixtures of stereoisomers are encompassed within the scope of the present invention, all of which are intended to be depicted by the structures of this specification unless otherwise specifically indicated.

The invention also included compounds of Formula I in which from 1 to n hydrogens attached to a carbon atom is/are replaced by deuterium, in which n is the number of hydrogens in the molecule. Such compounds exhibit increased resistance to metabolism, and are thus useful for increasing the half life of any compound of Formula I when administered to a mammal See, for example, Foster, "Deuterium Isotope Effects in Studies of Drug Metabolism", Trends Pharmacol. Sci. 5(12):524-527 (1984). Such compounds are synthesized by means well known in the art, for example by employing starting materials in which one or more hydrogens have been replaced by deuterium.

"Isomers" are different compounds that have the same molecular formula.

"Stereoisomers" are isomers that differ only in the way the atoms are arranged in space.

"Enantiomers" are a pair of stereoisomers that are non-superimposable mirror images of each other. A 1:1 mixture of a pair of enantiomers is a "racemic" mixture. The term "(±)" is used to designate a racemic mixture where appropriate.

"Diastereoisomers" are stereoisomers that have at least two asymmetric atoms, but which are not mirror-images of each other.

Any formula or structure given herein, including Formula I compounds, is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the invention include isotopes of hydrogen, carbon, nitrogen, oxygen, phosphorous, fluorine, and chlorine, such as, but not limited to 2H (deuterium, D), 3H (tritium), 11C, 13C, 14C, 15N, 18F, 31P, 32P, 35S, 36Cl, and 125I. Various isotopically labeled compounds of the present invention, for example those into which radioactive isotopes such as 3H, 13C, and 14C are incorporated. Such isotopically labelled compounds may be useful in metabolic studies, reaction kinetic studies, detection or imaging techniques, such as positron emission tomography (PET) or single-photon emission computed tomography (SPECT) including drug or substrate tissue distribution assays, or in radioactive treatment of patients.

Deuterium labelled or substituted therapeutic compounds of the invention may have improved DMPK (drug metabolism and pharmacokinetics) properties, relating to distribution, metabolism, and excretion (ADME). Substitution with heavier isotopes such as deuterium may afford certain therapeutic advantages resulting from greater metabolic stability, for example increased in vivo half-life or reduced dosage requirements. An 18F labeled compound may be useful for PET or SPECT studies. Isotopically labeled compounds of this invention and prodrugs thereof can generally be prepared by carrying out the procedures disclosed in the schemes or in the examples and preparations described below by substituting a readily available isotopically labeled reagent for a non-isotopically labeled reagent. Further, substitution with heavier isotopes, particularly deuterium (i.e., 2H or D) may afford certain therapeutic advantages resulting from greater metabolic stability, for example increased in vivo half-life or reduced dosage requirements or an improvement in therapeutic index. It is understood that deuterium in this context is regarded as a substituent in the compound of the formula (I).

The concentration of such a heavier isotope, specifically deuterium, may be defined by an isotopic enrichment factor. In the compounds of this invention any atom not specifically designated as a particular isotope is meant to represent any stable isotope of that atom. Unless otherwise stated, when a position is designated specifically as "H" or "hydrogen", the position is understood to have hydrogen at its natural abundance isotopic composition. Accordingly, in the compounds of this invention any atom specifically designated as a deuterium (D) is meant to represent deuterium.

The absolute stereochemistry is specified according to the Calm Ingold Prelog R S system. When the compound is a pure enantiomer the stereochemistry at each chiral carbon may be specified by either R or S. Resolved compounds whose absolute configuration is unknown are designated (+) or (−) depending on the direction (dextro- or laevorotary) that they rotate the plane of polarized light at the wavelength of the sodium D line.

The term "therapeutically effective amount" refers to an amount that is sufficient to effect treatment, as defined below, when administered to a mammal in need of such treatment. The therapeutically effective amount will vary depending upon the subject and disease condition being treated, the weight and age of the subject, the severity of the disease condition, the manner of administration and the like, which can readily be determined by one of ordinary skill in the art.

The term "treatment" or "treating" means any treatment of a disease in a mammal, including:

(i) preventing the disease, that is, causing the clinical symptoms of the disease not to develop;

(ii) inhibiting the disease, that is, arresting the development of clinical symptoms; and/or (iii) relieving the disease, that is, causing the regression of clinical symptoms.

In many cases, the compounds of this invention are capable of forming acid and/or base salts by virtue of the presence of amino and/or carboxyl groups or groups similar thereto.

The term "pharmaceutically acceptable salt" of a given compound refers to salts that retain the biological effectiveness and properties of the given compound, and which are not biologically or otherwise undesirable. Pharmaceutically acceptable base addition salts can be prepared from inorganic and organic bases. Salts derived from inorganic bases include, by way of example only, sodium, potassium, lithium, ammonium, calcium and magnesium salts. Salts derived from organic bases include, but are not limited to, salts of primary, secondary and tertiary amines, such as alkyl amines, dialkyl amines, trialkyl amines, substituted alkyl amines, di(substituted alkyl) amines, tri(substituted alkyl) amines, alkenyl amines, dialkenyl amines, trialkenyl amines, substituted alkenyl amines, di(substituted alkenyl) amines, tri(substituted alkenyl) amines, cycloalkyl amines, di(cycloalkyl) amines, tri(cycloalkyl) amines, substituted cycloalkyl amines, disubstituted cycloalkyl amine, trisubstituted cycloalkyl amines, cycloalkenyl amines, di(cycloalkenyl) amines, tri(cycloalkenyl) amines, substituted cycloalkenyl amines, disubstituted cycloalkenyl amine, trisubstituted cycloalkenyl amines, aryl amines, diaryl amines, triaryl amines, heteroaryl amines, diheteroaryl amines, triheteroaryl amines, heterocyclic amines, diheterocyclic amines, triheterocyclic amines, mixed di- and tri-amines where at least two of the substituents on the amine are different and are selected from the group consisting of alkyl, substituted alkyl, alkenyl, substituted alkenyl, cycloalkyl, substituted cycloalkyl, cycloalkenyl, substituted cycloalkenyl, aryl, heteroaryl, heterocyclic, and the like. Also included are amines where the two or three substituents, together with the amino nitrogen, form a heterocyclic or heteroaryl group.

Specific examples of suitable amines include, by way of example only, isopropylamine, trimethyl amine, diethyl amine, tri(iso-propyl) amine, tri(n-propyl) amine, ethanolamine, 2-dimethylaminoethanol, tromethamine, lysine, arginine, histidine, caffeine, procaine, hydrabamine, choline, betaine, ethylenediamine, glucosamine, N-alkylglucamines, theobromine, purines, piperazine, piperidine, morpholine, N-ethylpiperidine, and the like.

Pharmaceutically acceptable acid addition salts may be prepared from inorganic and organic acids. Salts derived from inorganic acids include hydrochloric acid, hydrobromic acid, sulfuric acid, nitric acid, phosphoric acid, and the like. Salts derived from organic acids include acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluene-sulfonic acid, salicylic acid, and the like.

As used herein, "pharmaceutically acceptable carrier" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions is contemplated. Supplementary active ingredients can also be incorporated into the compositions.

"Coronary diseases" or "cardiovascular diseases" refer to diseases of the cardiovasculature arising from any one or more than one of, for example, heart failure (including congestive heart failure, diastolic heart failure and systolic heart failure), acute heart failure, ischemia, recurrent ischemia, myocardial infarction, arrhythmias, angina (including exercise-induced angina, variant angina, stable angina, unstable angina), acute coronary syndrome, diabetes, and intermittent claudication.

"Intermittent claudication" means the pain associated with peripheral artery disease. "Peripheral artery disease" or PAD is a type of occlusive peripheral vascular disease (PVD). PAD affects the arteries outside the heart and brain. The most common symptom of PAD is a painful cramping in the hips, thighs, or calves when walking, climbing stairs, or exercising. The pain is called intermittent claudication. When listing the symptom intermittent claudication, it is intended to include both PAD and PVD.

Arrhythmia refers to any abnormal heart rate. Bradycardia refers to abnormally slow heart rate whereas tachycardia refers to an abnormally rapid heart rate. As used herein, the treatment of arrhythmia is intended to include the treatment of supra ventricular tachycardias such as atrial fibrillation, atrial flutter, AV nodal reentrant tachycardia, atrial tachycardia, and the ventricular tachycardias (VTs), including idiopathic ventricular tachycardia, ventricular fibrillation, pre-excitation syndrome, and Torsade de Pointes (TdP).

Where a given group (moiety) is described herein as being attached to a second group and the site of attachment is not explicit, the given group may be attached at any available site of the given group to any available site of the second group. For example, a "lower alkyl-substituted phenyl", where the attachment sites are not explicit, may have any available site of the lower alkyl group attached to any available site of the phenyl group. In this regard, an "available site" is a site of the group at which a hydrogen of the group may be replaced with a substituent.

"Pharmaceutically-acceptable" means suitable for use in pharmaceutical preparations, generally considered as safe for such use, officially approved by a regulatory agency of a national or state government for such use, or being listed in the U.S. Pharmacopoeia or other generally recognized pharmacopoeia for use in animals, and more particularly in humans.

"Pharmaceutically-acceptable crrier" refers to a diluent, adjuvant, excipient, or carrier, other ingredient, or combination of ingredients that alone or together provide a carrier or vehicle with which a compound or compounds of the invention is formulated and/or administered, and in which every ingredient or the carrier as a whole is pharmaceutically) acceptable.

"Pharmaceutically-acceptable salt" refers to a salt which may enhance desired pharmacological activity. Examples of pharmaceutically-acceptable salts include acid addition salts formed with inorganic or organic acids, metal salts and amine salts. Examples of acid addition salts formed with inorganic acids include salts with hydrochloric acid, hydrobromic acid, sulfuric acid, nitric acid and phosphoric acid. Examples of acid addition salts formed with organic acids such as acetic acid, propionic acid, hexanoic acid, heptanoic acid, cyclopentanepropionic acid, glycolic acid, pyruvic acid, lactic acid, malonic acid, succinic acid, malic acid, maleic acid, fumaric acid, tartaric acid, citric acid, benzoic acid, o-(4-hydroxybenzoyl)-benzoic acid, cinnamic acid, mandelic acid, methanesulfonic acid, ethanesulfonic acid, 1,2-ethanedisulfonic acid, 2-hydroxyethane-sulfonic acid, benzenesulfonic acid, p-chlorobenzenesulfonic acid, 2-naphthalenesulfonic acid, p-toluenesulfonic acid, camphorsulfonic acid, 4-methyl-bicyclo[2.2.2]oct-2-enel-carboxylic acid, gluco-heptonic acid, 4,4'-methylenebis(3-hydroxy-2-naphthoic) acid, 3-phenylpropionic acid, trimethylacetic acid, tertiary butylacetic acid, lauryl sulfuric acid, gluconic acid, glutamic acid, hydroxy-naphthoic acids, salicylic acid, stearic acid and muconic acid. Examples of metal salts include salts with sodium, potassium, calcium, magnesium, aluminum, iron, and zinc ions. Examples of amine salts include salts with ammonia and organic nitrogenous bases strong enough to form salts with carboxylic acids.

"Prodrug" is a compound that, upon in vivo administration, is metabolized by one or more steps or processes or otherwise converted to the biologically, pharmaceutically or therapeutically active form of the compound. To produce a prodrug, the pharmaceutically active compound is modified such that the active compound will be regenerated by metabolic processes. The prodrug may be designed to alter the metabolic stability or the transport characteristics of a drug, to mask side effects or toxicity, to improve the flavor of a drug or to alter other characteristics or properties of a drug. By virtue of knowledge of pharmacodynamic processes and drug metabolism in vivo, those of skill in this art, once a pharmaceutically active compound is known, can design prodrugs of the compound (see, e.g., Nogrady (1985) Medicinal Chemistry A Biochemical Approach, Oxford University Press, New York, pages 388-392).

"Polymorph" refers to the different crystal forms of a compound, resulting from the possibility of at least two different arrangements of the molecules of the compound in the solid state. Polymorphs of a given compound will be different in crystal structure but identical in liquid or vapor states. Different polymorphic forms of a given substance may differ from each other with respect to one or more physical properties, such as solubility and dissociation, true density, crystal shape, compaction behavior, flow properties, and/or solid state stability.

Nomenclature

Names of compounds of the present invention are provided using ChemBioDraw Ultra 11. Other compounds or radicals may be named with common names, or systematic or non-systematic names. The naming and numbering of the compounds of the invention is illustrated with a representative compound of Formula (I)

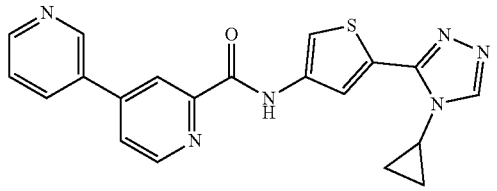

which is named:

N-(5-(4-cyclopropyl-4H-1,2,4-triazol-3-yl)thiophen-3-yl)-3,4'-bipyridine-2'-carboxamide.

Combination Therapy

Coronary patients being treated for an acute cardiovascular disease event by administration of ASK1 inhibitors often exhibit diseases or conditions that benefit from treatment with other therapeutic agents. These diseases or conditions can be of the cardiovascular nature or can be related to pulmonary disorders, metabolic disorders, gastrointestinal disorders and the like. Additionally, some coronary patients being treated for an acute cardiovascular disease event by administration of an ASK1 inhibitor exhibit conditions that can benefit from treatment with therapeutic agents that are antibiotics, analgesics, and/or antidepressants and anti-anxiety agents.

Cardiovascular related diseases or conditions that can benefit from a combination treatment of ASK1 inhibitors with other therapeutic agents include, without limitation, angina, including stable angina, unstable angina (UA), exercised-induced angina, variant angina, arrhythmias, intermittent claudication, myocardial infarction including non-STE myocardial infarction (NSTEMI), heart failure including congestive (or chronic) heart failure, acute heart failure, or recurrent ischemia.

Therapeutic agents suitable for treating cardiovascular related diseases or conditions include anti-anginals, heart failure agents, antithrombotic agents, antiarrhythmic agents, antihypertensive agents, and lipid lowering agents.

The co-administration of ASK1 inhibitors with therapeutic agents suitable for treating cardiovascular related conditions allows enhancement in the standard of care therapy the patient is currently receiving.

Anti-anginals include beta-blockers, calcium channel blockers, and nitrates. Beta blockers reduce the heart's need for oxygen by reducing its workload resulting in a decreased heart rate and less vigorous heart contraction. Examples of beta-blockers include acebutolol (Sectral), atenolol (Tenormin), betaxolol (Kerlone), bisoprolol/hydrochlorothiazide (Ziac), bisoprolol (Zebeta), carteolol (Cartrol), esmolol (Brevibloc), labetalol (Normodyne, Trandate), metoprolol (Lopressor, Toprol XL), nadolol (Corgard), propranolol (Inderal), sotalol (Betapace), and timolol (Blocadren).

Nitrates dilate the arteries and veins thereby increasing coronary blood flow and decreasing blood pressure. Examples of nitrates include nitroglycerin, nitrate patches, isosorbide dinitrate, and isosorbide-5-mononitrate.

Calcium channel blockers prevent the normal flow of calcium into the cells of the heart and blood vessels causing the blood vessels to relax thereby increasing the supply of blood and oxygen to the heart. Examples of calcium channel blockers include amlodipine (Norvasc, Lotrel), bepridil (Vascor), diltiazem (Cardizem, Tiazac), felodipine (Plendil), nifedipine (Adalat, Procardia), nimodipine (Nimotop), nisoldipine (Sular), verapamil (Calan, Isoptin, Verelan), and nicardipine.

Agents used to treat heart failure include diuretics, ACE inhibitors, vasodilators, and cardiac glycosides. Diuretics eliminate excess fluids in the tissues and circulation thereby relieving many of the symptoms of heart failure. Examples of diuretics include hydrochlorothiazide, metolazone (Zaroxolyn), furosemide (Lasix), bumetanide (Bumex), spironolactone (Aldactone), and eplerenone (Inspra).

Angiotensin converting enzyme (ACE) inhibitors reduce the workload on the heart by expanding the blood vessels and decreasing resistance to blood flow. Examples of ACE inhibitors include benazepril (Lotensin), captopril (Capoten), enalapril (Vasotec), fosinopril (Monopril), lisinopril (Prinivil, Zestril), moexipril (Univasc), perindopril (Aceon), quinapril (Accupril), ramipril (Altace), and trandolapril (Mavik).

Vasodilators reduce pressure on the blood vessels by making them relax and expand. Examples of vasodilators include hydralazine, diazoxide, prazosin, clonidine, and methyldopa. ACE inhibitors, nitrates, potassium channel activators, and calcium channel blockers also act as vasodilators.

Cardiac glycosides are compounds that increase the force of the heart's contractions. These compounds strengthen the pumping capacity of the heart and improve irregular heartbeat activity. Examples of cardiac glycosides include digitalis, digoxin, and digitoxin.

Antithrombotics inhibit the clotting ability of the blood. There are three main types of antithrombotics—platelet inhibitors, anticoagulants, and thrombolytic agents.

Platelet inhibitors inhibit the clotting activity of platelets, thereby reducing clotting in the arteries. Examples of platelet inhibitors include acetylsalicylic acid (aspirin), ticlopidine, clopidogrel (plavix), dipyridamole, cilostazol, persantine sulfinpyrazone, dipyridamole, indomethacin, and glycoprotein 11b/111a inhibitors, such as abciximab, tirofiban, and eptifibatide (Integrelin). Beta blockers and calcium channel blockers also have a platelet-inhibiting effect.

Anticoagulants prevent blood clots from growing larger and prevent the formation of new clots. Examples of anticoagulants include bivalirudin (Angiomax), warfarin (Coumadin), unfractionated heparin, low molecular weight heparin, danaparoid, lepirudin, and argatroban.

Thrombolytic agents act to break down an existing blood clot. Examples of thrombolytic agents include streptokinase, urokinase, and tenecteplase (TNK), and tissue plasminogen activator (t-PA).

Antiarrhythmic agents are used to treat disorders of the heart rate and rhythm. Examples of antiarrhythmic agents include amiodarone, quinidine, procainamide, lidocaine, and propafenone. Cardiac glycosides and beta blockers are also used as antiarrhythmic agents.

Antihypertensive agents are used to treat hypertension, a condition in which the blood pressure is consistently higher than normal. Hypertension is associated with many aspects of cardiovascular disease, including congestive heart failure, atherosclerosis, and clot formation.

Examples of antihypertensive agents include alpha-1-adrenergic antagonists, such as prazosin (Minipress), doxazosin mesylate (Cardura), prazosin hydrochloride (Minipress), prazosin, polythiazide (Minizide), and terazosin hydrochloride (Hytrin); beta-adrenergic antagonists, such as propranolol (Inderal), nadolol (Corgard), timolol (Blocadren), metoprolol (Lopressor), and pindolol (Visken); central alpha-adrenoceptor agonists, such as clonidine hydrochloride (Catapres), clonidine hydrochloride and chlorthalidone (Clorpres, Combipres), guanabenz Acetate (Wytensin), guanfacine hydrochloride (Tenex), methyldopa (Aldomet), methyldopa and chlorothiazide (Aldoclor), methyldopa and hydrochlorothiazide (Aldoril); combined alpha/beta-adrenergic antagonists, such as labetalol (Normodyne, Trandate), Carvedilol (Coreg); adrenergic neuron blocking agents, such as guanethidine (Ismelin), reserpine (Serpasil); central nervous system-acting antihypertensives, such as clonidine (Catapres), methyldopa (Aldomet), guanabenz (Wytensin); anti-angiotensin II agents; ACE inhibitors, such as perindopril (Aceon) captopril (Capoten), enalapril (Vasotec), lisinopril (Prinivil, Zestril); angiotensin-II receptor antagonists, such as Candesartan (Atacand), Eprosartan (Teveten), Irbesartan (Avapro), Losartan (Cozaar), Telmisartan (Micardis), Valsartan (Diovan); calcium channel blockers, such as verapamil (Calan, Isoptin), diltiazem (Cardizem), nifedipine (Adalat, Procardia); diuretics; direct vasodilators, such as nitroprusside (Nipride), diazoxide (Hyperstat IV), hydralazine (Apresoline), minoxidil (Loniten), verapamil; and potassium channel activators, such as aprikalim, bimakalim, cromakalim, emakalim, nicorandil, and pinacidil.

Lipid lowering agents are used to lower the amounts of cholesterol or fatty sugars present in the blood. Examples of lipid lowering agents include bezafibrate (Bezalip), ciprofibrate (Modalim), and statins, such as atorvastatin (Lipitor), fluvastatin (Lescol), lovastatin (Mevacor, Altocor), mevastatin, pitavastatin (Livalo, Pitava) pravastatin (Lipostat), rosuvastatin (Crestor), and simvastatin (Zocor).

Patients in need of the ASK1 inhibitor often suffers from secondary medical conditions such as one or more of a metabolic disorder, a pulmonary disorder, a peripheral vascular disorder, or a gastrointestinal disorder. Such patients can benefit from treatment of a combination therapy comprising administering to the patient the compounds of the invention in combination with at least one therapeutic agent.

Pulmonary disorder refers to any disease or condition related to the lungs. Examples of pulmonary disorders include, without limitation, asthma, chronic obstructive pulmonary disease (COPD), bronchitis, and emphysema.

Examples of therapeutics agents used to treat pulmonary disorders include bronchodilators including beta2 agonists and anticholinergics, corticosteroids, and electrolyte supplements. Specific examples of therapeutic agents used to treat pulmonary disorders include epinephrine, terbutaline (Brethaire, Bricanyl), albuterol (Proventil), salmeterol (Serevent, Serevent Diskus), theophylline, ipratropium bromide (Atrovent), tiotropium (Spiriva), methylprednisolone (Solu-Medrol, Medrol), magnesium, and potassium.

Examples of metabolic disorders include, without limitation, diabetes, including type I and type II diabetes, metabolic syndrome, dyslipidemia, obesity, glucose intolerance, hypertension, elevated serum cholesterol, and elevated triglycerides.

Examples of therapeutic agents used to treat metabolic disorders include antihypertensive agents and lipid lowering agents, as described in the section "Cardiovascular Agent Combination Therapy" above. Additional therapeutic agents used to treat metabolic disorders include insulin, sulfonylureas, biguanides, alpha-glucosidase inhibitors, and incretin mimetics.

Peripheral vascular disorders are disorders related to the blood vessels (arteries and veins) located outside the heart and brain, including, for example peripheral arterial disease (PAD), a condition that develops when the arteries that supply blood to the internal organs, arms, and legs become completely or partially blocked as a result of atherosclerosis.

Gastrointestinal disorders refer to diseases and conditions associated with the gastrointestinal tract. Examples of gastrointestinal disorders include gastroesophageal reflux disease (GERD), inflammatory bowel disease (IBD), gastroenteritis, gastritis and peptic ulcer disease, and pancreatitis.

Examples of therapeutic agents used to treat gastrointestinal disorders include proton pump inhibitors, such as pantoprazole (Protonix), lansoprazole (Prevacid), esomeprazole (Nexium), omeprazole (Prilosec), rabeprazole; H2 blockers, such as cimetidine (Tagamet), ranitidine (Zantac), famotidine (Pepcid), nizatidine (Axid); prostaglandins, such as misoprostoL (Cytotec); sucralfate; and antacids.

Patients presenting with an acute coronary disease event may exhibit conditions that benefit from administration of therapeutic agent or agents that are antibiotics, analgesics, antidepressant and anti-anxiety agents in combination with ranolazine.

Antibiotics are therapeutic agents that kill, or stop the growth of, microorganisms, including both bacteria and fungi. Example of antibiotic agents include β-Lactam antibiotics, including penicillins (amoxicillin), cephalosporins, such as cefazolin, cefuroxime, cefadroxil (Duricef), cephalexin (Keflex), cephradine (Velosef), cefaclor (Ceclor), cefuroxime axtel (Ceftin), cefprozil (Cefzil), loracarbef (Lorabid), cefixime (Suprax), cefpodoxime proxetil (Vantin), ceftibuten (Cedax), cefdinir (Omnicef), ceftriaxone (Rocephin), carbapenems, and monobactams; tetracyclines, such as tetracycline; macrolide antibiotics, such as erythromycin; aminoglycosides, such as gentamicin, tobramycin, amikacin; quinolones such as ciprofloxacin; cyclic peptides, such as vancomycin, streptogramins, polymyxins; lincosamides, such as clindamycin; oxazolidinoes, such as linezolid; and sulfa antibiotics, such as sulfisoxazole.

Analgesics are therapeutic agents that are used to relieve pain. Examples of analgesics include opiates and morphinomimetics, such as fentanyl and morphine; paracetamol; NSAIDs, and COX-2 inhibitors.

Antidepressant and anti-anxiety agents include those agents used to treat anxiety disorders, depression, and those used as sedatives and tranquillers. Examples of antidepressant and anti-anxiety agents include benzodiazepines, such as diazepam, lorazepam, and midazolam; enzodiazepines; barbiturates; glutethimide; chloral hydrate; meprobamate; sertraline (Zoloft, Lustral, Apo-Sertral, Asentra, Gladem, Serlift, Stimuloton); escitalopram (Lexapro, Cipralex); fluoxetine (Prozac, Sarafem, Fluctin, Fontex, Prodep, Fludep, Lovan); venlafaxine (Effexor XR, Efexor); citalopram (Celexa, Cipramil, Talohexane); paroxetine (Paxil, Seroxat, Aropax); trazodone (Desyrel); amitriptyline (Elavil); and bupropion (Wellbutrin, Zyban).

Pharmaceutical Compositions and Administration

Compounds provided in accordance with the present invention are usually administered in the form of pharmaceutical compositions. This invention therefore provides pharmaceutical compositions that contain, as the active ingredient, one or more of the compounds described, or a pharmaceutically acceptable salt or ester thereof, and one or more pharmaceutically acceptable excipients, carriers, including inert solid diluents and fillers, diluents, including sterile aqueous solution and various organic solvents, permeation enhancers, solubilizers and adjuvants. The pharmaceutical compositions may be administered alone or in combination with other therapeutic agents. Such compositions are prepared in a manner well known in the pharmaceutical art (see, e.g., Remington's Pharmaceutical Sciences, Mace Publishing Co., Philadelphia, Pa. 17th Ed. (1985); and Modern Pharmaceutics, Marcel Dekker, Inc. 3rd Ed. (G. S. Banker & C. T. Rhodes, Eds.)

The pharmaceutical compositions may be administered in either single or multiple doses by any of the accepted modes of administration of agents having similar utilities, for example as described in those patents and patent applications incorporated by reference, including rectal, buccal, intranasal and transdermal routes, by intra-arterial injection, intravenously, intraperitoneally, parenterally, intramuscularly, subcutaneously, orally, topically, as an inhalant, or via unimpregnated or coated device such as a stent, for example, or an artery-inserted cylindrical polymer.

One mode for administration is parenteral, particularly by injection. The forms in which the novel compositions of the present invention may be incorporated for administration by injection include aqueous or oil suspensions, or emulsions, with sesame oil, corn oil, cottonseed oil, or peanut oil, as well as elixirs, mannitol, dextrose, or a sterile aqueous solution, and similar pharmaceutical vehicles. Aqueous solutions in saline are also conventionally used for injection, but less preferred in the context of the present invention. Ethanol, glycerol, propylene glycol, liquid polyethylene glycol, and the like (and suitable mixtures thereof), cyclodextrin derivatives, and vegetable oils may also be employed. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like.

Sterile injectable solutions are prepared by incorporating a compound according to the present invention in the required amount in the appropriate solvent with various other ingredients as enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

Oral administration is another route for administration of compounds in accordance with the invention. Administration may be via capsule or enteric coated tablets, or the like. In making the pharmaceutical compositions that include at least one compound described herein, the active ingredient is usually diluted by an excipient and/or enclosed within such a carrier that can be in the form of a capsule, sachet, paper or other container. When the excipient serves as a diluent, it can be in the form of a solid, semi-solid, or liquid material (as above), which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, sterile injectable solutions, and sterile packaged powders.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, sterile water, syrup, and methyl cellulose. The formulations can additionally include: lubricating agents such as talc, magnesium stearate, and mineral oil; wetting agents; emulsifying and suspending agents; preserving agents such as methyl and propylhydroxy-benzoates; sweetening agents; and flavoring agents.

The compositions of the invention can be formulated so as to provide quick, sustained or delayed release of the active ingredient after administration to the patient by employing procedures known in the art. Controlled release drug delivery systems for oral administration include osmotic pump systems and dissolutional systems containing polymer-coated reservoirs or drug-polymer matrix formulations. Examples of controlled release systems are given in U.S. Pat. Nos. 3,845,770; 4,326,525; 4,902,514; and 5,616,345. Another formulation for use in the methods of the present invention employs transdermal delivery devices ("patches"). Such transdermal patches may be used to provide continuous or discontinuous infusion of the compounds of the present invention in controlled amounts. The construction and use of transdermal patches for the delivery of pharmaceutical agents is well known in the art. See, e.g., U.S. Pat. Nos. 5,023,252, 4,992,445 and 5,001,139. Such patches may be constructed for continuous, pulsatile, or on demand delivery of pharmaceutical agents.

The compositions are preferably formulated in a unit dosage form. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient (e.g., a tablet, capsule, ampoule). The compounds are generally administered in a pharmaceutically effective amount. Preferably, for oral administration, each dosage unit contains from 1 mg to 2 g of a compound described herein, and for parenteral administration, preferably from 0.1 to 700 mg of a compound a compound described herein. It will be understood, however, that the amount of the compound actually administered usually will be determined by a physician, in the light of the relevant circumstances, including the condition to be treated, the chosen route of administration, the actual compound administered and its relative activity, the age, weight, and response of the individual patient, the severity of the patient's symptoms, and the like.

For preparing solid compositions such as tablets, the principal active ingredient is mixed with a pharmaceutical excipient to form a solid preformulation composition containing a homogeneous mixture of a compound of the present invention. When referring to these preformulation compositions as homogeneous, it is meant that the active ingredient is dispersed evenly throughout the composition so that the composition may be readily subdivided into equally effective unit dosage forms such as tablets, pills and capsules.

The tablets or pills of the present invention may be coated or otherwise compounded to provide a dosage form affording the advantage of prolonged action, or to protect from the acid conditions of the stomach. For example, the tablet or pill can comprise an inner dosage and an outer dosage component, the latter being in the form of an envelope over the former. The two components can be separated by an enteric layer that serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. Preferably, the compositions are administered by the oral or nasal respiratory route for local or systemic effect. Compositions in preferably pharmaceutically acceptable solvents may be nebulized by use of inert gases. Nebulized solutions may be inhaled directly from the nebulizing device or the nebulizing device may be attached to a facemask tent, or intermittent positive pressure breathing machine. Solution, suspension, or powder compositions may be administered, preferably orally or nasally, from devices that deliver the formulation in an appropriate manner.

Synthesis of Compounds of Formula I

The compounds of the invention may be prepared using methods disclosed herein and routine modifications thereof which will be apparent given the disclosure herein and methods well known in the art. Conventional and well-known synthetic methods may be used in addition to the teachings herein. The synthesis of typical compounds described herein, e.g. compounds having structures described by one or more of Formula (I), may be accomplished as described in the following examples. If available, reagents may be purchased commercially, e.g. from Sigma Aldrich or other chemical suppliers.

General Syntheses:

Typical embodiments of compounds in accordance with the present invention may be synthesized using the general reaction schemes described below. It will be apparent given the description herein that the general schemes may be altered by substitution of the starting materials with other materials having similar structures to result in products that are correspondingly different. Descriptions of syntheses follow to provide numerous examples of how the starting materials may vary to provide corresponding products. Given a desired product for which the substituent groups are defined, the necessary starting materials generally may be determined by inspection. Starting materials are typically obtained from commercial sources or synthesized using published methods. For synthesizing compounds which are embodiments of the present invention, inspection of the structure of the compound to be synthesized will provide the identity of each substituent group. The identity of the final product will generally render apparent the identity of the necessary starting materials by a simple process of inspection, given the examples herein.

Synthetic Reaction Parameters

The terms "solvent," "inert organic solvent" or "inert solvent" refer to a solvent inert under the conditions of the reaction being described in conjunction therewith (including, for example, benzene, toluene, acetonitrile, tetrahydrofuran ("THF"), dimethylformamide ("DMF"), chloroform, methylene chloride (or dichloromethane), diethyl ether, methanol, pyridine and the like). Unless specified to the contrary, the solvents used in the reactions of the present invention are inert organic solvents, and the reactions are carried out under an inert gas, preferably nitrogen.

One method of preparing compounds of Formula (I) is shown in Reaction Scheme I.

REACTION SCHEME I

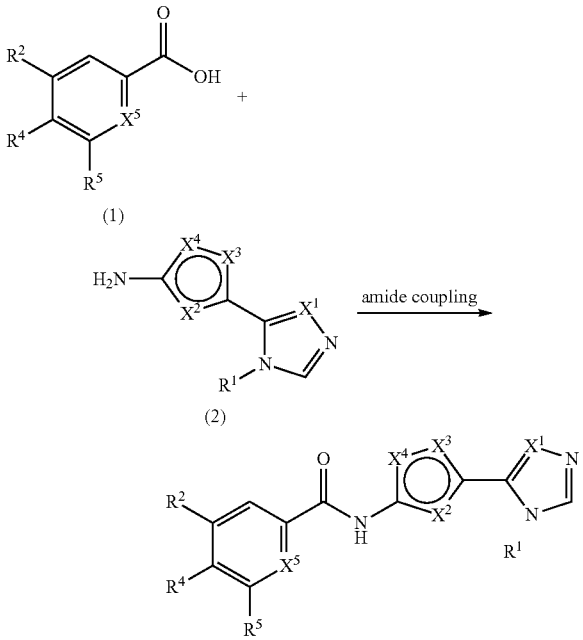

A carboxylic acid of formula (1) is reacted with an amine of formula (2) under conditions suitable for the formation of an amide (see, for example, Tetrahedron 60 (2004) 2447-2467). For example, to a mixture of the compound of formula (1) and formula (2) in an inert solvent, for example N,N-dimethylformamide, is added (2-(7-Aza-1H-benzotriazole-1-yl)-1,1,3,3-tetramethyluronium hexafluorophosphate (HATU) and a base, typically N-methyl morpholine, and the mixture is maintained at about room temperature for about 1-12 hours. When the reaction is substantially complete, the product of Formula (I) is isolated by conventional means, for example by filtration.

Alternatively, the reaction may be carried out by reacting a mixture of (1) and N-methylimidazole and a base, for example N-methylmorpholine, with (2) in an inert solvent, for example N,N-dimethylformamide.

Alternatively, the carboxylic acid of formula (1) is first converted to an acid halide, for example an acid chloride, with, for example, thionyl chloride or oxalyl chloride, and reacted with the amine of formula (2) in an inert solvent, for example dichloromethane, in the presence of a base, for example dimethylaminopyridine. In general, the carboxylic acid of formula (1) is converted to an acid chloride in an inert solvent, for example dichlorethane, in the presence of N,N-dimethylformamide, After removal of the solvent under reduced pressure the residue is dissolved in an inert solvent, for example dichloromethane, and reacted with the amine of formula (2) in the presence of a base, for example dimethylaminopyridine. When the reaction is substantially complete, the product of Formula (I) is isolated by conventional means.

Preparation of a Compound of Formula (2)

The amine of formula (2) is either commercially available or is prepared by means well know in the art. One example of the preparation of a compound of a compound of formula (2) in which $X^1$ is nitrogen is shown in Reaction Scheme IA.

REACTION SCHEME IA

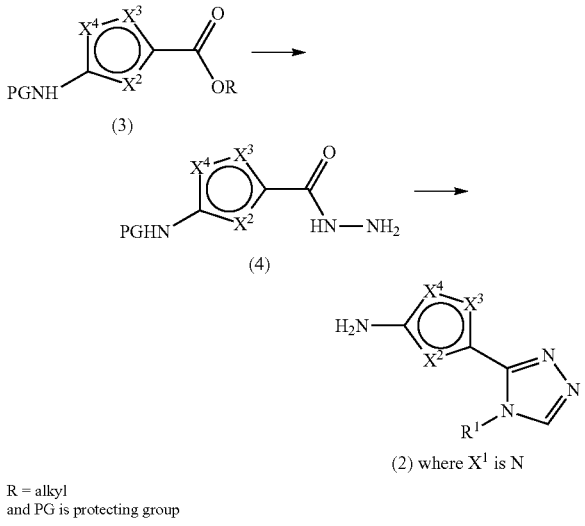

Step 1—Preparation of a Compound of Formula (4)

In general, a protected amino ester of formula (3) is reacted with hydrazine hydrate in a protic solvent, for example ethanol. The reaction is carried out at a temperature of about 50-90° C., for about 1-5 hours. When the reaction is substantially complete, the product of formula (4) is isolated by conventional means.

Step 2—Preparation of a Compound of Formula (2)

The compound of formula (4) is then placed in a sealable flask with an amine of formula $R^1NH_2$ together with a formamide of formula $R^1NHCHO$ in an inert solvent, for example toluene, in the presence of an acid, for example trifluoroacetic acid. The sealed flask is heated at about 100° C. for about 24 hours. When the reaction is substantially complete, the product of formula (2) is isolated by conventional means, for example by flash chromatography.

The product is then reduced under an atmosphere of hydrogen with a palladium catalyst to remove the protecting group. The reaction is carried out in a protic solvent, for example ethanol, for about 1-2 hours. When the reaction is substantially complete, the product of formula (2) is isolated by conventional means.

Another example of the preparation of a compound of formula (2) in which $X^1$ is nitrogen is shown in Reaction Scheme IB.

REACTION SCHEME IB

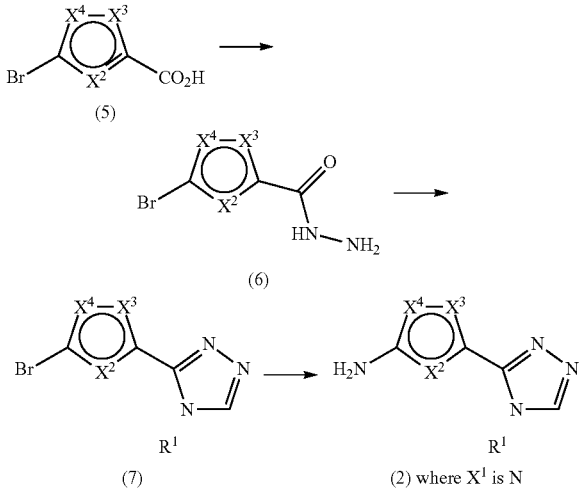

Step 1—Preparation of a Compound of Formula (6)

A mixture of bromocarboxylic acid of formula (5) and thionyl chloride in a protic solvent, for example methanol or ethanol, is refluxed for about 1-6 hours. The concentrated reaction residue is then suspended in ethanol and hydrazine hydrate and refluxed for about 1-3 hours. When the reaction is substantially complete, the product of formula (6) is isolated by conventional means.

Step 2—Preparation of a Compound of Formula (7)

To the acyl hydrazide compound of formula (6) in an inert solvent, for example toluene is added N,N-dimethylformamide/N,N-dimethylacetamide complex and the mixture is stirred for 1-10 minutes. To this reaction mixture is added an amine of formula R1NH2 in presence of an acid, for example acetic acid, and the solution is heated in a microwave reactor for about 10-90 minutes at about 60-160° C. When the reaction is substantially complete, the product of formula (7) is isolated by conventional means and used in the next step.

Step 3—Preparation of a Compound of Formula (2)

To a mixture of the compound of formula (7) and a copper catalyst, for example $Cu(acac)_2$, and cesium carbonate in an inert solvent, for example, N,N-dimethylformamide, is added pentadione and a base, for example, ammonium hydroxide. This mixture is placed in a microwave vial and heated at about 60-100° C. for about 1-8 hours. When the reaction is substantially complete, the product of formula (2) is isolated by conventional methods.

Another example of the preparation of a compound of formula (2) in which $X^1$ is nitrogen is shown in Reaction Scheme ID.

REACTION SCHEME ID

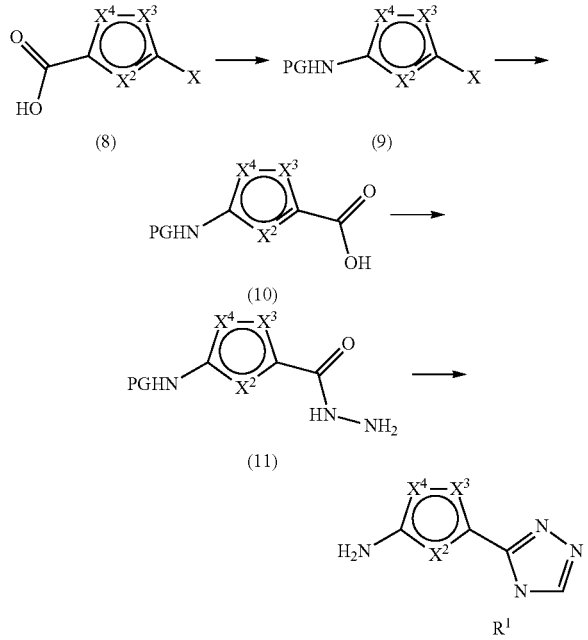

X = Cl, Br

Step 1—Preparation of a Compound of Formula (9)

The carboxylic acid of formula (8) is treated with diphenylphosphorylazide (the Curtius Reaction) in a mixture of solvents, for example N,N-dimethylformamide and an alcohol, and the resulting protected amine of formula (9), in which PG is a protecting group related to the alcohol employed, is isolated by conventional means.

Step 2—Preparation of a Compound of Formula (10)

The protected amine of formula (9) is treated with a base, for example n-butyl lithium or lithium diisopropylamide, in an inert solvent, for example tetrahydrofuran, followed by carbon dioxide. When the reaction is complete, the carboxylic acid of formula (10) is isolated by conventional methods.

Step 3—Preparation of a Compound of Formula (11)

A mixture of carboxylic acid (10) and thionyl chloride in a protic solvent, for example methanol, is refluxed for about 1-6 hours. The concentrated reaction residue is then suspended in ethanol and hydrazine hydrate is added, and the mixture is refluxed for about 1-3 hours. When the reaction is substantially complete, the product of formula (11) is isolated by conventional means.

Step 3—Preparation of a Compound of Formula (2)

To the acyl hydrazide compound of formula (11) in an inert solvent, for example toluene, is added N,N-dimethylformamide/N,N-dimethylacetamide complex and stirred for 1-10 minutes. To this reaction mixture is added an amine of formula $R^1NH_2$ in presence of an acid, for example acetic acid and heated in a microwave reactor for about 10-90 minutes at about 150° C. When the reaction is substantially complete, the product of formula (2) is isolated by conventional means of purification.

One example of the preparation of a compound of formula (2) in which $X^1$ is carbon is shown in Reaction Scheme IE.

REACTION SCHEME IE

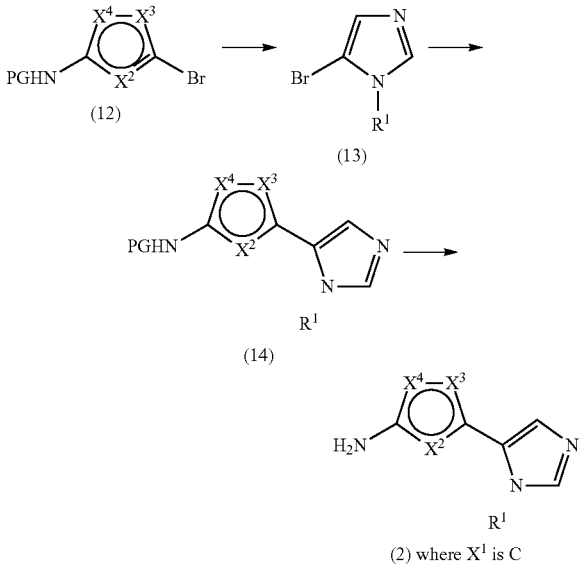

PG is protecting group

Step 1—Preparation of a Compound of Formula (2)

To a solution of the imidazole derivative compound of formula (13) in an inert solvent, for example tetrahydrofuran, at about −50° C. to −80° C., is added a base, for example n-butyl lithium. The reaction is maintained at this temperature for about 10-60 minutes, then a solution of zinc bromide in an inert solvent, for example tetrahydrofuran, is added, and the mixture allowed to warm to about room temperature for about 2-3 hours. A solution of the compound of formula (12) in an inert solvent, for example tetrahydrofuran, is added in the presence of a palladium complex catalyst, for example $Pd(PPh_3)_4$, and the mixture stirred for about 10-24 hours. When the reaction is substantially complete, the product of formula (1) is isolated and deprotected and purified by conventional means, to provide the compound of formula (2) when $X^1$ is carbon.

An alternative preparation of a compound of Formula (I) is shown in Reaction Scheme II.

REACTION SCHEME II

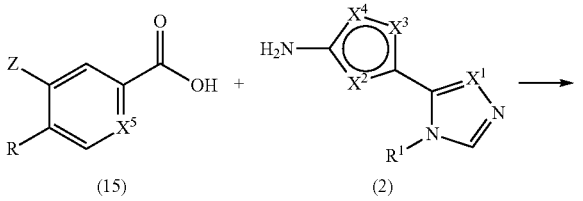

-continued

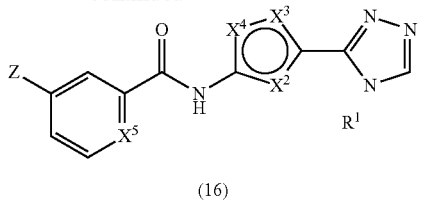

Z = Cl, Br or I

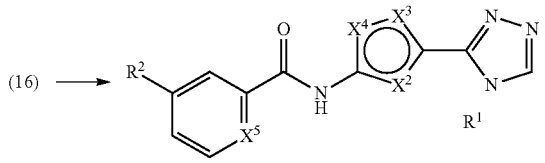

Formula (I) where $X^1$ is N

Step 1—Preparation of a Compound of Formula (16)

A carboxylic acid of formula (15) in which Z is a halogen, for example chloro, bromo, or iodo, is reacted with an amine of formula (2) in the same manner as described in Reaction Scheme I to provide a compound of formula (16).

Step 2—Preparation of a Compound of Formula (I) in which $X^1$ is N

The compound of formula (16) is then reacted with a boronic acid derivative of $R^2$, for example 3-pyridine boronic acid, in the presence of a phosphine ligand of a palladium halide derivative, for example $dppf(Pd)Cl_2$ (diphenylphosphineferrocene palladium chloride) and a mild base, for example potassium carbonate. The reaction is typically conducted in a mixture of inert solvents, for example a mixture of toluene, water, and ethanol, for about 60-100° C. for about 1-4 hours. When the reaction is substantially complete, the product of Formula (I) is isolated by conventional means, for example by reverse-phase HPLC.

A compound of Formula (I) in which $R^2$ is a non-aromatic ring can be prepared by displacement of Z with a nucleophile, for example an amine, particularly a cyclic amine, or with an alcohol or thiol derivative. Typically, if the nucleophile is an amine, the reaction is carried out using the amine as a solvent if possible, or the reaction is carried out in a polar aprotic solvent, such as N,N-dimethylformamide, dimethylsulfoxide, or N-methylpyrrolidine, for example. The reaction mixture is maintained at about 80-119° C. for about 1-10 hours. When the reaction is substantially complete, the product of Formula (I) is isolated by conventional means, for example by reverse-phase HPLC.

The construction of compounds of Formula (I) in which $X^1$ is $C(R^3)$ can be accomplished as shown above for the compound of Formula (I) in which $X^1$ is N.

An alternative preparation of a hydrazide precursor to compounds of Formula (I) is shown in Reaction Scheme III.

REACTION SCHEME III
Alternative Preparation of a Hydrazide precursor to Compounds of Formula (I)

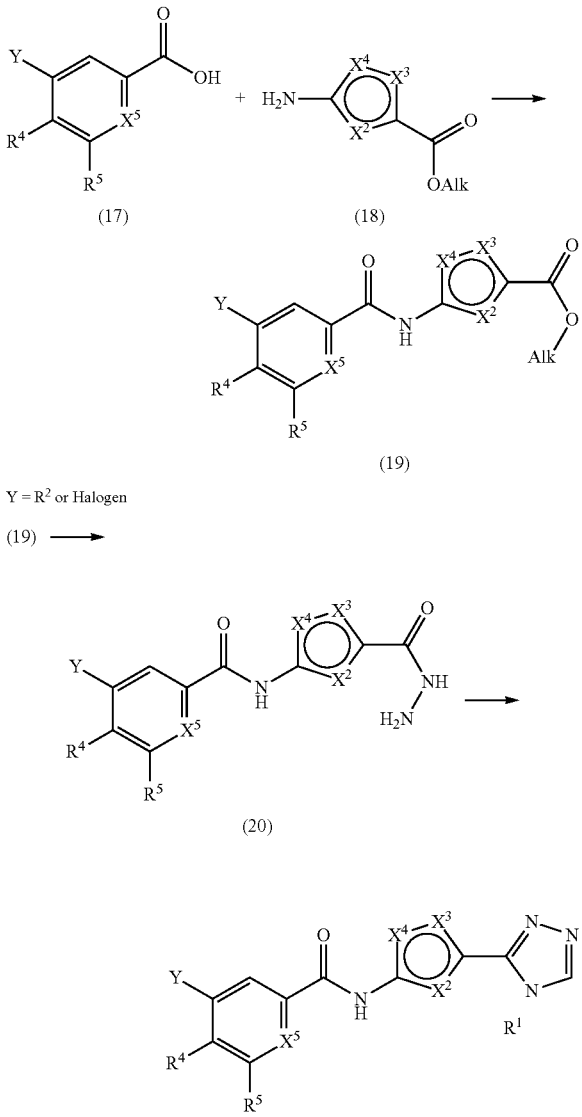

Step 1—Preparation of a Compound of Formula (19)

A carboxylic acid of formula (17) where Y is $R^2$ or halogen is reacted with an amine of formula (18) under conditions suitable for the formation of an amide. For example, to a mixture of the compound of formula (17) and formula (18) in an inert solvent, for example N,N-dimethylformamide, is added (2-(7-Aza-1H-benzotriazole-1-yl)-1,1,3,3-tetramethyluronium hexafluorophosphate (HATU) and a base, typically N-methyl morpholine, and the mixture is maintained at about room temperature for about 1-24 hours. When the reaction is substantially complete, the compound of formula (19) is isolated by conventional means.

Step 2—Preparation of a Compound of Formula (20)

The ester of formula (19) is reacted with hydrazine hydrate as described in Reaction Scheme IA to provide a hydrazide of formula (20).

Step 3—Preparation of a Compound of Formula (16)

To the acyl hydrazide compound of formula (20) in an inert solvent, for example toluene, is added N,N-dimethylformamide/N,N-dimethylacetamide complex, and the mixture stirred for 1-10 minutes. To this reaction mixture is added an amine of formula $R^1NH_2$ in presence of an acid, for example acetic acid and heated in a microwave reactor for about 10-90 minutes at about 100-160° C. When the reaction is substantially complete, the product of formula (16) is isolated by conventional means of purification.

The compound of formula (16) can be converted to a compound of formula (I) as shown in Reaction Scheme II.

The compounds of formula (1) and (2) are either commercially available or are prepared by means well known in the art. One example of the preparation of a compound of formula (1) from (3) is shown in Reaction Scheme IV.

REACTION SCHEME IV
Alternative Preparation of a Compound of Formula (1)

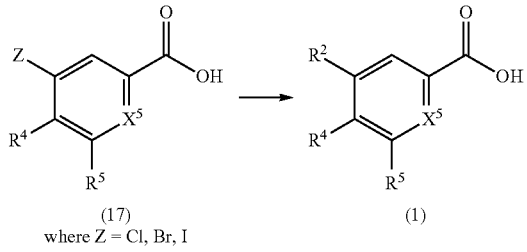

Step 1

To a suspension of a carboxylic acid of formula (17) in oxalyl chloride is added N,N-dimethylformamide. The mixture is maintained at about room temperature for about 1 hour, then the reaction quenched by addition of an alcohol, for example isopropanol. The ester thus produced is isolated conventionally, for example by chromatography.

Step 2

To this ester in an inert aqueous solvent mixture, for example toluene/water/isopropanol, is added a 4,4,5,5-tetramethyl-2-aryl-1,3,2-dioxaborolane derivative and a base, for example potassium carbonate, and dppf(Pd)$Cl_2$. The mixture is maintained at about 40-80° C. for about 30 minutes to 4 hours. When the reaction is substantially complete, the product is isolated by conventional means. This ester is converted to a carboxylic acid by conventional means, for example by heating in aqueous hydrochloric acid, to provide a compound of formula (1)

Alternatively, the halide of the compound of formula (17) as an alkyl ester can first be converted to a boronic acid derivative, for example by treatment with 4,4,4',4',5,5,5',5'-octamethyl-2,2'-bi(1,3,2-dioxaborolane) in the presence of dppf(Pd)$Cl_2$, then reacting the boronic acid derivative thus obtained with an aryl bromide in the presence of dppf(Pd)$Cl_2$ in an inert aqueous solvent mixture, for example toluene/water/isopropanol and a mild base, for example potassium acetate (the Suzuki Reaction).

Utility, Testing and Administration

General Utility

The compounds of Formula I are generally effective in the treatment of conditions that respond to administration of ASK1 inhibitors. Specifically, the compounds of Formula I are useful in the treatment of a broad range of diseases, for example autoimmune disorders, inflammatory diseases, cardiovascular diseases (including diabetes, diabetic nephropathy, and other complications of diabetes), cardio-renal diseases, including kidney disease, fibrotic diseases, respiratory diseases (including COPD, idiopathic pulmonary fibrosis (IPF), and acute lung injury), acute and chronic liver diseases, and neurodegenerative diseases.

Testing

Activity testing is conducted as described in those patents and patent applications referenced above, and in the Examples below, and by methods apparent to one skilled in the art.

The following examples are included to demonstrate preferred embodiments of the invention. It will be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLE 1

Preparation of a Compound of Formula (4)

A. Preparation of a Compound of Formula (4) in which $R^1$ is Cyclopropyl, $X^2$ and $X^4$ are CH, $X^3$ is S, $X^5$ is N, and Z is Bromo

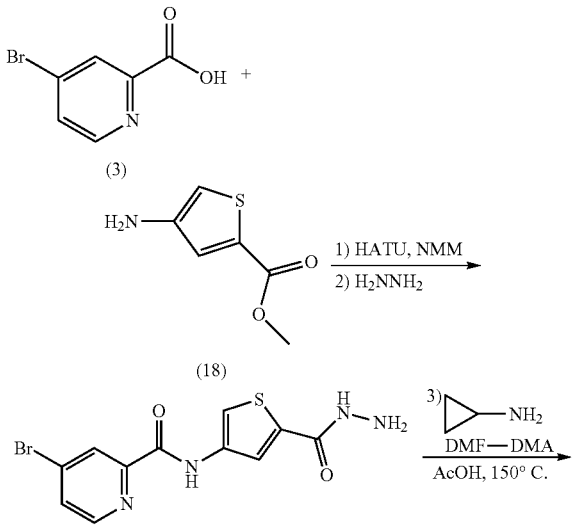

-continued

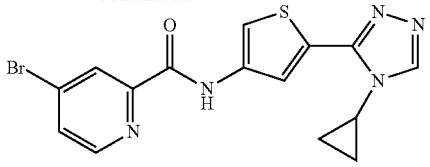

Step 1—Preparation of a Compound of Formula (20) in which $X^2$ and $X^4$ are CH, $X^3$ is S, $X^5$ is N, and Z is Bromo A solution of 4-bromo-pyridine-2-carboxylic acid (1.98 g, 9.80 mmol), methyl 4-aminothiophene-2-carboxylate (1.40 g, 8.91 mmol), 2-(1H-7-Azabenzotriazol-1-yl)-1,1,3,3-tetramethyl uronium hexafluorophosphate methanaminium (HATU) (4.07 g, 10.7 mmol), and N-methylmorpholine (1.18 mL, 10.7 mmol) in N,N-dimethylformamide (18 mL) was stirred at room temperature for 6 hours. The solvent was removed under reduced pressure, the residue suspended in acetonitrile, and the solids were isolated by filtration. The solids were washed with water (80 mL), acetonitrile (80 mL) and diethyl ether (80 mL), and dried under reduced pressure to afford methyl 4-(4-bromopicolinamido)thiophene-2-carboxylate, a compound of formula (19) as a white powder (2.70 g, 90% yield). M+1=341.1.

The methyl 4-(4-bromopicolinamido)thiophene-2-carboxylate (2.7 g, 6.9 mmol) was dissolved in ethanol, hydrazine hydrate (1.4 mL, 28 mmol) was added and the reaction was refluxed overnight. The reaction mixture was concentrated, and the solids were suspended in acetonitrile and filtered to afford 2.4 g (70%) 4-bromo-N-(5-(hydrazinecarbonyl)thiophen-3-yl)picolinamide as a white solid. M+1=341.1

Step 2—Preparation of a Compound of Formula (4) in which $R^1$ is Cyclopropyl, $X^2$ and $X^4$ are CH, $X^3$ is S, $X^5$ is N, and Z is Bromo The 4-bromo-N-(5-(hydrazinecarbonyl)thiophen-3-yl)picolinamide (600 mg, 1.8 mmol) and toluene (9 mL) were added to a sealable vial, N,N-dimethylformamide•N,N-dimethylacetamide (600 μL, 4.5 mmol) was added and the reaction was stirred for 5 minutes. Cyclopropyl amine (490 μL, 7.2 mmol), and acetic acid (100 μL, 1.8 mmol) were added and the reaction was heated in a microwave reactor at 145° C. for 30 minutes. The solvent was removed under reduced pressure, and the product, 4-bromo-N-(5-(4-cyclopropyl-4H-1,2,4-triazol-3-yl)thiophen-3-yl)picolinamide 350 mg (50%), was isolated by precipitation from acetonitrile/methanol. Alternatively, the reaction mixture may be purified by flash chromatography. M+1=390.1

B. Preparation of a Compound of Formula (4) in which $R^1$ is Cyclopropyl, $X^2$ is N, $X^3$ is CH, $X^4$ is S, $X^5$ is N, and Z is Bromo or Iodo Similarly, following the procedure of Example 1A, but replacing methyl 4-aminothiophene-2-carboxylate with methyl 2-aminothiazole-4-carboxylate, and replacing 4-bromo-N-(4-(4-cyclopropyl-4H-1,2,4-triazol-3-yl)thiazol-2-yl)picolinamide was made.

Similarly, following the procedure of Example 1A, but replacing 4-bromo-pyridine-2-carboxylic acid with 4-bromo-5-methylpicolinic acid, and replacing methyl 4-aminothiophene-2-carboxylate by 2-(4-cyclopropyl-4H-1,2,4-triazol-3-yl)thiazol-4-amine, 4-bromo-N-(2-(4-cyclopropyl-4H-1,2,4-triazol-3-yl)thiazol-4-yl)-5-methylpicolinamide was made. M+1=406.1

Similarly, following the procedure of Example 1A, but replacing 4-bromo-pyridine-2-carboxylic acid with 4-iodopyridine-2-carboxylic acid, and replacing methyl 4-aminothiophene-2-carboxylate with 2-(4-cyclopropyl-4H-1,2,4-triazol-3-yl)thiazol-4-amine, N-(2-(4-cyclopropyl-4H-1,2,4-triazol-3-yl)thiazol-4-yl)-3-iodobenzamide was prepared. M+1=437.1

Similarly, optionally replacing 4-bromo-pyridine-2-carboxylic acid with the appropriate acid of formula (1), and optionally replacing methyl 4-aminothiophene-2-carboxylate with the appropriate amino ester of formula (m), the following compounds of formula (4) were prepared:

(S)-4-bromo-5-methyl-N-(2-(4-(1,1,1-trifluoropropan-2-yl)-4H-1,2,4-triazol-3-yl)thiazol-4-yl)picolinamide. M+1=462.2;

5-bromo-N-(5-(4-cyclopropyl-4H-1,2,4-triazol-3-yl)thiophen-3-yl)-2-methoxybenzamide. M+1=420.2;

5-bromo-N-(5-(4-cyclopropyl-4H-1,2,4-triazol-3-yl)thiophen-3-yl)-2,4-dimethoxybenzamide; M+1=450.1

4-bromo-N-(5-(4-cyclopropyl-4H-1,2,4-triazol-3-yl)thiophen-3-yl)-5-methylpicolinamide; M+1=405.1

C. Preparation of other Compounds of Formula (4)

Similarly, following the procedure of Example 1A, but replacing methyl 4-aminothiophene-2-carboxylate with other compounds of formula (m), and replacing 4-bromopyridine-2-carboxylic acid with other compounds of formula (3), other compounds of formula (4) are prepared.

EXAMPLE 2

Preparation of a Compound of Formula (5)

Preparation of a Compound of Formula (5) in which $X^2$ is CH, $X^3$ is S, $X^4$ is CH, $X^5$ is N, and Y is 4-(4-cyclopropyl-1H-imidazol-1-yl)

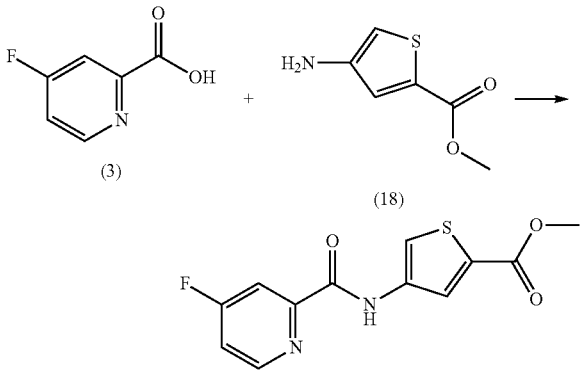

-continued

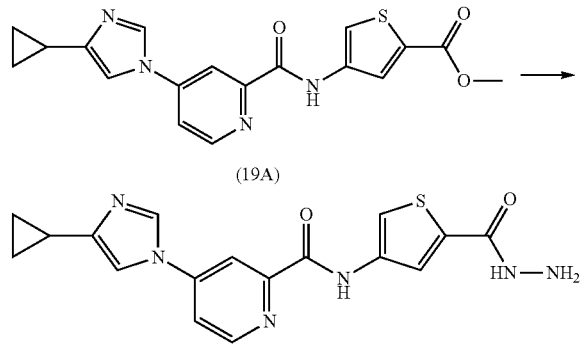

Step 1—Preparation of a Compound of Formula (19) in which R is Hydrogen, Y is Fluoro, $X^2$ is CH, $X^3$ is S, $X^4$ is CH, $X^5$ is N, and OAlk is Methoxy A solution of 4-fluoropicolinic acid (1.0 g, 6.4 mmol), HATU (2.9 g, 7.6 mmol), and N-methylmorpholine (0.84 mL, 7.6 mmol) in N,N-dimethylformamide (12 mL) was stirred at 0° C. for 30 minutes. Methyl 4-aminothiophene-2-carboxylate (990 mg, 7.0 mmol) was added, the reaction was stirred for 30 minutes at 0° C., then warmed to room temperature, and stirred for an additional 2 hours. The solvent was removed under reduced pressure, the residue was suspended in acetonitrile/$H_2O$ (1:1) and the solids were isolated by filtration, washed with water, acetonitrile, then dried to afford methyl 4-(4-fluoropicolinamido)thiophene-2-carboxylate as a white powder (1.0 g, 56% yield). M+1=281.1.

Step 2—Preparation of a Compound of Formula (19A) in which R is Hydrogen, $X^2$ is CH, $X^3$ is S, $X^4$ is CH, $X^5$ is N, and Y is 4-(4-cyclopropyl-1H-imidazol-1-yl)

To a solution of methyl 4-(4-fluoropicolinamido)thiophene-2-carboxylate (400 mg, 1.4 mmol) in butyronitrile (5 mL), was added 4-cyclopropyl imidazole (310 mg, 2.9 mmol), and caesium carbonate (840 mg, 2.6 mmol) and the reaction was heated to 105° C. for 2 hours. The reaction was filtered and the solids were washed with acetonitrile, methylene chloride, and the filtrate was evaporated under reduced pressure. The residue was suspended in acetonitrile, and the solids were collected by filtration to provide 384 mg (73%) of methyl 4-(4-(4-cyclopropyl-1H-imidazol-1-yl)picolinamido)thiophene-2-carboxylate. M+1=369.1

Step 3—Preparation of a Compound of Formula (20) in which R is Hydrogen, $X^2$ is CH, $X^3$ is 5, $X^4$ is CH, $X^5$ is N, and Y is 4-(4-cyclopropyl-1H-imidazol-1-yl)

Methyl 4-(4-(4-cyclopropyl-1H-imidazol-1-yl)picolinamido)thiophene-2-carboxylate (380 mg, 1.0 mmol) was dissolved in ethanol, hydrazine hydrate (0.26 mL, 5.2 mmol) was added, and the reaction was refluxed overnight. The solvent was removed under reduced pressure, and the solids were suspended in acetonitrile and filtered to afford 380 mg of 4-(4-cyclopropyl-1H-imidazol-1-yl)-N-(5-(hydrazinecarbonyl)thiophen-3-yl)picolinamide as a white solid. M+1=369.1

B. Preparation of other Compounds of Formula (20)

Similarly, following the procedure of Example 2A, other compounds of formula (20) are prepared.

EXAMPLE 3

Preparation of a Compound of Formula (2)

A. Preparation of a Compound of Formula (2) in which $R^1$ is Cyclopropyl, $X^2$ is N, $X^3$ is S, and $X^4$ is CH

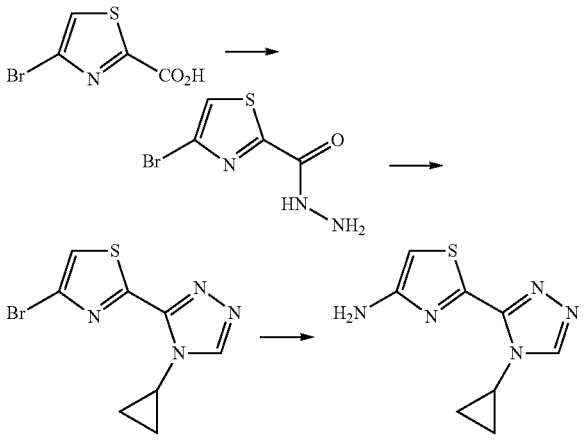

Step 1—Preparation of a Compound of Formula (6) in which $X^2$ is N, $X^3$ is S, and $X^4$ is CH To a solution of 4-bromothiazole-2-carboxylic acid (2.0 g, 9.8 mmol) in methanol (10 mL) was added thionyl chloride (710 μL, 9.8 mmol) and the mixture was refluxed for 3 hours. The solvent was removed under reduced pressure, and the residue was suspended in ethanol (10 mL). To this suspension was added hydrazine hydrate (2.4 mL, 49 mmol), and the reaction was heated to reflux for 90 minutes. The solvent was removed under reduced pressure, and the residue suspended in acetonitrile, filtered, and the solids were washed with acetonitrile, diethyl ether, and dried under vacuum to afford 1.7 g (77%) of 4-bromothiazole-2-carbohydrazide as a yellow solid. M+1=222.1

Step 2—Preparation of a Compound of Formula (7 in which $R^1$ is Cyclopropyl, $X^2$ is N, $X^3$ is S, and $X^4$ is CH The 4-bromothiazole-2-carbohydrazide (620 mg, 2.8 mmol) and toluene (9 mL) were added to a sealable vial, and N,N-dimethylformamide/N,N-dimethylacetamide complex (920 μL, 6.9 mmol) was added. The mixture was stirred for 5 minutes, then cyclopropyl amine (770 μL, 11 mmol), and acetic acid (160 μL, 2.8 mmol) were added, and the reaction was heated in a microwave reactor at 150° C. for 30 minutes. The solvent was removed under reduced pressure, and the residue purified by flash chromatography (1→7% methanol in methylene chloride) to afford 740 mg of 4-bromo-2-(4-cyclopropyl-4H-1,2,4-triazol-3-yl)thiazole (contaminated with DMF•DMA, but used directly in next step).

Step 3-Preparation of a Compound of Formula (2) in which $R^1$ is Cyclopropyl, $X^2$ is N, $X^3$ is S, and $X^4$ is CH The product of Step 2 (1.0 g, 3.7 mmol) was placed in a microwave vial, $Cu(acac)_2$ (97 mg, 0.37 mmol) and caesium carbonate (2.4 g, 7.4 mmol) were added, and the flask was charged with nitrogen. Pentadione (150 μL, 1.5 mmol), N,N-dimethylformamide (8 mL), and ammonium hydroxide (1.1 ml, 300 μL/mmol) were added and the reaction was heated to 90° C. After about 4 hours the reaction was judged to be complete by HPLC (~4 hrs), and the resulting mixture was filtered through celite, the celite was washed with methylene chloride. The solvent was removed under reduced pressure, and the residue was purified by flash chromatography (6→13% methanol in methylene chloride) to provide 480 mg (63%) of 2-(4-cyclopropyl-4H-1,2,4-triazol-3-yl)thiazol-4-amine as an oil. M+1=208.2

B. Preparation of a Compound of Formula (2) in which $R^1$ is Cyclopropyl, $X^2$ is N, $X^3$ is CH, $X^4$ is S, $X^5$ is N, and Z is Bromo Similarly, following the procedure of Example 3A, but replacing cyclopropylamine in Step 2 with (S)-1,1,1-trifluoropropan-2-amine, (S)-2-(4-(1,1,1-trifluoropropan-2-yl)-4H-1,2,4-triazol-3-yl)thiazol-4-amine was prepared. (1.3 g) M+1=264.1.

Similarly, following the procedure of Example 3A, but replacing cyclopropylamine in Step 2 with isopropylamine, 2-(4-isopropyl-4H-1,2,4-triazol-3-yl)thiazol-4-amine was prepared. M+1=210.1

Similarly, following the procedure of Example 3A, but replacing cyclopropylamine in Step 2 with (S)-3-methylbutan-2-amine, (S)-2-(4-(3-methylbutan-2-yl)-4H-1,2,4-triazol-3-yl)thiazol-4-amine was prepared. M+1=238.2

C. Preparation of other Compounds of Formula (2)

Similarly, following the procedure of Example 3A, but optionally replacing 4-bromothiazole-2-carboxylic acid with other compounds of formula (c), and optionally replacing cyclopropylamine with other amines, other compounds of formula (2) are prepared.

EXAMPLE 4

Preparation of a Compound of Formula (1)

Preparation of a Compound of Formula (1) in which $R^2$ is 4-cyclopropyl-1H-imidazole and $X^5$ is $C(R^3)$, in which $R^3$ is Methoxy

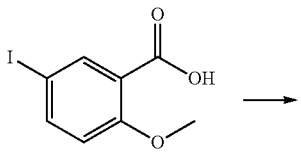

-continued

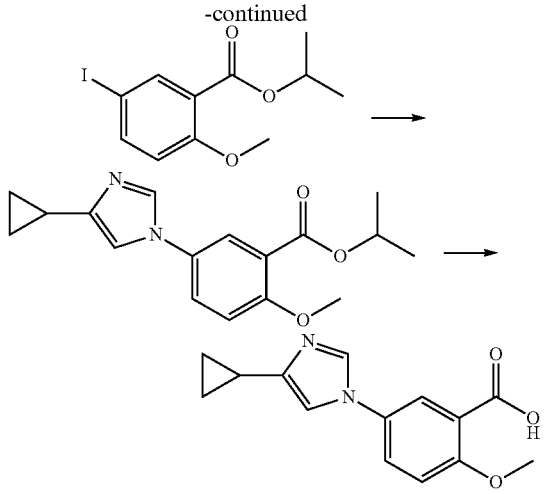

Step 1—Preparation of Isopropyl 5-iodo-2-methoxybenzoate 5-iodo-2-methoxybenzoic acid (2.0 g, 7.2 mmol) was suspended in anhydrous dichloromethane (40 ml). To this suspension was added, with stirring under nitrogen, oxalyl chloride (0.754 ml, 8.62 mmol). N,N-dimethylformamide (0.035 ml) was then added dropwise to the reaction mixture, and the mixture stirred for 1 hour at room temperature. When the intermediate acid chloride was fully formed as demonstrated by LC/MS, isopropanol (20 ml) was slowly added, then after 15 minutes solid sodium bicarbonate (2 g) was slowly added. The reaction was diluted with 40 ml of 1:1 saturated sodium bicarbonate and water, and the aqueous phase extracted with dichloromethane (3×40 ml). The organic extracts were combined, dried over magnesium sulfate, and solvent removed under reduced pressure. The residue was purified by column chromatography (0 to 50% ethyl acetate in hexanes) to afford isopropyl 5-iodo-2-methoxybenzoate as an oil (1.6 g, 5.0 mmol). 69% yield. 321 (M+1).

Step 2—Preparation of isopropyl 5-(4-cyclopropyl-1H-imidazol-1-yl)-2-methoxy-benzoate A suspension of isopropyl 5-iodo-2-methoxybenzoate (1.52 g, 4.75 mmol), 4-cyclopropyl-1H-imidazole (0.777 g, 7.13 mmol), copper(I) oxide (0.067 g, 0.047 mmol), 8-hydroxyquinoline (0.103 g, 0.71 mmol), cesium carbonate (2.41 g, 7.41 mmol), PEG-3350 (1.18 g) and butyronitile (60 ml) was placed in a sealed tube, which was flushed with nitrogen and heated at 120° C. for 16 hours. The solvent was removed under reduced pressure, and the residue was purified by reversed phase HPLC to provide isopropyl 5-(4-cyclopropyl-1H-imidazol-1-yl)-2-methoxybenzoate. (0.720 g, 2.4 mmol). 51% yield. 301 (M+1).

Step 3—Preparation of 5-(4-cyclopropyl-1H-imidazol-1-yl)-2-methoxybenzoic acid

A solution of isopropyl 5-(4-cyclopropyl-1H-imidazol-1-yl)-2-methoxybenzoate (0.720 g, 2.4 mmol) in 2N hydrochloric acid (10 ml) was heated to 100° C. for 10 hours. The solvent was removed under reduced pressure to give 5-(4-cyclopropyl-1H-imidazol-1-yl)-2-methoxybenzoic acid (HCl salt) as a brown powder. (0.715 g, 2.4 mmol). 100% yield. 259 (M+1).

EXAMPLE 5

Preparation of a Compound of Formula (1)

Preparation of a Compound of Formula (1) in which $R^2$ is 4-cyclopropyl-1H-imidazole and $X^5$ is $C(R^3)$, in which $R^3$ is Fluoro

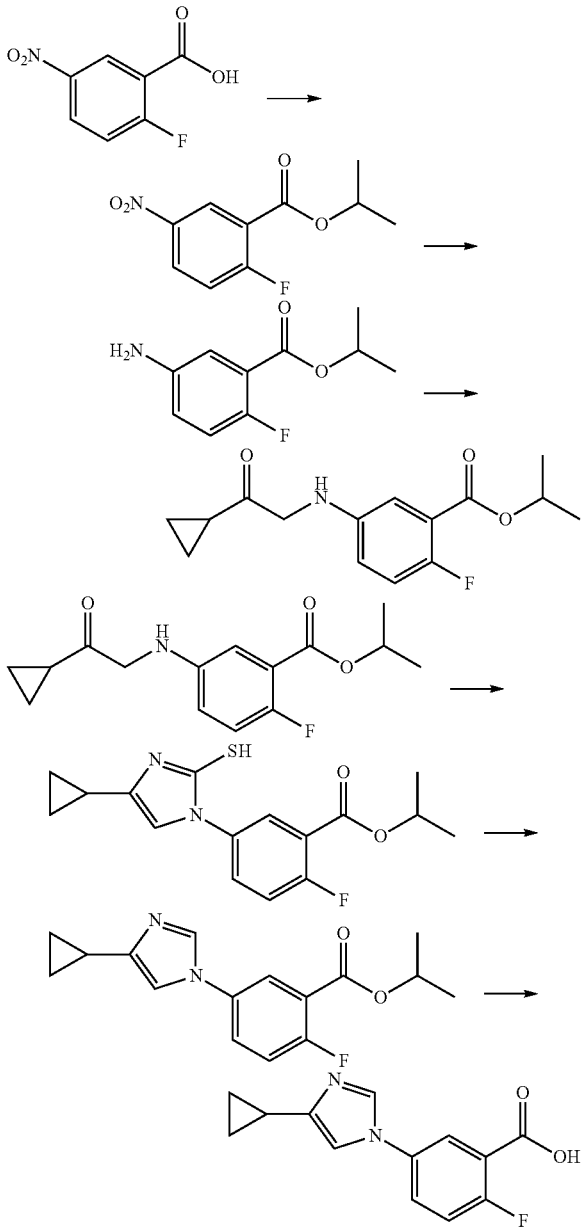

Step 1-Preparation of isopropyl 2-fluoro-5-nitrobenzoate 2-fluoro-5-nitrobenzoic acid (2.5 g, 13.5 mmol) was suspended in anhydrous dichloromethane (60 ml), and with stirring under nitrogen oxalyl chloride (1.41 ml, 16.2 mmol) was added. N,N-dimethylformamide (0.070 ml) was added dropwise to the reaction, and the mixture stirred for 1 hour at room temperature. When the acid chloride was fully formed (as shown by LC/MS) isopropanol (30 ml) was slowly added, followed by after 15 minutes solid sodium bicarbonate (2 g). The reaction was diluted with 40 ml of 1:1 saturated sodium bicarbonate and water, and the aqueous phase extracted with dichloromethane (3×50 ml). The organic extracts were combined, dried over magnesium sulfate, and the solvent removed under resuced pressure. The residue was purified by column chromatography (0 to 40% ethyl acetate in hexanes) to afford isopropyl 2-fluoro-5-nitrobenzoate. (3.06 g, 13.5 mmol). 100% yield. 228 (M+1).

Step 2-Preparation of isopropyl 5-amino-2-fluorobenzoate

Isopropyl 2-fluoro-5-nitrobenzoate (2.86 g, 12.6 mmol) was dissolved in glacial acetic acid (40 ml), and zinc dust (8.12 g, 126 mmol) was added as a solid with stirring under nitrogen. The mixture was stirred for 1 hour at room temperature, then the zinc filtered off and discarded. The solvent was removed under reduced pressure, and the residue was purified by column chromatography (0 to 75% ethyl acetate in hexanes) to afford isopropyl 5-amino-2-fluorobenzoate. (2.48 g, 12.6 mmol). 100% yield. 199 (M+1).

Step 3-Preparation of isopropyl 5-(2-cyclopropyl-2-oxoethylamino)-2-fluorobenzoate Isopropyl 5-amino-2-fluorobenzoate (2.48 g, 12.6 mmol) was suspended in 60 ml absolute ethanol, and with stirring under nitrogen 2-bromo-1-cyclopropylethanone was added, followed by N-methylmorpholine (4.17 ml, 37.8 mmol). The mixture was heated to 60° C. for 16 hours, after which the solvents were removed under reduced pressure. The residue was taken up in dichloromethane (200 ml) and washed with 100 ml water. The organic layer was collected and dried over magnesium sulfate, and the solvent removed under reduced pressure. The residue was purified by column chromatography (0 to 35% ethyl acetate in hexane gradient) to afford isopropyl 5-(2-cyclopropyl-2-oxoethylamino)-2-fluorobenzoate. (2.00 g, 7.2 mmol). 57% yield. 280 (M+1).

Step 4-Preparation of isopropyl 5-(4-cyclopropyl-2-mercapto-1H-imidazol-1-yl)-2-fluorobenzoate Isopropyl 5-(2-cyclopropyl-2-oxoethylamino)-2-fluorobenzoate (1.1 g, 3.94 mmol) was dissolved in glacial acetic acid (30 mL), and with stirring under nitrogen potassium thiocyanate (0.383 g, 3.94 mmol) was added as a solid. The mixture was stirred for 12 hours at room temperature. When the reaction was complete as shown by LC/MS, the solvents were removed under reduced pressure. The product was dissolved in dichloromethane (200 ml) and washed with 100 ml water. The aqueous was extracted with 100 ml additional dichloromethane. The organics were combined and dried over magnesium sulfate. The solvent was removed under reduced pressure, and the residue purified by column chromatography (0 to 50% ethyl acetate in hexanes gradient) to afford isopropyl 5-(4-cyclopropyl-2-mercapto-1H-imidazol-1-yl)-2-fluorobenzoate. (0.776 g, 2.43 mmol). 62% yield. 321 (M+1).

Step 5-Preparation of isopropyl 5-(4-cyclopropyl-1H-imidazol-1 yl)-2-fluorobenzoate Isopropyl 5-(4-cyclopropyl-2-mercapto-1H-imidazol-1-yl)-2-fluorobenzoate (0.776 g, 2.43 mmol) was suspended in a water (16 ml) and fuming nitric acid (4 ml) mixture. The mixture was stirred under nitrogen at 100° C. while monitoring by LC/MS. When the reaction was complete heat was removed and ammonium hydroxide was added to bring the pH to neutral. The solvent was removed under reduced pressure and the residue purified by column chromatography to afford isopropyl 5-(4-cyclopropyl-1H-imidazol-1-yl)-2-fluorobenzoate. (0.306 g, 1.06 mmol). 44% yield. 289 (M+1).

Step 6-Preparation of 5-(4-cyclopropyl-1H-imidazol-1-yl)-2-fluorobenzoic acid

A solution of isopropyl 5-(4-cyclopropyl-1H-imidazol-1-yl)-2-fluorobenzoate (0.306 g, 1.06 mmol) in 2N hydrochloric acid (10 ml) was heated to 100° C. for 10 hours. The solvent was removed under reduced pressure to afford 5-(4-cyclopropyl-1H-imidazol-1-yl)-2-fluorobenzoic acid as the hydrochloride salt, as a brown powder. (0.260 g, 1.06 mmol). 100% yield. 247 (M+1).

EXAMPLE 6

Preparation of a Compound of Formula (1)

Preparation of a Compound of Formula (1) in which $R^2$ is 4-cyclopropyl-1H-imidazole and $X^5$ is N

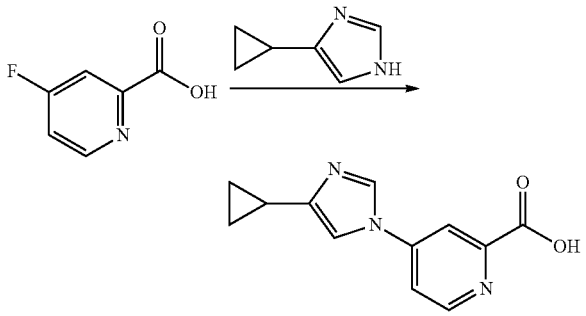

A mixture of 4-fluoropicolinic acid (400 mg, 2.84 mmol) and 4-cyclopropyl-1H-imidazole (322 mg, 2.98 mmol) were dissolved in N,N-dimethylformamide, and N-methylmorpholine (0.36 ml, 3.28 mmol) was added. The reaction was warmed to 35° C., and stirred for 20 hours. The solvent was then removed under reduced pressure to afford a viscous oily residue. This residue was dissolved in 1N hydrochloric acid (5 mL), and the aqueous layer was extracted with ethyl acetate (2×5 mL). The aqueous layer was concentrated under reduced pressure to afford a yellow solid. To this residue was added 5 mL of acetonitrile/methanol (20:1) and the mixture was sonicated to afford a fine suspension of solids. The solids were collected by filtration, washed several times with acetonitrile, and dried on the filter funnel. The yellow solids were collected to afford 520 mg (69% yield) of 4-(4-cyclopropyl-1H-imidazol-1-yl)picolinic acid as the hydrochloride salt. M+1=230.1

EXAMPLE 7

Preparation of a Compound of Formula (I)

A. Preparation of a Compound of Formula (I) in which R is Hydrogen, $R^1$ is Cyclopropyl, $R^2$ is 3-Pyridyl, $X^1$ is N, $X^2$ and $X^4$ are CH, $X^3$ is S, and $X^5$ is N

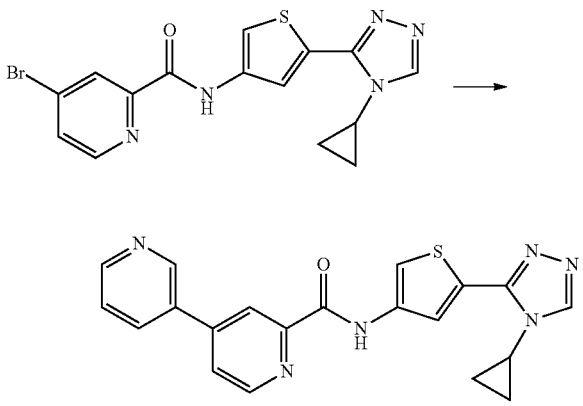

A suspension of 4-bromo-N-(5-(4-cyclopropyl-4H-1,2,4-triazol-3-yl)thiophen-3-yl)picolinamide (55 mg, 0.14 mmol), 3-pyridine boronic acid (17 mg, 0.14 mmol), dppf (Pd)Cl2 (5.2 mg, 0.0071 mmol), potassium carbonate (49 mg, 0.35 mmol) in degassed toluene (0.70 mL), degassed water (0.35 mL) and degassed ethanol (0.35 mL) was heated at 90° C. for 3 hours. The aqueous layer was separated, the organic layer was concentrated under reduced pressure, and the residue was purified by reverse-phase HPLC to give N-(5-(4-cyclopropyl-4H-1,2,4-triazol-3-yl)thiophen-3-yl)-3,4'-bipyridine-2'-carboxamide as a white powder (11 mg, 20% yield). N-(5-(4-cyclopropyl-4H-1,2,4-triazol-3-yl)thiophen-3-yl)-3,4'-bipyridine-2'-carboxamide; $C_{20}H_{16}N_6OS$. 389.2 (M+1). $^1$H NMR (DMSO) δ 11.45 (s, 1H), 9.11 (d, J=2 Hz, 1H), 8.85 (d, J=5 Hz, 1H), 8.70-8.74 (m, 1H), 8.60 (s, 1H), 8.49 (s, 1H), 8.31-8.36 (m, 2H), 8.10 (dd, J=2, 5 Hz, 1H), 8.06 (s, 1H), 7.60 (dd, J=5, 8 Hz, 1H), 3.56-3.59 (m, 1H), 1.11-1.27 (m, 4H).

B. Preparation of Compounds of Formula (I) varying R, $R^1$, $R^2$, $X^1$, $X^2$, $X^3$, $X^4$ and $X^5$ Similarly, following the procedure of Example 7A, but optionally replacing 4-bromo-N-(5-(4-cyclopropyl-4H-1,2,4-triazol-3-yl)thiophen-3-yl)picolinamide by other compounds of formula (4), and optionally replacing 3-pyridine boronic acid by other appropriate boronic acid derivatives, the following compounds of Formula (I) were prepared.

N-(5-(4-cyclopropyl-4H-1,2,4-triazol-3-yl)thiophen-3-yl)-4-phenylpicolinamide;

$C_{21}H_{17}N_5OS$. 388.0 (M+1), $^1$H NMR (DMSO) δ 11.43 (s, 1H), 8.81 (d, J=5 Hz, 1H), 8.60 (s, 1H), 8.43 (s, 1H), 8.32-8.35 (m, 1H), 8.01-8.07 (m, 2H), 7.91 (d, J=7 Hz, 1H), 7.52-7.62 (m, 3H), 3.56-3.59 (m, 1H), 1.23-1.27 (m, 2H), 1.12-1.14 (m, 2H).

6-cyclopropyl-N-(5-(4-cyclopropyl-4H-1,2,4-triazol-3-yl)thiophen-3-yl)-3,4'-bipyridine-2'-carboxamide;

$C_{23}H_{20}N_6OS$. 429.3 (M+1), $^1$H NMR (DMSO) δ 11.43 (s, 1H), 8.93 (d, J=2 Hz, 1H), 8.81 (d, J=7 Hz, 1H), 8.60 (s, 1H), 8.44 (s, 1H), 8.34 (s, 1H), 8.19 (dd, J=2, 8 Hz, 1H), 8.03-8.06 (m, 2H), 7.49 (d, J=8 Hz, 1H), 3.56-3.59 (m, 1H), 2.20-2.23 (m, 1H), 1.23-1.27 (m, 2H), 1.00-1.14 (m, 6H).

N-(4-(4-cyclopropyl-4H-1,2,4-triazol-3-yl)thiazol-2-yl)-6-methoxy-3,4'-bipyridine-T-carboxamide;

$C_{20}H_{17}N_7O_2S$. 420.0 (M+1). $^1$H NMR (DMSO) δ 12.45 (s, 1H), 8.83 (d, J=6 Hz, 1H), 8.79 (d, J=3 Hz, 1H), 8.62 (s, 1H), 8.49 (s, 1H), 8.30 (dd, J=2, 5 Hz, 1H), 8.09 (dd, J=2, 6 Hz, 1H), 7.97 (s, 1H), 7.02 (d, J=8 Hz, 1H), 3.95 (s, 3H), 3.94-4.00 (m, 1H), 1.00-1.11 (m, 4H).

N-(4-(4-cyclopropyl-4H-1,2,4-triazol-3-yl)thiazol-2-yl)-3,4'-bipyridine-2'-carboxamide;

390.1 (M+1). $^1$H NMR ($CD_3OD$) δ 9.04 (s, 1H), 8.88 (d, J=5 Hz, 1H), 8.69 (d, J=8 Hz, 1H), 8.59 (s, 2H), 8.41 (s, 1H), 8.33 (d, J=8 Hz, 1H), 8.02 (dd, J=1, 5 Hz, 1H), 7.96 (s, 1H), 7.64 (dd, J=5, 8 Hz, 1H), 3.80-3.85 (m, 1H), 1.21-1.26 (m, 2H), 1.08-1.12 (m, 2H).

6-cyclopropyl-N-(2-(4-cyclopropyl-4H-1,2,4-triazol-3-yl)thiazol-4-yl)-3,4'-bipyridine-2'-carboxamide;

$C_{22}H_{19}N_7OS$. 430.1 (M+1), $^1$H NMR (DMSO) δ 11.09 (s, 1H), 8.94 (d, J=5 Hz, 1H), 8.75 (s, 1H), 8.47 (d, J=1 Hz, 1H), 8.20 (dd, J=2, 8 Hz, 1H), 8.08 (dd, J=2, 5 Hz, 1H), 8.04 (s, 1H), 7.50 (d, J=8 Hz, 1H), 4.06-4.12 (m, 1H), 2.18-2.23 (m, 1H), 1.02-1.19 (m, 8H);

N-(2-(4-cyclopropyl-4H-1,2,4-triazol-3-yl)thiazol-4-yl)-3,4'-bipyridine-2'-carboxamide;

$C_{19}H_{15}N_7OS$. 490.0 (M+1). $^1$H NMR (DMSO) δ 11.12 (s, 1H), 9.13 (d, J=2 Hz, 1H), 8.87 (d, J=5 Hz, 1H), 8.75 (s, 1H), 8.73 (dd, J=1, 4 Hz, 1H), 8.51 (d, J=1 Hz, 1H), 8.35 (d, J=7 Hz, 1H), 8.14 (dd, J=2, 5 Hz, 1H), 7.61 (dd, J=5, 8 Hz, 1H), 4.08-4.12 (m, 1H), 1.08-1.18 (m, 4H);

N-(5-(4-cyclopropyl-4H-1,2,4-triazol-3-yl)thiophen-3-yl)-5-(6-cyclopropylpyridin-3-yl)-2-methoxybenzamide; $C_{25}H_{23}N_5O_2S$. 458.2 (M+1), $^1$H NMR (DMSO) δ 10.67 (s, 1H), 8.68 (d, J=2 Hz, 1H), 8.56 (s, 1H), 7.97 (s, 1H), 7.91 (d, J=8 Hz, 1H), 7.80-7.84 (m, 3H), 7.33 (d, J=6 Hz, 1H), 7.25 (d, J=6 Hz, 1H), 3.89 (s, 3H), 3.53 (m, 1H), 2.12 (m, 1H), 1.12-1.15 (m, 2H), 1.08-1.11 (m, 2H), 0.91-0.95 (m, 4H). and N-(5-(4-cyclopropyl-4H-1,2,4-triazol-3-yl)thiophen-3-yl)-5-(6-cyclopropylpyridin-3-yl)-2,4-dimethoxybenzamide; GS-493153. $C_{26}H_{25}N_5O_3S$. 488.2 (M+1). $^1$H NMR (DMSO) δ 10.39 (s, 1H), 8.56 (s, 1H), 8.46 (s, 1H), 8.01 (s, 1H), 7.82 (s, 1H), 7.68 (dd, J=1, 8 Hz, 1H), 7.65 (s, 1H), 7.29 (d, J=6 Hz, 1H), 6.86 (s, 1H), 4.01 (s, 3H), 3.88 (s, 3H), 3.54 (m, 1H), 2.09 (m, 1H), 1.14-1.17 (m, 2H), 1.06-1.10 (m, 2H), 0.90-0.93 (m, 4H).

C. Preparation of Compounds of Formula (I) varying R, $R^1$, $R^2$, $X^1$, $X^2$, X3, $X^4$ and $X^5$ Similarly, following the procedure of Example 7A, but optionally replacing 4-bromo-N-(5-(4-cyclopropyl-4H-1,2,4-triazol-3-yl)thiophen-3-yl)picolinamide by other compounds of formula (4), and optionally replacing 3-pyridine boronic acid by other appropriate boronic acid derivatives, other compounds of Formula (I) are prepared.

EXAMPLE 8

Preparation of a Compound of Formula (I)

A. Preparation of a Compound of Formula (I) in which R is Hydrogen, $R^1$ is Cyclopropyl, $R^2$ is 4-Cyclopropylimidazolyl, $X^1$ is N, $X^2$ and $X^4$ are CH, $X^3$ is S, and $X^5$ is N

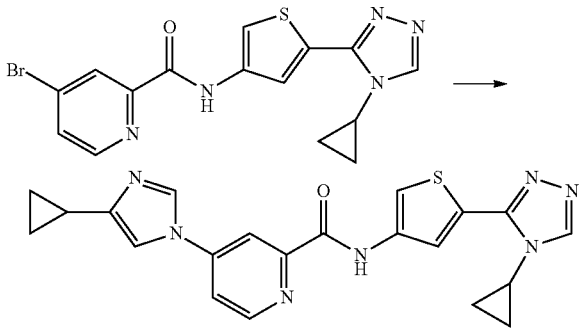

A suspension 4-bromo-N-(5-(4-cyclopropyl-4H-1,2,4-triazol-3-yl)thiophen-3-yl)picolinamide (63 mg, 0.16 mmol), 4-cyclopropyl imidazole (35 mg, 0.24 mmol), $Cu_2O$ (1.2 mg, 0.0081 mmol), 4,7-dimethoxy-1,10-phenanthroline (5.9 mg, 0.024 mmol, (or 8-hydroxy-quinoline may be used as the ligand with comparable results), cesium carbonate (116 mg, 0.36 mmol), and PEG-3350 (32 mg) in butyronitrile (1 L was heated at 100° C. for 16 hours. The solvent was removed and the residue was purified by reverse-phase HPLC to 4-(4-cyclopropyl-1H-imidazol-1-yl)-N-(5-(4-cyclopropyl-4H-1,2,4-triazol-3-yl)thiophen-3-yl)picolinamide as a white powder (9.2 mg, 0.377 mmol, 13% yield). $C_{21}H_{19}N_7OS$. 418.2 (M+1). $^1$H NMR (DMSO) δ 11.42 (s, 1H), 8.77 (s, 1H), 8.60 (s, 1H), 8.54 (s, 1H), 8.37 (d, J=2 Hz, 1H), 8.33 (d, J=2 Hz, 1H), 8.04 (d, J=1 Hz, 1H), 7.97 (dd, J=2, 5 Hz, 1H), 7.85 (s, 1H), 3.55-3.59 (m, 1H), 1.85-1.88 (m, 1H), 1.22-1.26 (m, 2H), 1.11-1.13 (m, 2H), 0.82-0.86 (m, 2H), 0.72-0.75 (m, 2H).

B. Preparation of Compounds of Formula (I) varying R, $R^1$, $R^2$, $X^1$, $X^2$, X3, $X^4$ and $X^5$ Similarly, following the procedure of Example 8A, but optionally replacing 4-bromo-N-(5-(4-cyclopropyl-4H-1,2,4-triazol-3-yl)thiophen-3-yl)picolinamide by other compounds of formula (4), and optionally replacing 4-cyclopropyl imidazole by other appropriate aminoimidazole derivatives, the following compounds of Formula (I) were prepared.

4-(1H-benzo[d]imidazol-1-yl)-N-(4-(4-cyclopropyl-4H-1,2,4-triazol-3-yl)thiazol-2-yl)picolinamide; $C_{21}H_{16}N_8OS \times HCO_2H$. 429.1 (M+1). $^1$H NMR ($CD_3OD$) δ 8.97 (d, J=4 Hz, 1H), 8.76 (s, 1H), 8.56 (s, 1H), 8.52-8.68 (br s, 1H), 8.14 (s, 1H), 8.04 (d, J=4 Hz, 1H), 7.97 (s, 1H), 7.89 (d, J=8 Hz, 1H), 7.82 (d, J=8 Hz, 1H), 7.41-7.50 (m, 2H), 3.78-3.83 (m, 1H), 1.22-1.26 (m, 2H), 1.05-1.10 (m, 2H);

3-(4-cyclopropyl-1H-imidazol-1-yl)-N-(2-(4-cyclopropyl-4H-1,2,4-triazol-3-yl)thiazol-4-yl)benzamide; $C_{21}H_{19}N_7OS$. 418.1 (M+1), $^1$H NMR (DMSO) δ 11.53 (s, 1H), 8.75 (s, 1H), 8.22 (s, 1H), 8.19-8.21 (m, 1H), 8.05 (s, 1H), 7.93 (d, J=7 Hz, 1H), 7.84 (d, J=7 Hz, 1H), 7.65 (t, J=8 Hz, 1H), 7.60 (s, 1H), 3.98-4.03 (m, 1H), 1.85-1.89 (m, 1H), 1.12-1.17 (m, 4H), 0.69-0.84 (m, 4H).

4-(4-cyclopropyl-1H-imidazol-1-yl)-N-(2-(4-cyclopropyl-4H-1,2,4-triazol-3-yl)thiazol-4-yl)-5-methylpicolinamide; GS-557119. $C_{21}H_{20}N_8OS.HCl$. 433.1. (M+1). $^1$H NMR (DMSO) δ 11.18 (s, 1H), 9.42 (s, 1H), 8.90 (s, 1H), 8.76 (s, 1H), 8.31 (s, 1H), 8.01 (s, 1H), 7.90 (s, 1H), 4.08-4.11 (m, 1H), 2.42 (s, 3H), 2.02-2.05 (m, 1H), 1.02-1.11 (m, 6H), 0.87-0.89 (m, 2H).

4-(4-cyclopropyl-1H-imidazol-1-yl)-N-(5-(4-cyclopropyl-4H-1,2,4-triazol-3-yl)thiophen-3-yl)-5-methylpicolinamide; GS-557120. $C_{22}H_{21}N_7OS.HCl$. 432.2. (M+1). $^1$H NMR (DMSO) δ 11.52 (s, 1H), 9.45 (s, 1H), 8.90 (s, 1H), 8.84 (s, 1H), 8.34 (d, J=1.6 Hz, 1H), 8.29 (s, 1H), 8.08 (d, J=1.2 Hz, 1H), 7.91 (s, 1H), 3.57-3.61 (m, 1H), 2.42 (s, 3H), 2.02-2.06 (m, 1H), 1.03-1.27 (m, 6H), 0.86-0.90 (m, 2H).

4-(4-tert-butyl-1H-imidazol-1-yl)-N-(5-(4-cyclopropyl-4H-1,2,4-triazol-3-yl)thiophen-3-yl)picolinamide; GS-557830. $C_{22}H_{23}N_7OS$. 434.2. (M+1). $^1$H NMR (DMSO) δ 11.43 (s, 1H), 8.77 (d, J=5.6 Hz, 1H), 8.59 (d, J=5.2 Hz, 2H), 8.42 (s, 1H), 8.34 (s, 1H), 8.01-8.05 (m, 2H), 7.80 (s, 1H), 3.55-3.58 (m, 1H), 1.28 (s, 9H), 1.24-1.27 (m, 2H), 1.10-1.13 (m, 2H).

(S)-4-(4-cyclopropyl-1H-imidazol-1-yl)-5-methyl-N-(2-(4-(1,1,1-trifluoropropan-2-yl)-4H-1,2,4-triazol-3-yl)thiazol-4-yl)picolinamide; GS-557832. $C_{21}H_{19}F_3N_8OS.HCl$. 489.2. (M+1). $^1$H NMR (DMSO) δ 11.67 (s, 1H), 9.24 (s, 2H), 8.93 (s, 1H), 8.30 (s, 1H), 8.05 (s, 1H), 7.86 (s, 1H), 6.83-6.88 (m, 1H), 2.44 (s, 3H), 1.99-2.03 (m, 1H), 1.84 (d, J=6.8 Hz, 3H), 1.01-1.05 (m, 2H), 0.84-0.88 (m, 2H). and (S)-4-(4-tert-butyl-1H-imidazol-1-yl)-5-methyl-N-(2-(4-(1,1,1-trifluoropropan-2-yl)-4H-1,2,4-triazol-3-yl)thiazol-4-yl)picolinamide; GS-564768. $C_{22}H_{23}F_3N_8OS.HCl$. 505.2. (M+1).

C. Preparation of Compounds of Formula (I) varying R, $R^1$, $R^2$, $X^1$, $X^2$, X3, $X^4$ and $X^5$ Similarly, following the procedure of Example 8A, but optionally replacing 4-bromo-N-(5-(4-cyclopropyl-4H-1,2,4-triazol-3-yl)thiophen-3-yl)picolinamide by other compounds of formula (4), and optionally replacing 4-cyclopropyl imidazole by other appropriate aminoimidazole derivatives, other compounds of Formula (I) are prepared.

EXAMPLE 9

Preparation of a Compound of Formula (I)

A. Preparation of a Compound of Formula (I) in which R is Hydrogen, $R^1$ is 3-Methylbutan-2-yl, $R^2$ is 4-Cyclopropylimidazolyl, $X^1$ is N, $X^2$ and $X^4$ are CH, $X^3$ is S, and $X^5$ is N

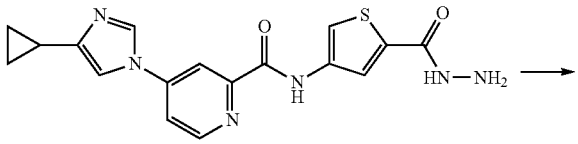

-continued

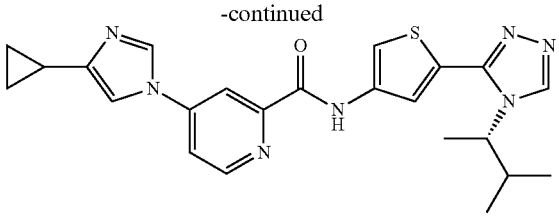

A mixture of 4-(4-cyclopropyl-1H-imidazol-1-yl)-N-(5-(hydrazinecarbonyl)thiophen-3-yl)picolinamide (130 mg, 0.35 mmol) and toluene (2 mL) were added to a sealable vial. N,N-dimethylformamide/N,N-dimethylacetamide complex (120 μL, 0.88 mmol) was added and the reaction was stirred for 5 minutes. (S)-3-methylbutan-2-amine (170 μL, 1.4 mmol), and acetic acid (20 μL, 0.35 mmol) were added, and the reaction was heated in a microwave reactor at 150° C. for 30 minutes. The reaction was concentrated and purified by RP-HPLC to provide 65 mg (42%) of (S)-4-(4-cyclopropyl-1H-imidazol-1-yl)-N-(5-(4-(3-methylbutan-2-yl)-4H-1,2,4-triazol-3-yl)thiophen-3-yl)picolinamide as a white solid.

$C_{23}H_{23}N_7OS$. 448.2. (M+1). $^1$H NMR (DMSO) δ 11.41 (s, 1H), 8.87 (s, 1H), 8.78 (d, J=5 Hz, 1H), 8.55 (d, J=1 Hz, 1H), 8.38 (d, J=2 Hz, 1H), 8.09 (d, J=1 Hz, 1H), 7.98 (dd, J=2, 6 Hz, 1H), 7.94 (d, J=2 Hz, 1H), 7.86 (d, J=1 Hz, 1H), 4.24 (pent, J=8 Hz, 1H), 2.06-2.11 (m, 1H), 1.85-1.89 (m, 1H), 1.49 (d, J=6 Hz, 3H), 0.95 (d, J=6 Hz, 3H), 0.83 (d,
J=3 Hz, 3H), 0.71-0.75 (m, 4H).

B. Preparation of Compounds of Formula (I) varying R, $R^1$, $R^2$, $X^1$, $X^2$, X3, $X^4$ and $X^5$ Similarly, following the procedure of Example 9A, but optionally replacing 4-(4-cyclopropyl-1H-imidazol-1-yl)-N-(5-(hydrazinecarbonyl)thiophen-3-yl)picolinamide by other compounds of formula (6), and optionally replacing (S)-3-methylbutan-2-amine by other appropriate amines, the following compounds of Formula (I) were prepared.

(S)-4-(4-cyclopropyl-1H-imidazol-1-yl)-N-(5-(4-(1,1,1-trifluoropropan-2-yl)-4H-1,2,4-triazol-3-yl)thiophen-3-yl) picolinamide;

$C_{21}H_{18}F_3N_7OS$. 474.1. (M+1). $^1$H NMR (DMSO) δ 11.39 (s, 1H), 9.12 (s, 1H), 8.77 (d, J=5 Hz, 1H), 8.55 (d, J=1 Hz, 1H), 8.38 (d, J=2 Hz, 1H), 8.13 (d, J=1 Hz, 1H), 7.97-8.02 (m, 2H), 7.86 (d, J=1 Hz, 1H), 5.41 (sept, J=7 Hz, 1H), 1.79-1.89 (m, 4H), 0.71-0.86 (m, 4H).

(S)-4-(4-cyclopropyl-1H-imidazol-1-yl)-N-(5-(4-(1-phenylethyl)-4H-1,2,4-triazol-3-yl)thiophen-3-yl)picolinamide;

$C_{26}H_{23}N_7OS$. 482.0. (M+1). $^1$H NMR (DMSO) δ 11.34 (s, 1H), 9.00 (s, 1H), 8.77 (d, J=6 Hz, 1H), 8.54 (d, J=1 Hz, 1H), 8.36 (d, J=2 Hz, 1H), 8.02 (d, J=1 Hz, 1H), 7.97 (dd, J=2, 6 Hz, 1H), 7.94 (d, J=2 Hz, 1H), 7.85 (d, J=1 Hz, 1H), 7.28-7.40 (m, 3H), 7.23 (d, J=7 Hz, 2H), 5.80 (q, J=4 Hz, 1H), 1.85-1.92 (m, 4H), 0.71-0.86 (m, 4H).

4-(4-cyclopropyl-1H-imidazol-1-yl)-N-(5-(4-(3-hydroxybutan-2-yl)-4H-1,2,4-triazol-3-yl)thiophen-3-yl)picolinamide; $C_{22}H_{23}N_7O_2S$. 450.2. (M+1). $^1$HNMR for the major isomer (DMSO) δ 11.36 (s, 1H), 8.75-8.79 (m, 2H), 8.55 (s, 1H), 8.38 (d, J=2 Hz, 1H), 8.06 (d, J=1 Hz, 1H), 7.94-7.99 (m, 2H), 7.86 (s, 1H), 5.19 (d, J=4 Hz, 1H), 4.35 (pent, J=7 Hz, 1H), 3.88-3.94 (m, 1H), 1.84-1.91 (m, 1H), 1.48-1.52 (m, 3H), 1.03-1.05 (m, 3H), 0.82-0.86 (m, 2H), 0.72-0.74 (m, 2H). and 4-(4-cyclopropyl-1H-imidazol-1-yl)-N-(5-(4-(4,4,4-trifluoro-3-hydroxybutan-2-yl)-4H-1,2,4-triazol-3-yl)thiophen-3-yl)picolinamide;

$C_{22}H_{20}F_3N_7O_2S$. 504.1. (M+1). $^1$H NMR for the major isomer (DMSO) δ 11.42 (s, 1H), 8.91 (s, 1H), 8.77 (d, J=6 Hz, 1H), 8.38 (d, J=2 Hz, 1H), 8.11 (d, J=1 Hz, 1H), 7.98 (dd, J=2, 6 Hz, 1H), 7.96 (d, J=1 Hz, 1H), 7.86 (d, J=1 Hz, 1H), 7.16 (d, J=6 Hz, 1H), 4.77 (pent, J=6 Hz, 1H), 4.42 (q, J=6 Hz, 1H), 1.83-1.90 (m, 1H), 1.59 (d, J=6 Hz, 3H), 0.72-0.86 (m, 4H).

(S)-4-(4-cyclopropyl-1H-imidazol-1-yl)-N-(5-(4-(2,2-dimethylcyclopropyl)-4H-1,2,4-triazol-3-yl)thiophen-3-yl) picolinamide; GS-549245. $C_{23}H_{23}N_7OS$. 446.2. (M+1). $^1$H NMR (DMSO) δ 11.34 (s, 1H), 8.71 (d, J=5.2 Hz, 1H), 8.51 (s, 1H), 8.47 (d, J=1.6 Hz, 1H), 8.29 (d, J=2.0 Hz, 1H), 8.10 (d, J=1.6 Hz, 1H), 7.94 (d, J=1.6 Hz, 1H), 7.90 (dd, J=2.4, 5.6 Hz, 1H), 7.78 (d, J=1.2 Hz, 1H), 3.36 (dd, J=3.6, 7.6 Hz, 1H), 1.77-1.84 (m, 1H), 1.22 (s, 3H), 1.15-1.17 (m, 2H), 1.07-1.14 (m, 1H), 0.75-0.79 (m, 2H), 0.66-0.69 (m, 2H) 0.65 (s, 3H).

(R)-4-(4-cyclopropyl-1H-imidazol-1-yl)-N-(5-(4-(2,2-dimethylcyclopropyl)-4H-1,2,4-triazol-3-yl)thiophen-3-yl) picolinamide; GS-549246. $C_{23}H_{23}N_7OS$. 446.2. (M+1). $^1$H NMR (DMSO) δ 11.34 (s, 1H), 8.71 (d, J=5.2 Hz, 1H), 8.51 (s, 1H), 8.47 (d, J=1.6 Hz, 1H), 8.29 (d, J=2.0 Hz, 1H), 8.10 (d, J=1.6 Hz, 1H), 7.94 (d, J=1.6 Hz, 1H), 7.90 (dd, J=2.4, 5.6 Hz, 1H), 7.78 (d, J=1.2 Hz, 1H), 3.36 (dd, J=3.6, 7.6 Hz, 1H), 1.77-1.84 (m, 1H), 1.22 (s, 3H), 1.15-1.17 (m, 2H), 1.07-1.14 (m, 1H), 0.75-0.79 (m, 2H), 0.66-0.69 (m, 2H) 0.65 (s, 3H).

Note: enantiomerically enriched material obtained by separation on Chialcel OJ-H column (250×4.6 mm, 5 micron, 50:50 MeOH:EtOH, isocratic) and the stereochemistry was arbitrarily assigned.

C. Preparation of Compounds of Formula (I) varying R, $R^1$, $R^2$, $X^1$, $X^2$, X3, $X^4$ and $X^5$ Similarly, following the procedure of Example 9A, but optionally replacing 4-(4-cyclopropyl-1H-imidazol-1-yl)-N-(5-(hydrazinecarbonyl)thiophen-3-yl)picolinamide by other compounds of formula (6), and optionally replacing (S)-3-methylbutan-2-amine by other appropriate amines, other compounds of Formula (I) are prepared.

EXAMPLE 10

Preparation of a Compound of Formula (I)

A. Preparation of a Compound of Formula (I) in which R is Hydrogen, $R^1$ is 1,1,1-Trifluoropropan-2-yl, $R^2$ is 4-Cyclopropylimidazolyl, $X^1$ is N, $X^2$ is N, $X^3$ is S $X^4$ is CH, and $X^5$ is N

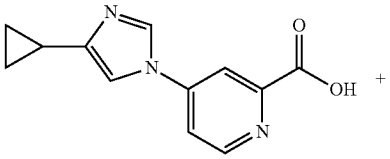

-continued

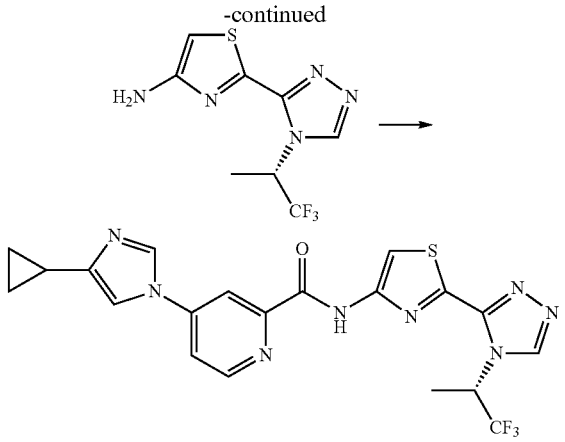

A solution of 4-(4-cyclopropyl-1H-imidazol-1-yl)picolinic acid (50 mg, 0.218 mmol), (S)-2-(4-(1,1,1-trifluoropropan-2-yl)-4H-1,2,4-triazol-3-yl)thiazol-4-amine (53 mg, 0.208 mmol), HATU (99 mg, 0.262 mmol), and N-methylmorpholine (30 μL, 0.262 mmol) in N,N-dimethylformamide (1 mL) was stirred at room temperature for 2 hours. The solvent was removed under reduced pressure, the residue was suspended in acetonitrile/water and the solids were isolated by filtration, washed with water (2 mL), acetonitrile (2 mL) and diethyl ether (5 mL) and dried under vacuum to afford (S)-4-(4-cyclopropyl-1H-imidazol-1-yl)-N-(2-(4-(1,1,1-trifluoropropan-2-yl)-4H-1,2,4-triazol-3-yl)thiazol-4-yl)picolinamide as a white powder (69 mg, 71% yield).

GS-557614. $C_{20}H_{17}F_3N_8OS.HCO_2H$.475.2. (M+1). $^1$H NMR (DMSO) δ 11.56 (s, 1H), 9.23 (s, 1H), 8.80 (d, J=5.6 Hz, 1H), 8.55 (d, J=1.6 Hz, 1H), 8.40 (d, J=2.4 Hz, 1H), 8.31 (s, 0.5H, formate salt), 8.06 (s, 1H), 8.00 (dd, J=2.0, 5.2 Hz, 1H), 7.86 (d, J=2.0 Hz, 1H), 6.80-6.87 (m, 1H), 1.80-1.95 (m, 4H), 0.71-0.86 (m, 4H).

B. Preparation of Compounds of Formula (I) varying R, $R^1$, $R^2$, $X^1$, $X^2$, X3, $X^4$ and $X^5$ Similarly, following the procedure of Example 10A, but optionally replacing 4-(4-cyclopropyl-1H-imidazol-1-yl)picolinic acid by other compounds of formula (1), and optionally replacing (S)-2-(4-(1,1,1-trifluoropropan-2-yl)-4H-1,2,4-triazol-3-yl)thiazol-4-amine by other compounds of formula (2), the following compounds of Formula (I) were prepared.

4-(4-cyclopropyl-1H-imidazol-1-yl)-N-(2-(4-cyclopropyl-4H-1,2,4-triazol-3-yl)thiazol-4-yl)picolinamide; GS-491317. $C_{20}H_{18}N_8OS$. 419.2. (M+1). $^1$H NMR (DMSO) δ 11.09 (s, 1H), 8.77 (d, J=5.6 Hz, 1H), 8.74 (s, 1H), 8.55 (s, 1H), 8.39 (d, J=2.4 Hz, 1H), 8.02 (s, 1H), 7.99 (dd, J=2.4, 6.0 Hz, 1H), 7.85 (s, 1H), 4.05-4.08 (m, 1H), 1.83-1.87 (m, 1H), 1.06-1.17 (m, 4H), 0.70-0.85 (m, 4H).

5-(4-cyclopropyl-1H-imidazol-1-yl)-N-(5-(4-cyclopropyl-4H-1,2,4-triazol-3-yl)thiophen-3-yl)-2-methoxybenzamide; $C_{23}H_{22}N_6O_2S$. 447.1 (M+1). $^1$H NMR (CD3CN) δ 10.06 (s, 1H), 8.55 (s, 1H), 8.27 (m, 2H), 7.94-7.96 (m, 2H), 7.70-7.79 (m, 1H), 7.38-7.44 (m, 2H), 4.14 (s, 3H), 3.49-3.55 (m, 1H), 1.79-1.87 (m, 1H), 1.20-1.29 (m, 2H), 1.08-1.16 (m, 4H), 0.82-0.86 (m, 2H).

5-(4-cyclopropyl-1H-imidazol-1-yl)-N-(2-(4-cyclopropyl-4H-1,2,4-triazol-3-yl)thiazol-4-yl)-2-methoxybenzamide; GS-493572. $C_{22}H_{21}N_7O_2S$. 448.1 (M+1). $^1$H NMR (DMSO) δ 11.19 (s, 1H), 9.22 (bs, 1H), 8.71 (s, 1H), 8.02 (d, J=2 Hz, 1H), 7.81-8.02 (m, 3H), 7.40 (d, J=7 Hz, 1H), 3.96 (s, 3H), 3.80-3.84 (m, 1H), 1.85-1.90 (m, 1H), 1.08-1.11 (m, 4H), 0.96-0.98 (m, 2H), 0.79-0.81 (m, 2H).

4-(4-cyclopropyl-1H-imidazol-1-yl)-N-(2-(4-isopropyl-4H-1,2,4-triazol-3-yl)thiazol-4-yl)picolinamide; GS-548606. $C_{20}H_{20}N_8OS.HCl$. 421.1. (M+1). $^1$H NMR (DMSO) δ 11.28 (s, 1H), 9.43 (s, 1H), 8.98 (s, 1H), 8.93 (d, J=5.6 Hz, 1H), 8.54 (s, 1H), 8.19 (s, 1H), 8.09 (dd, J=2.0, 5.2 Hz, 1H), 8.00 (s, 1H), 5.61 (sept, J=6.4 Hz, 1H), 1.95-1.98 (m, 1H), 1.51 (d, J=6.4 Hz, 6H), 0.96-0.99 (m, 2H), 0.81-0.84 (m, 2H).

(S)-4-(4-cyclopropyl-1H-imidazol-1-yl)-N-(2-(4-(3-methylbutan-2-yl)-4H-1,2,4-triazol-3-yl)thiazol-4-yl)picolinamide; GS-549173. $C_{22}H_{24}N_8OS$. 449.1. (M+1). $^1$H NMR (DMSO) δ 11.20 (s, 1H), 8.97 (s, 1H), 8.79 (d, J=5.2 Hz, 1H), 8.54 (s, 1H), 8.38 (s, 1H), 7.98 (s, 2H), 7.85 (s, 1H), 5.38 (t, J=6.8 Hz, 1H), 2.03-2.09 (m, 1H), 1.82-1.90 (m, 1H), 1.50 (d, J=7.2 Hz, 3H), 0.92 (d, J=6.4 Hz, 3H), 0.82-0.85 (m, 2H), 0.73-0.76 (m, 2H) 0.73 (d, J=6.4 Hz, 3H).

5-(4-cyclopropyl-1H-imidazol-1-yl)-N-(5-(4-cyclopropyl-4H-1,2,4-triazol-3-yl)thiophen-3-yl)-2-fluorobenzamide; GS-549150. $C_{22}H_{19}FN_6OS$. 435.2 (M+1). $^1$H NMR (CD3OD) 89.60 (s, 1H), 9.38 (s, 1H), 8.37 (s, 1H), 8.16 (m, 2H), 7.92-7.94 (m, 1H), 7.86 (s, 1H), 7.57 (t, J=7 Hz, 1H), 3.79-3.83 (m, 1H), 1.97-2.08 (m, 1H), 1.40-1.43 (m, 2H), 1.32-1.38 (m, 2H), 1.13-1.18 (m, 2H), 0.89-0.93 (m, 2H). and 5-(4-cyclopropyl-1H-imidazol-1-yl)-N-(2-(4-cyclopropyl-4H-1,2,4-triazol-3-yl)thiazol-4-yl)-2-fluorobenzamide; GS-549200. $C_{21}H_{18}FN_7OS$. 436.1 (M+1). $^1$HNMR (CD3OD) δ 9.84 (bs, 1H), 9.38 (bs, 1H), 8.08-8.32 (m, 2H), 7.96 (bs, 1H), 7.84 (s, 1H), 7.57 (m, 1H), 4.08-4.18 (m, 1H), 1.97-2.08 (m, 1H), 1.35-1.39 (m, 2H), 1.27-1.31 (m, 2H), 1.11-1.4 (m, 2H), 0.87-0.91 (m, 2H).

C. Preparation of Other Compounds of Formula (I)

Similarly, following the procedure of Example 10A, but optionally replacing 4-(4-cyclopropyl-1H-imidazol-1-yl)picolinic acid by other compounds of formula (1), and optionally replacing (S)-2-(4-(1,1,1-trifluoropropan-2-yl)-4H-1,2,4-triazol-3-yl)thiazol-4-amine by other compounds of formula (2), other compounds of Formula (I) are prepared.

EXAMPLE 11

Preparation of a Compound of Formula (I)

A. Preparation of a Compound of Formula (I) in which R is Hydrogen, $R^1$ is Cyclopropyl, $R^2$ is 4-Cyclopropyl-5-methyl-1H-imidazol-1-yl, $X^1$ is N, $X^2$ is CH, $X^3$ is S, $X^4$ is CH, and $X^5$ is N

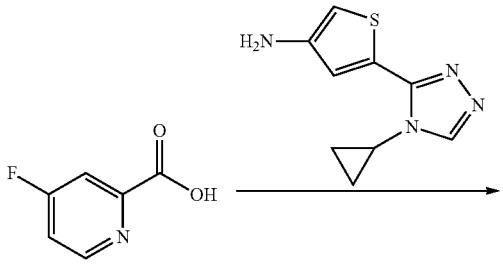

-continued

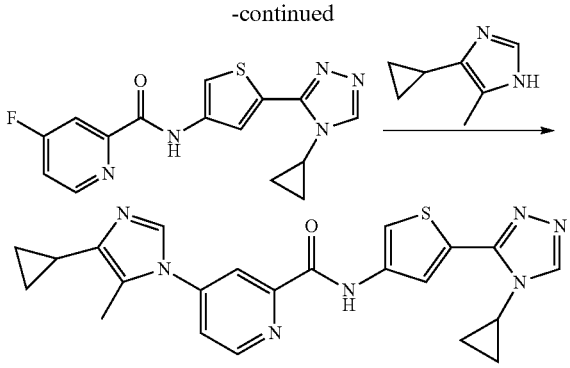

N-(5-(4-cyclopropyl-4H-1,2,4-triazol-3-yl)thiophen-3-yl)-4-fluoropicolinamide was prepared and purified in an analogous fashion to Example 10.

Step 1-Preparation of 4-cyclopropyl-5-methyl-1H-imidazole

4-Cyclopropyl-5-methyl-1H-imidazole was synthesized according to the following procedure: Under nitrogen with stirring formamidine acetate (15.62 g, 150 mmol) was suspended in 40 ml anhydrous ethanol. 2-bromo-1-cyclopropylpropan-1-one (2.64 g, 15 mmol) was added via syringe and the mixture was heated to 60° C. for 2 hours. Triethylamine (21 ml, 155 mmol) was then added and the reaction was heated for an additional 12 hours at 60° C. The solvent was removed under reduced pressure, and the residue was dissolved in 50 ml of water. An aqueous solution of saturated sodium bicarbonate (20 ml) was added, followed by sodium chloride until the solution became saturated. The mixture was placed in a separatory funnel and extracted with ethyl acetate (3×50 ml), the organic extracts combined, dried over magnesium sulfate, filtered and then the solvent removed under reduced pressure. The oily residue was washed with hexanes (2×100 ml) to remove any residual triethylamine, leaving an oily residue which was >90% pure by 1H-NMR, which was further purified by loading onto a silica gel column in ethyl acetate and eluting with 0 to 10% methanol in ethyl acetate. Yield 0.607 g, 33%

Step 2—Preparation of N-(5-(4-cyclopropyl-4H-1,2,4-triazol-3-yl)thiophen-3-yl)-4-(4-cyclopropyl-5-methyl-1H-imidazol-1-yl)picolinamide N-(5-(4-cyclopropyl-4H-1,2,4-triazol-3-yl)thiophen-3-yl)-4-fluoropicolinamide (0.128 g, 0.39 mmol) and 4-cyclopropyl-5-methyl-1H-imidazole (0.05 g, 0.41 mmol) were dissolved in anhydrous N,N-dimethylformamide (4 and with stirring under nitrogen cesium carbonate (0.147 g, 0.45 mmol) was added, and the mixture was heated to 35° C. for 16 hours. Solvent was removed under reduced pressure, the residue washed with water, and filtered. The solid product was collected, re-dissolved in 50:50 acetonitrile:water and the product purified by prep-HPLC (0.080 g, 0.186 mmol). 48% yield 432 (M+1). GS-492197. $C_{22}H_{21}N_7OS$. 432.14 (M+1). $^1$H NMR (CD3CN) δ 10.47 (s, 1H), 8.80 (d, J=4 Hz, 1H), 8.26 (s, 1H), 8.23 (s, 1H), 8.09 (s, 1H), 8.00 (s, 1H), 7.68 (s, 1H), 7.61-7.63 (m, 1H), 3.51-3.53 (m, 1H), 2.35 (s, 3H), 1.86-1.93 (m, 1H), 1.24-1.28 (m, 2H), 1.12-1.14 (m, 2H), 0.81-0.87 (m, 4H).

B. Preparation of Compounds of Formula (I) varying R, $R^1$, $R^2$, $X^1$, $X^2$, X3, $X^4$ and $X^5$ Similarly, following the procedure of Example 11A, but optionally replacing N-(5-(4-cyclopropyl-4H-1,2,4-triazol-3-yl)thiophen-3-yl)-4-fluoropicolinamide by other fluorinated compounds, and optionally replacing 4-cyclopropyl-5-methyl-1H-imidazole by similar compounds, the following compounds of Formula (I) were prepared. N-(5-(4-cyclopropyl-4H-1,2,4-triazol-3-yl)thiophen-3-yl)-4-(4-(pyridin-2-yl)-1H-imidazol-1-yl)picolinamide; GS-492468. $C_{23}H_{18}N_8OS$. 455.1 (M+1). $^1$H NMR (DMSO) δ 11.45 (s, 1H), 8.82-8.83 (m, 2H), 8.54-8.62 (m, 4H), 8.32 (s, 1H), 8.18 (d, J=2 Hz, 1H), 8.05 (s, 1H), 7.97 (d, J=6 Hz, 1H) 7.86 (t, J=1 Hz, 1H), 7.29 (m, 1H), 3.55-3.57 (m, 1H), 1.22-1.25 (m, 2H), 1.10-1.14 (m, 2H);

N-(5-(4-cyclopropyl-4H-1,2,4-triazol-3-yl)thiophen-3-yl)-4-(4-(pyridin-3-yl)-1H-imidazol-1-yl)picolinamide; GS-492962. $C_{23}H_{18}N_8OS$. 455.1 (M+1). $^1$H NMR (DMSO) δ 11.52 (s, 1H), 9.28 (s, 1H), 9.12 (s, 1H), 8.97 (s, 1H), 8.89 (d, J=4 Hz, 1H), 8.80-8.85 (m, 2H), 8.76 (d, J=4 Hz, 1H), 8.54 (s, 1H), 8.37 (s, 1H), 8.13 (d, J=6 Hz, 1H) 8.09 (s, 1H), 8.02 (m, 1H), 3.58-3.61 (m, 1H), 1.23-1.27 (m, 2H), 1.12-1.16 (m, 2H); and.

4-(4-bromo-1H-imidazol-1-yl)-N-(5-(4-cyclopropyl-4H-1,2,4-triazol-3-yl)thiophen-3-yl)picolinamide ; GS-493632. $C_{18}H_{14}BrN_7OS$. 456.0 (M+1). $^1$H NMR (DMSO) δ 11.42 (s, 1H), 8.11 (d, J=4 Hz, 1H), 8.69 (s, 1H), 8.57 (s, 1H), 8.44 (s, 1H), 8.33 (s, 1H), 8.29 (s, 1H), 8.00-8.02 (m, 2H), 3.52-3.7 (m, 1H), 1.21-1.23 (m, 2H), 1.06-1.10 (m, 2H).

C. Preparation of Compounds of Formula (I) varying R, $R^1$, $R^2$, $X^1$, $X^2$, X3, $X^4$ and $X^5$ Similarly, following the procedure of Example 11A, but optionally replacing N-(5-(4-cyclopropyl-4H-1,2,4-triazol-3-yl)thiophen-3-yl)-4-fluoropicolinamide by other fluorinated compounds, and optionally replacing 4-cyclopropyl-5-methyl-1H-imidazole by similar compounds, other compounds of Formula (I) are prepared.

EXAMPLE 12

Biological Assays

ASK1 (Apoptosis Signal-Regulating Kinase 1) TR-FRET Kinase Assay (Biochemical $IC_{50}$)

The ability of compounds to inhibit ASK1 kinase activity was determined using a time resolved fluorescence resonance energy transfer [TR-FRET] assay utilizing biotinylated myelin basic protein [biotin-MBP] as the protein substrate. A Beckman Biomek FX liquid handling robot was utilized to spot 2 μL/well of compounds in 2.44% aqueous DMSO into low volume 384-well polypropylene plates [Nunc, #267460] to give a final concentration of between 100 μM and 0.5 nM compound in the kinase assay. A Deerac Fluidics Equator was used to dispense 3 μL/well of 0.667 ng/μL [Upstate Biotechnologies, #14-606, or the equivalent protein prepared in-house] and 0.1665 ng/mL biotin-MBP [Upstate Biotechnologies, #13-111] in buffer (85 mM MOPS, pH 7.0, 8.5 mM Mg-acetate, 5% glycerol, 0.085% NP-40, 1.7 mM DTT and 1.7 mg/mL BSA) into the plates containing the spotted compounds. The enzyme was allowed to pre-incubate with compound for 20 minutes prior to initiating the kinase reaction with the addition of 5 μL/well 300 μM ATP in buffer (50 mM MOPS, pH 7.0, 5 mM Mg-acetate, 1 mM DTT, 5% DMSO) using the Deerac Fluidics Equator. The kinase reactions were allowed to proceed for 20 minutes at ambient temperature and were subsequently stopped with the addition of 5 μL/well 25 mM EDTA using the Deerac Fluidics Equator. The Biomek FX was then used to transfer 1 μL/well of each completed kinase reaction to the wells of an OptiPlate-1536 white polystyrene plate [PerkinElmer, #6004299] that contained 5 μL/well detection reagents (1.11 nM Eu-W1024 labeled anti-phosphothreonine antibody [PerkinElmer, #AD0094] and 55.56 nM streptavidin allophycocyanin [PerkinElmer, #CR130-100] in 1×LANCE detection buffer [PerkinElmer, #CR97-100]). The TR-FRET signal was then read on a Perkin Elmer Envision plate reader after incubating the plates at ambient temperature for 2 hours. The 100% inhibition positive control wells were generated by switching the order of addition of the EDTA and ATP solutions described above. These wells and 0% inhibition wells containing spots of 2.44% DMSO at the beginning of the assay were used in calculating the % inhibition for the test compounds.

When tested by the above method, the compounds of Formula (I) inhibited ASK1. For example;

| No. | Compound | IC50 |
|---|---|---|
| 1 | N-(5-(4-cyclopropyl-4H-1,2,4-triazol-3-yl)-thiophen-3-yl)-4-phenylpicolinamide | 191 |
| 2 | 4-(4-cyclopropyl-1H-imidazol-1-yl)-N-(5-(4-cyclopropyl-4H-1,2,4-triazol-3-yl)thiophen-3-yl)picolinamide | 10 |
| 3 | N-(5-(4-cyclopropyl-4H-1,2,4-triazol-3-yl)-thiophen-3-yl)-3,4'-bipyridine-2'-carboxamide | 36 |
| 4 | 6-cyclopropyl-N-(5-(4-cyclopropyl-4H-1,2,4-triazol-3-yl)thiophen-3-yl)-3,4'-bipyridine-2'-carboxamide | 31 |
| 5 | (S)-4-(4-cyclopropyl-1H-imidazol-1-yl)-N-(5-(4-(3-methylbutan-2-yl)-4H-1,2,4-triazol-3-yl)thiophen-3-yl)picolinamide | 204 |
| 6 | (S)-4-(4-cyclopropyl-1H-imidazol-1-yl)-N-(5-(4-(1,1,1-trifluoropropan-2-yl)-4H-1,2,4-triazol-3-yl)thiophen-3-yl)picolinamide | 34 |
| 7 | (S)-4-(4-cyclopropyl-1H-imidazol-1-yl)-N-(5-(4-(1-phenylethyl)-4H-1,2,4-triazol-3-yl)thiophen-3-yl)picolinamide | 548 |
| 8 | 4-(4-cyclopropyl-1H-imidazol-1-yl)-N-(5-(4-(3-hydroxybutan-2-yl)-4H-1,2,4-triazol-3-yl)thiophen-3-yl)picolinamide | 51. |
| 9 | 4-(4-cyclopropyl-1H-imidazol-1-yl)-N-(5-(4-(4,4,4-trifluoro-3-hydroxybutan-2-yl)-4H-1,2,4-triazol-3-yl)thiophen-3-yl)picolinamide | 1320 |
| 10 | 6-cyclopropyl-N-(2-(4-cyclopropyl-4H-1,2,4-triazol-3-yl)thiazol-4-yl)-3,4'-bipyridine-2'-carboxamide | 18 |
| 11 | N-(2-(4-cyclopropyl-4H-1,2,4-triazol-3-yl)-thiazol-4-yl)-3,4'-bipyridine-2'-carboxamide | 6 |
| 12 | 4-(1H-benzo[d]imidazol-1-yl)-N-(4-(4-cyclopropyl-4H-1,2,4-triazol-3-yl)thiazol-2-yl)picolinamide | 56 |
| 13 | N-(4-(4-cyclopropyl-4H-1,2,4-triazol-3-yl)thiazol-2-yl)-3,4'-bipyridine-2'-carboxamide | 109 |
| 14 | N-(4-(4-cyclopropyl-4H-1,2,4-triazol-3-yl)thiazol-2-yl)-6-methoxy-3,4'-bipyridine-2'-carboxamide | 177 |
| 15 | 3-(4-cyclopropyl-1H-imidazol-1-yl)-N-(2-(4-cyclopropyl-4H-1,2,4-triazol-3-yl)thiazol-4-yl)-benzamide | 21 |
| 16 | 4-(4-cyclopropyl-1H-imidazol-1-yl)-N-(2-(4-cyclopropyl-4H-1,2,4-triazol-3-yl)thiazol-4-yl) picolinamide | 7 |
| 17 | N-(5-(4-cyclopropyl-4H-1,2,4-triazol-3-yl)thiophen-3-yl)-4-(4-(pyridin-2-yl)-1H-imidazol-1-yl)-picolinamide | 831 |
| 18 | N-(5-(4-cyclopropyl-4H-1,2,4-triazol-3-yl)thiophen-3-yl)-4-(4-(pyridin-3-yl)-1H-imidazol-1-yl)-picolinamide | 320 |
| 19 | N-(5-(4-cyclopropyl-4H-1,2,4-triazol-3-yl)thiophen-3-yl)-5-(6-cyclopropylpyridin-3-yl)-2-methoxybenzamide | >10,000 |
| 20 | N-(5-(4-cyclopropyl-4H-1,2,4-triazol-3-yl)thiophen-3-yl)-5-(6-cyclopropylpyridin-3-yl)-2,4-dimethoxybenzamide | >10,000 |
| 21 | 5-(4-cyclopropyl-1H-imidazol-1-yl)-N-(5-(4-cyclopropyl-4H-1,2,4-triazol-3-yl)thiophen-3-yl)-2-methoxybenzamide | 92 |

-continued

| No. | Compound | IC50 |
|---|---|---|
| 22 | 5-(4-cyclopropyl-1H-imidazol-1-yl)-N-(2-(4-cyclopropyl-4H-1,2,4-triazol-3-yl)thiazol-4-yl)-2-methoxybenzamide | 7 |
| 23 | 4-(4-bromo-1H-imidazol-1-yl)-N-(5-(4-cyclopropyl-4H-1,2,4-triazol-3-yl)thiophen-3-yl)-picolinamide | 749 |
| 24 | 4-(4-cyclopropyl-1H-imidazol-1-yl)-N-(2-(4-isopropyl-4H-1,2,4-triazol-3-yl)thiazol-4-yl)-picolinamide | 7 |
| 25 | 5-(4-cyclopropyl-1H-imidazol-1-yl)-N-(5-(4-cyclopropyl-4H-1,2,4-triazol-3-yl)thiophen-3-yl)-2-fluorobenzamide (549150 | 240 |
| 26 | (S)-4-(4-cyclopropyl-1H-imidazol-1-yl)-N-(2-(4-(3-methylbutan-2-yl)-4H-1,2,4-triazol-3-yl)thiazol-4-yl)picolinamide | 5 |
| 26 | 5-(4-cyclopropyl-1H-imidazol-1-yl)-N-(2-(4-cyclopropyl-4H-1,2,4-triazol-3-yl)thiazol-4-yl)-2-fluorobenzamide | 20 |
| 27 | (R)-4-(4-cyclopropyl-1H-imidazol-1-yl)-N-(5-(4-(2,2-dimethylcyclopropyl)-4H-1,2,4-triazol-3-yl)thiophen-3-yl)picolinamide | 133 |
| 28 | (S)-4-(4-cyclopropyl-1H-imidazol-1-yl)-N-(5-(4-(2,2-dimethylcyclopropyl)-4H-1,2,4-triazol-3-yl)thiophen-3-yl)picolinamide | 16 |
| 29 | 4-(4-cyclopropyl-1H-imidazol-1-yl)-N-(2-(4-cyclopropyl-4H-1,2,4-triazol-3-yl)thiazol-4-yl)-5-methylpicolinamide | 7 |
| 30 | 4-(4-cyclopropyl-1H-imidazol-1-yl)-N-(5-(4-cyclopropyl-4H-1,2,4-triazol-3-yl)thiophen-3-yl)-5-methylpicolinamide | 7 |
| 31 | (S)-4-(4-cyclopropyl-1H-imidazol-1-yl)-N-(2-(4-(1,1,1-trifluoropropan-2-yl)-4H-1,2,4-triazol-3-yl)thiazol-4-yl)picolinamide | 3 |
| 32 | 4-(4-tert-butyl-1H-imidazol-1-yl)-N-(5-(4-cyclopropyl-4H-1,2,4-triazol-3-yl)thiophen-3-yl)picolinamide; (557830 | 4 |
| 33 | (S)-4-(4-cyclopropyl-1H-imidazol-1-yl)-5-methyl-N-(2-(4-(1,1,1-trifluoropropan-2-yl)-4H-1,2,4-triazol-3-yl)thiazol-4-yl)picolinamide | 3 |

What is claimed is:

1. A compound selected from the group consisting of:

4-(4-cyclopropyl-1H-imidazol-1-yl)-N-(2-(4-(4,4,4-trifluoro-3-hydroxybutan-2-yl)-4H-1,2,4-triazol-3-yl)thiazol-4-yl)picolinamide;

(S)-4-(4-cyclopropyl-1H-imidazol-1-yl)-N-(2-(4-(3-methylbutan-2-yl)-4H-1,2,4-triazol-3-yl)thiazol-4-yl) picolinamide;

(S)-4-(4-cyclopropyl-1H-imidazol-1-yl)-N-(2-(4-(1,1,1-trifluoropropan-2-yl)-4H-1,2,4-triazol-3-yl)thiazol-4-yl)picolinamide;

4-(4-cyclopropyl-1H-imidazol-1-yl)-N-(2-(4-isopropyl-4H-1,2,4-triazol-3-yl)thiazol-4-yl)picolinamide;

(S)-4-(4-cyclopropyl-1H-imidazol-1-yl)-5-methyl-N-(2-(4-(1,1,1-trifluoropropan-2-yl)-4H-1,2,4-triazol-3-yl) thiazol-4-yl)picolinamide; and (S)-4-(4-tert-butyl-1H-imidazol-1-yl)-5-methyl-N-(2-(4-(1,1,1-trifluoropropan-2-yl)-4H-1,2,4-triazol-3-yl)thiazol-4-yl)picolinamide;

or a pharmaceutically acceptable salt thereof.

2. The compound selected from the group consisting of:

6-cyclopropyl-N-(2-(4-cyclopropyl-4H-1,2,4-triazol-3-yl)thiazol-4-yl)-3,4'-bipyridine-2'-carboxamide;

N-(2-(4-cyclopropyl-4H-1,2,4-triazol-3-yl)thiazol-4-yl)-3,4'-bipyridine-2'-carboxamide;

4-(4-cyclopropyl-H-imidazol-1-yl)-N-(2-(4-cyclopropyl-4H-1,2,4-triazol-3-yl)thiazol-4-yl)picolinamide, and 4-(4-cyclopropyl-1H-imidazol-1-yl)-N-(2-(4-cyclopropyl-4H-1,2,4-triazol-3-yl)thiazol-4-yl)-5-methylpicolinamide;

or a pharmaceutically acceptable salt thereof.

3. The compound selected from the group consisting of:

4-(1H-benzo[d]imidazol-1-yl)-N-(4-(4-cyclopropyl-4H-1,2,4-triazol-3-yl)thiazol-2-yl)picolinamide;

N-(4-(4-cyclopropyl-4H-1,2,4-triazol-3-yl)thiazol-2-yl)-3,4'-bipyridine-2'-carboxamide; and N-(4-(4-cyclopropyl-4H-1,2,4-triazol-3-yl)thiazol-2-yl)-6-methoxy-3,4'-bipyridine-2'-carboxamide;

or a pharmaceutically acceptable salt thereof.

4. A pharmaceutical composition comprising [an] *a therapeutically* effective amount of one or more compounds according to claim 1 and a pharmaceutically acceptable excipient.

5. A pharmaceutical composition comprising [an] *a therapeutically* effective amount of one or more compounds according to claim 2 and a pharmaceutically acceptable excipient.

6. A pharmaceutical composition comprising [an] *a therapeutically* effective amount of one or more compounds according to claim 3 and a pharmaceutically acceptable excipient.

*7. The pharmaceutical composition of claim 4, wherein the therapeutically effective amount is from 1 mg to 2 g.*

*8. The pharmaceutical composition of claim 5, wherein the therapeutically effective amount is from 1 mg to 2 g.*

*9. The pharmaceutical composition of claim 6, wherein the therapeutically effective amount is from 1 mg to 2 g.*

* * * * *